(12) United States Patent
Cohn et al.

(10) Patent No.: US 9,526,813 B2
(45) Date of Patent: Dec. 27, 2016

(54) INTRALUMINAL POLYMERIC DEVICES FOR THE TREATMENT OF ANEURYSMS

(75) Inventors: Daniel Cohn, Jerusalem (IL); Itai Pelled, Ramat-HaSharon (IL); Randa Abbas, Kafr Kanna (IL); Ram Malal, Jerusalem (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 188 days.

(21) Appl. No.: 13/383,588

(22) PCT Filed: Jul. 13, 2010

(86) PCT No.: PCT/IL2010/000562
§ 371 (c)(1),
(2), (4) Date: Mar. 22, 2012

(87) PCT Pub. No.: WO2011/007352
PCT Pub. Date: Jan. 20, 2011

(65) Prior Publication Data
US 2012/0179193 A1    Jul. 12, 2012

Related U.S. Application Data

(60) Provisional application No. 61/225,063, filed on Jul. 13, 2009.

(51) Int. Cl.
*A61M 29/04* (2006.01)
*A61L 31/06* (2006.01)
*A61F 2/945* (2013.01)

(52) U.S. Cl.
CPC .......... *A61L 31/06* (2013.01); *A61F 2/945* (2013.01)

(58) Field of Classification Search
CPC ....... A61F 2/82–2/97; A61F 2/00; A61F 2/07; A61F 2/945; A61F 2002/072–2002/077; A61L 31/06; A61M 29/02
(Continued)

(56) References Cited

U.S. PATENT DOCUMENTS

| 5,147,385 A | 9/1992 | Beck et al. |
| 5,662,712 A * | 9/1997 | Pathak ............... A61F 2/945 606/195 |

(Continued)

FOREIGN PATENT DOCUMENTS

| DE | 4447101 | 7/1996 |
| WO | WO 2008/011615 | 1/2008 |

(Continued)

OTHER PUBLICATIONS

International Search Report and the Written Opinion Dated Feb. 11, 2011 From the International Searching Authority Re. Application No. PCT/IL2010/000562.

(Continued)

*Primary Examiner* — Julian W Woo
*Assistant Examiner* — Shaun L David

(57) ABSTRACT

Novel medical devices and uses thereof for lining a blood vessel and/or treating an aneurysm are disclosed herein. The device comprises a non-metallic expandable tubular structure, implantable in a body vessel and being made, at least in part, from a polymeric system characterized by a stiffness which changes upon stimulation under physiological conditions. Novel polymeric systems are further disclosed herein, which are configured to produce a polymeric material upon stimulation under physiological conditions, such that a stiffness of said polymeric material is higher than a stiffness of said system. Uses of polymer systems in the manufacture of a device are further disclosed.

38 Claims, 30 Drawing Sheets
(20 of 30 Drawing Sheet(s) Filed in Color)

(58) Field of Classification Search
USPC .............. 623/1.12, 1.15, 1.49, 1.21; 606/198
See application file for complete search history.

(56) References Cited

U.S. PATENT DOCUMENTS

| | | | |
|---|---|---|---|
| 5,800,518 A * | 9/1998 | Piplani et al. ................. | 128/898 |
| 6,248,129 B1 * | 6/2001 | Froix ............................ | 623/1.42 |
| 6,551,350 B1 * | 4/2003 | Thornton et al. ............. | 623/1.13 |
| 2003/0083738 A1 * | 5/2003 | Holman et al. ............... | 623/1.35 |
| 2004/0193245 A1 | 9/2004 | Deem et al. | |
| 2004/0199246 A1 * | 10/2004 | Chu et al. ..................... | 623/1.44 |
| 2005/0137678 A1 * | 6/2005 | Varma ........................... | 623/1.15 |
| 2005/0267570 A1 * | 12/2005 | Shadduck ..................... | 623/1.44 |
| 2006/0058868 A1 * | 3/2006 | Gale et al. .................... | 623/1.15 |
| 2007/0260268 A1 * | 11/2007 | Bartee et al. ................. | 606/151 |
| 2007/0282366 A1 * | 12/2007 | Khosravi et al. ............. | 606/192 |

FOREIGN PATENT DOCUMENTS

| | | |
|---|---|---|
| WO | WO 2008011615 A2 * | 1/2008 |
| WO | WO 2011/007352 | 1/2011 |

OTHER PUBLICATIONS

Communication Pursuant to Article 94(3) EPC Dated Dec. 12, 2012 From the European Patent Office Re. Application No. 10752433.2.
Office Action Dated Aug. 15, 2013 From the Israel Patent Office Re. Application No. 217529 and Its Translation Into English.
International Preliminary Report on Patentability Dated Jan. 26, 2012 From the International Bureau of WIPO Re. Application No. PCT/IL2010/000562.
Communication Pursuant to Article 94(3) EPC Dated Sep. 22, 2014 From the European Patent Office Re. Application No. 10752433.2.
Communication Pursuant to Article 94(3) EPC Dated Feb. 12, 2016 From the European Patent Office Re. Application No. 10752433.2.

\* cited by examiner

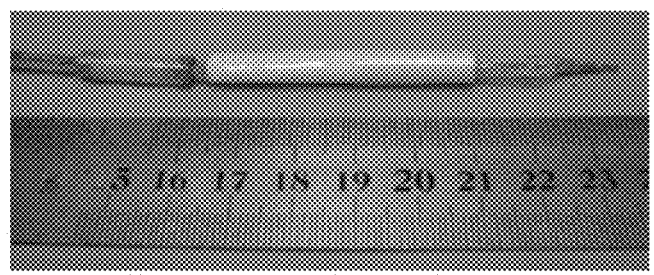
FIG. 27
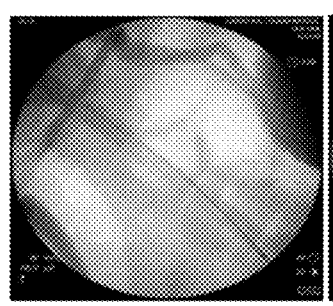 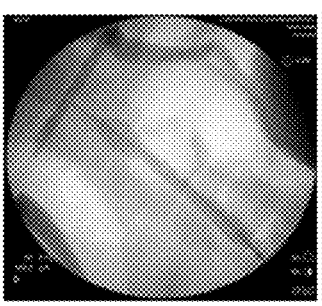 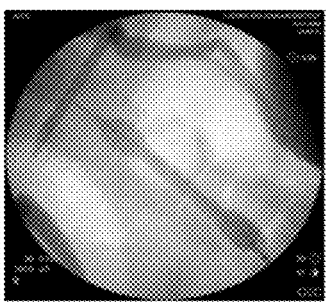
FIG. 28A      FIG. 28B      FIG. 28C
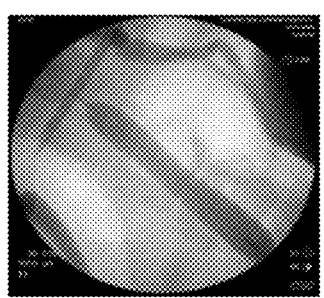 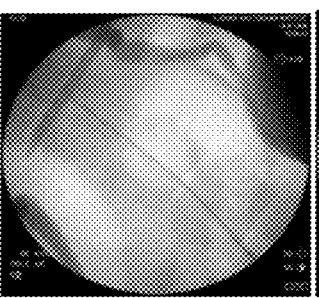 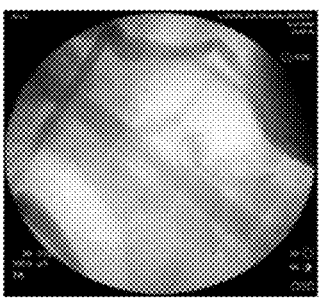
FIG. 28D      FIG. 28E      FIG. 28F

INTRALUMINAL POLYMERIC DEVICES FOR THE TREATMENT OF ANEURYSMS

RELATED APPLICATIONS

This application is a National Phase of PCT Patent Application No. PCT/IL2010/000562 having International filing date of Jul. 13, 2010, which claims the benefit of priority under 35 USC §119(e) of U.S. Provisional Patent Application No. 61/225,063 filed on Jul. 13, 2009. The contents of the above applications are all incorporated herein by reference as if fully set forth herein.

FIELD AND BACKGROUND OF THE INVENTION

The present invention, in some embodiments thereof, relates to a polymeric device, and more particularly, but not exclusively, to a polymeric device useful for the treatment of an aneurysm and to polymeric systems useful for forming such a device.

The formation of aneurysms is a life-threatening degenerative pathology of arterial tissues whereby the wall of the artery weakens locally and markedly expands, creating a sac, which can potentially rupture. The expanded arterial sections are considered aneurysms of clinical relevance when their diameter is at least twice that of the normal artery. Before rupture occurs, an aneurysm seldom causes symptomatic pain or other symptoms. The bulging of the artery and its rupture typically occur in specific locations in the brain and in the thoracic and abdominal aorta. Abdominal aortic aneurysms (AAA) are particularly deadly, with fewer than 20% of victims surviving AAA rupture. Bursts of abdominal aortic aneurysms (AAA), the most common type of aneurysm, are ranked as the $13^{th}$ most common cause of mortality in the U.S, and the $10^{th}$ most common cause among U.S. men over the age of 55. Abdominal Aortic Aneurysms are present in about 1.2 million people in the U.S. (as of 2008).

The formation of an aneurysm is accompanied by a profound histological change in the tissue composition of the arterial wall. While the elastin and collagen content of a healthy aorta are about 36% and 23%, respectively, aneurysmal tissue displays a much lower elastin content (about 6%) and a much higher collagen content (about 45%). These changes result in a marked change of mechanical properties, with the longitudinal tensile strength decreasing from approximately 160 kPa to approximately 120 kPa, and the stiffness increasing from approximately 275 kPa to approximately 450 kPa.

Aneurysms are especially common in adult and elderly populations, particularly white men above the age of 55. According to current theories, an underlying genetic factor is likely involved in the formation of aneurysms, although additional factors such as high blood pressure, arteriosclerosis and smoking also play a role.

The mortality rate of aneurysms is high because the creation and expansion of aneurysms is a silent process until a burst occurs. The risk of rupture can be estimated by the size of the aneurysm. It is widely considered that the danger of rupture is high when the diameter of the aneurysm is about 5-6 centimeters, in which case the aneurysm should be treated without delay. In the case of smaller aneurysms, surgeons tend to differ as to the need for surgery.

Until 1991, the only available treatment entailed a fully open surgical procedure, whereby the dilated segment of the artery was replaced by an artificial vascular graft. The traditional treatment of AAA is performed by open abdominal surgery with full anesthesia, putting aside the abdominal organs, clamping the aorta and replacing the aneurysmal segment with Dacron® (polyethylene terephthalate) or expanded PTFE (polytetrafluoroethylene) arterial prostheses. These grafts have been widely implanted for several decades with good results, but have all the drawbacks associated with invasive surgical procedures. Intraoperative mortality rates range from approximately 2% to above 10%, and post-operative morbidity of 30% has been reported. In addition, even without complications, patients must remain in the hospital for 7 to 10 days after surgery, and are usually able to return to work only after about 6 weeks.

An endograft consisting of a vascular prosthesis mounted on a stent, and deployed intraluminally at the aneurysmal site using a balloon, was implanted for the first time in 1991. Once the stent is locked in place and the prosthesis is firmly positioned, the balloon is deflated and retrieved. This minimally invasive technique, named Endovascular Aortic Repair (EVAR), has several advantages, the most important of which stems from the much shorter hospitalization and recovery periods required by this technique. Patients undergoing EVAR are usually discharged after two days in the hospital and are fully recovered after approximately two weeks.

However, various factors restrict the use of EVAR. Consequently, only about 60% of AAA repair treatments are performed using the stent/graft system. Rather strict anatomical considerations pertaining to the dimensions of the artery both proximal and distal to the aneurysmal site may prevent the use of the graft. For example, if the diameter of the proximal vessel is too large, the device may dislodge from its intended position.

In addition, renewed leakage into the aneurysmal sac (endoleak) is a major problem. There are four types of endoleaks: migration or lack of sealing; leakage through arteries in branching points; leakage through the fabric; and leakage through other components of the stent/graft device. The different types of endoleaks can result in the burst of the aneurysm despite the presence of the graft, and approximately 50% of such ruptures lead to the death of the patient.

Furthermore, it was found that in approximately 40% of EVAR procedures, there was no change in the aneurysmal sac.

In addition, the stent/graft device used in EVAR is quite expensive, and may cost approximately 12,000 $.

U.S. Patent Application having Publication No. 2008/0063620 describes a polymeric system in which a polymeric component is capable of undergoing a transition that results in a sharp increase in viscosity in response to a change in temperature. The polymers are suitable for biomedical applications, such as drug delivery systems, prevention of post-surgical adhesions, sealants and tissue engineering.

U.S. Patent Application having Publication No. 2007/0116666 describes polyester/poly(oxyalkylene) triblock and diblock copolymers for reducing post-surgical adhesions.

U.S. Patent Application having Publication No. 2008/0133001 describes a medical device comprising a tubular structure for implantation in a vasculature, composed of a plastically deformable fiber. The plastically deformable fiber comprises a non-distensible polymer and an elastic polymer.

Additional background art includes U.S. Pat. No. 7,425,322; U.S. Pat. No. 7,569,643; International Patent Application PCT/IL2002/00699 (published as WO 2003/017972); International Patent Application PCT/IL2009/000865 (published as WO 2010/026590); and U.S. Patent Application having Publication No. 2010/0136084.

SUMMARY OF THE INVENTION

In view of the shortcomings of the current clinical methodologies used in the treatment of aneurysm, particularly AAA, the present inventors have devised and successfully practiced a novel methodology, which is aimed at preventing the rupture of the aneurysm by in situ generating a polymeric device that isolates the sac from the blood stream, following a minimally invasive surgical procedure.

Embodiments of the present invention therefore relate to forming an isolating tubular structure that is deployed intraluminally at the aneruysmal site and then expanded, so that it tightly attaches to the vessel, proximally and distally to the aneurysm. The device described herein achieves two objectives: (a) isolating the weak aneurysmal arterial wall from the aortic blood stream, thereby immediately minimizing the risk of life-threatening hemorrhage due to sudden rupture; and (b) restoring the artery's luminal cylindrical geometry, distorted by the aneurysmal expansion. The snug and secure attachment of the device to the normal aortic lumen prevents its dislodgment from its position and avoids the occurrence of endoleaks.

The device described herein is based on the formation of a tubular structure from a polymeric system that is sufficiently flexible at deployment, and which stiffens as a result of a stimulation (e.g., via chemical and/or physical phenomena) at the deployment site.

The device may further promote the regeneration of healthy aortic tissue at the aneurysmal site.

According to an aspect of some embodiments of the present invention there is provided a medical device comprising a non-metallic expandable tubular structure, implantable in a body vessel and being made, at least in part, from a polymeric system characterized by a stiffness which changes upon stimulation under physiological conditions, such that the tubular structure is capable of expanding, becoming stiffer and retaining an expanded state thereafter.

According to an aspect of some embodiments of the present invention there is provided a polymeric system configured to produce a polymeric material upon stimulation under physiological conditions, such that a stiffness of the polymeric material is higher than a stiffness of the system.

According to an aspect of some embodiments of the present invention there is provided a method of lining a body vessel, the method comprising introducing the medical device described herein into the vessel.

According to an aspect of some embodiments of the present invention there is provided a use of a polymeric system having a stiffness which increases upon stimulation under physiological conditions in the manufacture of a medical device for lining a body vessel and/or treating an aneurysm.

According to an aspect of some embodiments of the present invention there is provided a use of the polymeric system described herein in the manufacture of a medical device for lining a body vessel and/or for treating an aneurysm.

According to an aspect of some embodiments of the present invention there is provided a use of a thermoplastic polymer which undergoes a decrease of its stiffness of at least 20% at a temperature ranging from 40° C. to 60° C. in the manufacture of a medical device for lining a body vessel and/or treating an aneurysm.

According to an aspect of some embodiments of the present invention there is provided a thermoplastic polymer which undergoes a decrease of its stiffness of at least 20% at a temperature ranging from 40° C. to 60° C., identified for use in a method of lining a body vessel.

According to an aspect of some embodiments of the present invention there is provided a thermoplastic polymer which undergoes a decrease of its stiffness of at least 20% at a temperature ranging from 40° C. to 60° C., identified for use in a method of treating an aneurysm in a subject in need thereof.

According to an aspect of some embodiments of the present invention there is provided a method of lining a body vessel, comprising:

introducing into the vessel a tubular structure made, at least in part, from a thermoplastic polymer which undergoes a decrease of at least 20% in its stiffness at a temperature ranging from about 40° C. to about 60° C.;

heating the thermoplastic polymer so as to decrease the stiffness by at least 20%;

expanding the softened thermoplastic polymer; and generating conditions for the thermoplastic polymer to cool to a physiological temperature, such that the tubular structure experiences stiffening, thereby lining the vessel.

According to some embodiments of the invention, the stimulation is selected from the group consisting of thermal stimulation, mechanical stimulation, chemical stimulation, optical stimulation and electrical stimulation.

According to some embodiments of the invention, the tubular structure is capable of contracting upon stimulation following the expansion, and retaining, at least temporarily, a contracted state thereafter.

According to some embodiments of the invention, the tubular structure is a branched tubular structure having at least a first branch member and a second branch member, and wherein the polymeric system is selected such that the first branch member is weldable to the second branch member in situ.

According to some embodiments of the invention, the tubular structure comprises a plurality of weldable tubular layer members configured for allowing sequential positioning of the layer members to form, in situ, a multilayer tubular structure in the vessel.

According to some embodiments of the invention, at least one of the branch members comprises a plurality of weldable tubular layer members configured for allowing sequential positioning of the layer members to form, in situ, a multilayer branch member in the vessel.

According to some embodiments of the invention, the tubular structure is a branched tubular structure having a first branch member and a second branch member, and wherein a wall of at least one of the branch members is folded upon itself forming an inner tubular wall within the abovementioned at least one branch member.

According to some embodiments of the invention, the folded wall is unfoldable in situ.

According to some embodiments of the invention, the device further comprises a compressible member mounted on an end of the tubular structure, for enhancing fixation of the tubular structure in the body vessel.

According to some embodiments of the invention, an outer wall of the tubular structure is at least partially coated by a compressible layer for enhancing fixation of the tubular structure to an inner wall of the body vessel.

According to some embodiments of the invention, an outer wall of the tubular structure is coated by a bioadhesive or an adhesive-forming agent for facilitating fixation of the tubular structure to an inner wall of the body vessel.

According to some embodiments of the invention, the bioadhesive comprises polyacrylic acid.

According to some embodiments of the invention, an outer wall of the tubular structure is modified to increase adhesiveness of the outer wall for enhancing fixation of the tubular structure to an inner wall of the body vessel.

According to some embodiments of the invention, the outer wall is modified so as to comprise hydrophilic functional groups.

According to some embodiments of the invention, the hydrophilic functional groups comprise carboxylic acid groups.

According to some embodiments of the invention, the polymeric system comprises a thermoplastic polymer which undergoes a decrease of its stiffness by at least 20% at a temperature ranging from 40° C. to 60° C.

According to some embodiments of the invention, the thermoplastic polymer is characterized by a transition temperature in a range of from about 45° C. to about 60° C.

According to some embodiments of the invention, the thermoplastic polymer is selected from the group consisting of a polyester, a polycarbonate, a polyurethane, a polyether urethane, a polyether carbonate, a polyester carbonate, a polyester urethane, a polyanhydride, a polyamide, a polyolefin, a polyacrylate, a polymethacrylate, a halogenated polymer and a silicone polymer, and copolymers thereof.

According to some embodiments of the invention, the thermoplastic polyester is a polycaprolactone or a copolymer of polycaprolactone.

According to some embodiments of the invention, the copolymer of polycaprolactone is selected from the group consisting of polycaprolactone-polylactic acid, polycaprolactone-polyethylene glycol, polycaprolactone-polypropylene glycol and polycaprolactone-polytetramethylene glycol.

According to some embodiments of the invention, the polyester is selected from the group consisting of polybutylene succinate, polyethylene adipate and polyethylene sebacate.

According to some embodiments of the invention, the thermoplastic polymer is characterized by a transition temperature in a range of from about 45° C. to about 60° C.

According to some embodiments of the invention, the thermoplastic polymer is an elastomer.

According to some embodiments of the invention, the thermoplastic polymer has a general formula:

[A-B-D-E-]$_m$[G-E-]$_n$ wherein:
A is [—O—X$_1$—C(=O)—]$_o$;
B is —O—[X$_2$—O—]$_p$;
D is [—C(=O)—X$_3$—O—]$_q$;
E is —C(=O)—NH—X$_4$—NH—C(=O)—;
G is [—O—X$_5$]$_r$—O—;
o, p, q and r are each independently integers from 1 to 1,000;
m and n are each independently 0 or an integer from 1 to 1000, wherein at least one of m and n is an integer from 1 to 1000; and
X$_1$-X$_5$ are each independently an alkylene.

According to some embodiments of the invention, the polymeric system is configured to produce a polymeric material upon the stimulation under physiological conditions, such that a stiffness of the polymeric material is higher than a stiffness of the system.

According to some embodiments of the invention, the polymeric system comprises a polymer and a compound which reacts with the polymer upon stimulation, so as to produce the polymeric material.

According to some embodiments of the invention, the compound which reacts with the polymer is selected from the group consisting of a monomer or oligomer which undergoes polymerization upon stimulation and a cross-linker capable of cross-linking the polymer in the polymeric system upon stimulation, to thereby produce a cross-linked form of the polymer as the polymeric material.

According to some embodiments of the invention, the compound is selected from the group consisting of an acrylate, a methacrylate, a diacrylate, a dimethacrylate, a dithiol, a diamine, an aminothiol, an amino acid, an oligopeptide, a bis(azide), a dialkyne, and combinations thereof.

According to some embodiments of the invention, the polymeric system comprises a polymer having a first functional group and a polymer having a second functional group, wherein the first functional group and the second functional group are capable of reacting with one another upon stimulation under physiological conditions to form a cross-linked polymer as the polymeric material.

According to some embodiments of the invention, the polymeric system comprises a polymer having the abovementioned first functional group and the abovementioned second functional group.

According to some embodiments of the invention, the abovementioned first functional group and the abovementioned second functional group are selected from the group consisting of an unsaturated carbon-carbon bond and a thiol, an unsaturated carbon-carbon bond and an amine, a carboxylic acid and an amine, a hydroxyl and an isocyanate, a carboxylic acid and an isocyanate, an amine and an isocyanate, and a thiol and an isocyanate, and combinations thereof.

According to some embodiments of the invention, the polymeric system comprises a polymer and at least one of a monomer or an oligomer which undergoes polymerization.

According to some embodiments of the invention, the monomer is selected from the group consisting of an acrylate, a methacrylate, a diacrylate, and a dimethacrylate.

According to some embodiments of the invention, the polymeric system comprises a polymer and a hydrophilic compound which plasticizes the polymer.

According to some embodiments of the invention, the hydrophilic compound is a polyethylene glycol.

According to some embodiments of the invention, the polymeric system comprises a substance in an amorphous form, and wherein at least a portion of the amorphous form undergoes crystallization upon stimulation under physiological conditions, to thereby produce a crystalline form of the substance.

According to some embodiments of the invention, the substance comprises a polymer.

According to some embodiments of the invention, the substance comprises a cross-linked polymer comprising degradable cross-links which are degraded upon stimulation under physiological conditions, such that at least a portion of the polymer undergoes crystallization following degradation of the cross-links.

According to some embodiments of the invention, the cross-links comprise oligoesters.

According to some embodiments of the invention, the device described herein is identified for use in a method of lining the body vessel.

According to some embodiments of the invention, lining the body vessel is for treating an aneurysm of a blood vessel in a subject in need thereof.

According to some embodiments of the invention, the body vessel is a blood vessel, and the method described herein is for treating an aneurysm in the blood vessel in a subject in need thereof.

According to some embodiments of the invention, the method described herein further comprises expanding the device in situ to thereby form the expanded state.

According to some embodiments of the invention, the method further comprises, subsequent to the expansion of the device in situ, subjecting the device to the stimulation, to thereby increase the stiffness of the polymeric system.

According to some embodiments of the invention, the method further comprises, prior to the expansion of the device in situ, decreasing a stiffness of the polymeric system.

According to some embodiments of the invention, the tubular structure is mounted on a balloon.

According to some embodiments of the invention, the method described herein further comprises inflating the balloon so as to expand the tubular structure.

According to some embodiments of the invention, the method described herein further comprises imaging at least a part of the vessel during the introduction of the device to the vessel.

According to some embodiments of the invention, the aneurysm is an aortic aneurysm.

According to some embodiments of the invention, the aneurysm is an abdominal aortic aneurysm.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings:

Figure 1A:
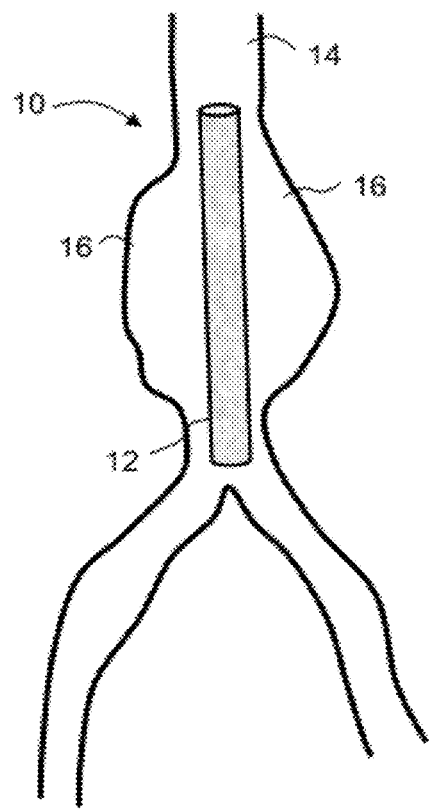
Figure 1B:
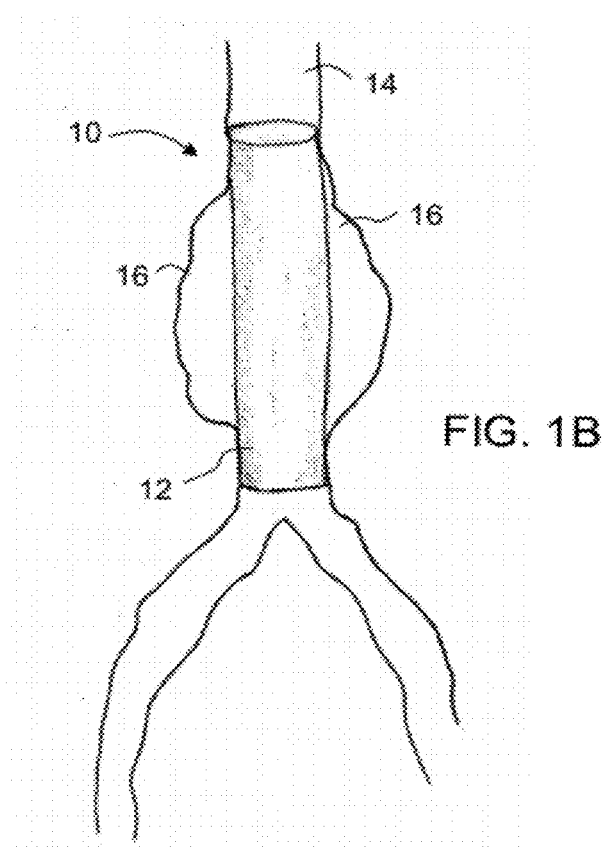
Figure 3:
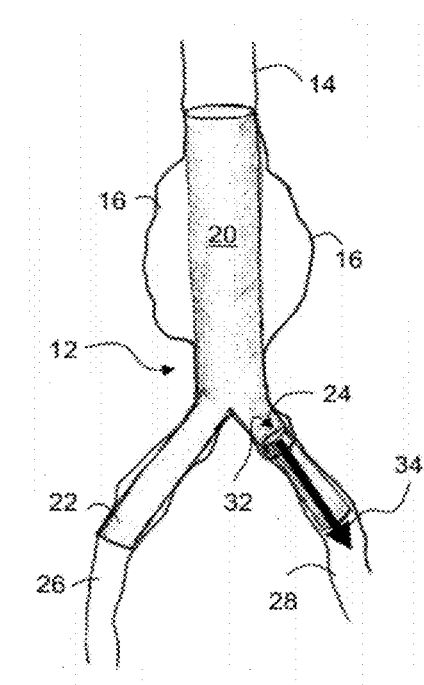
Figure 4A:
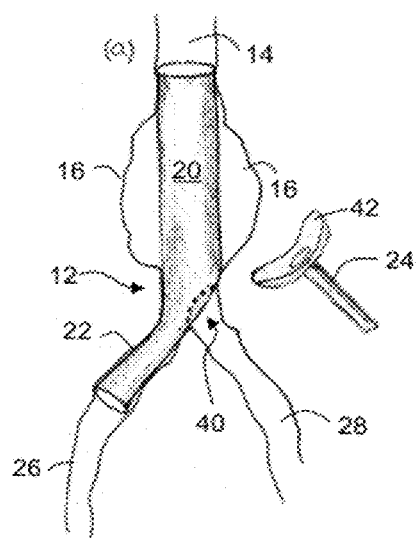
Figure 4B:
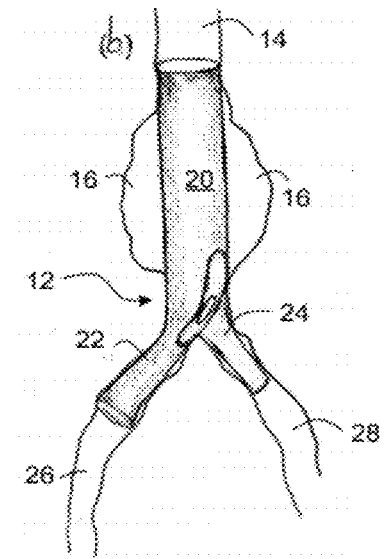
Figure 5:
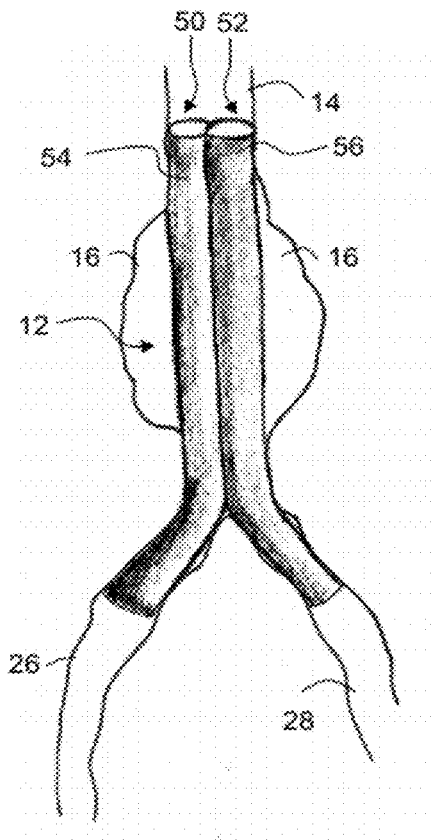
Figure 6:
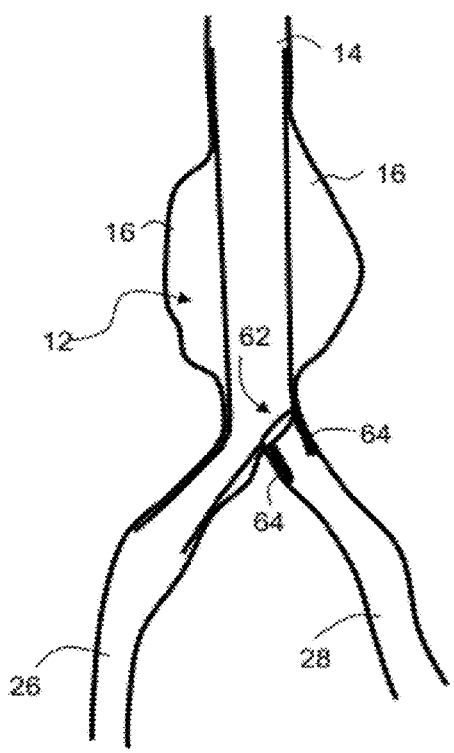
Figure 7:
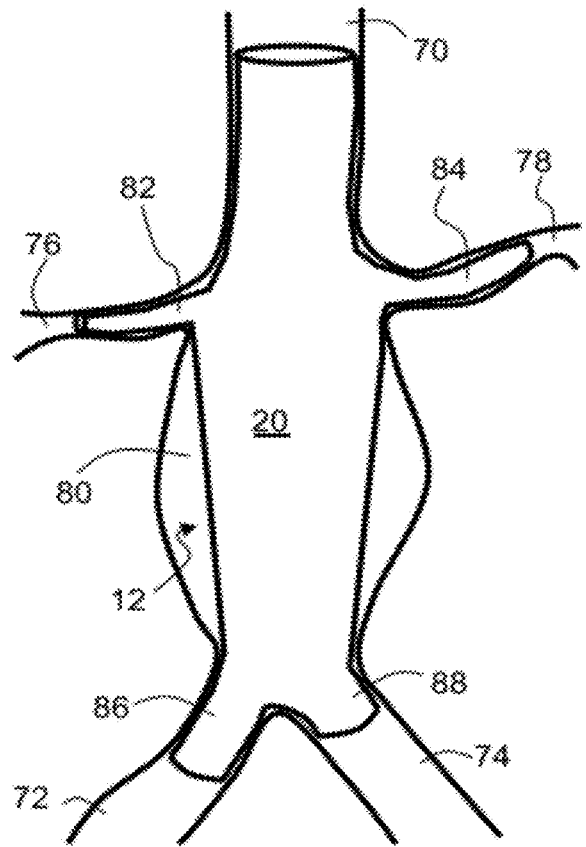
Figure 8:
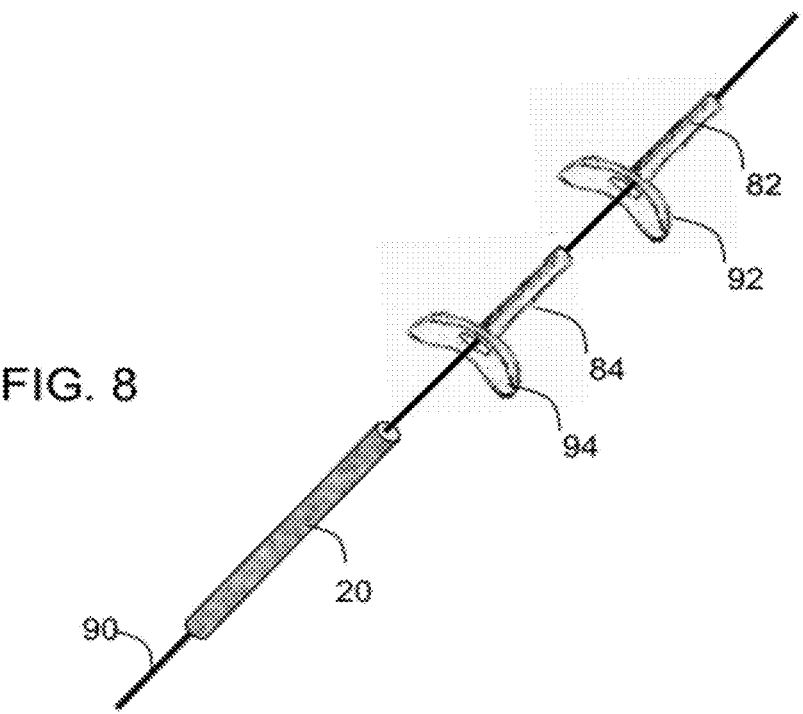
Figure 9A:
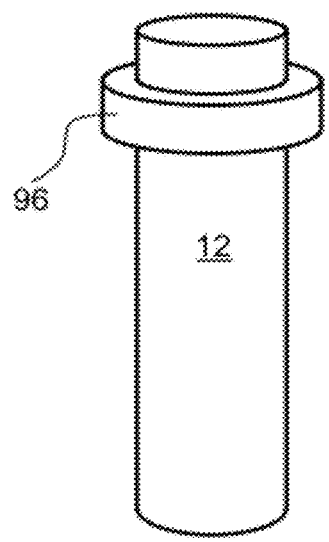
Figure 9B:
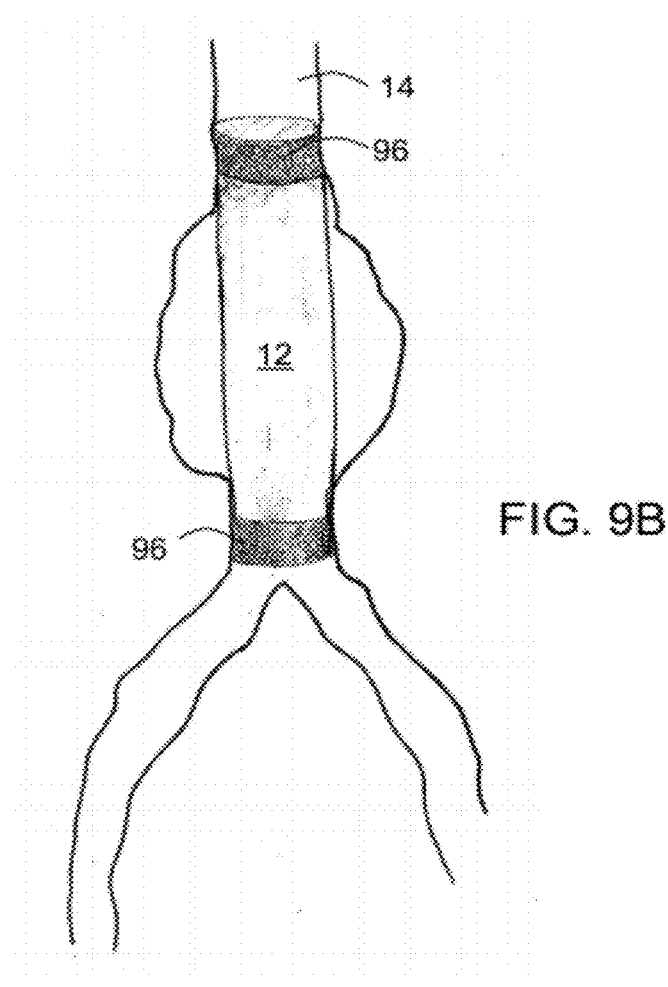
Figure 10:
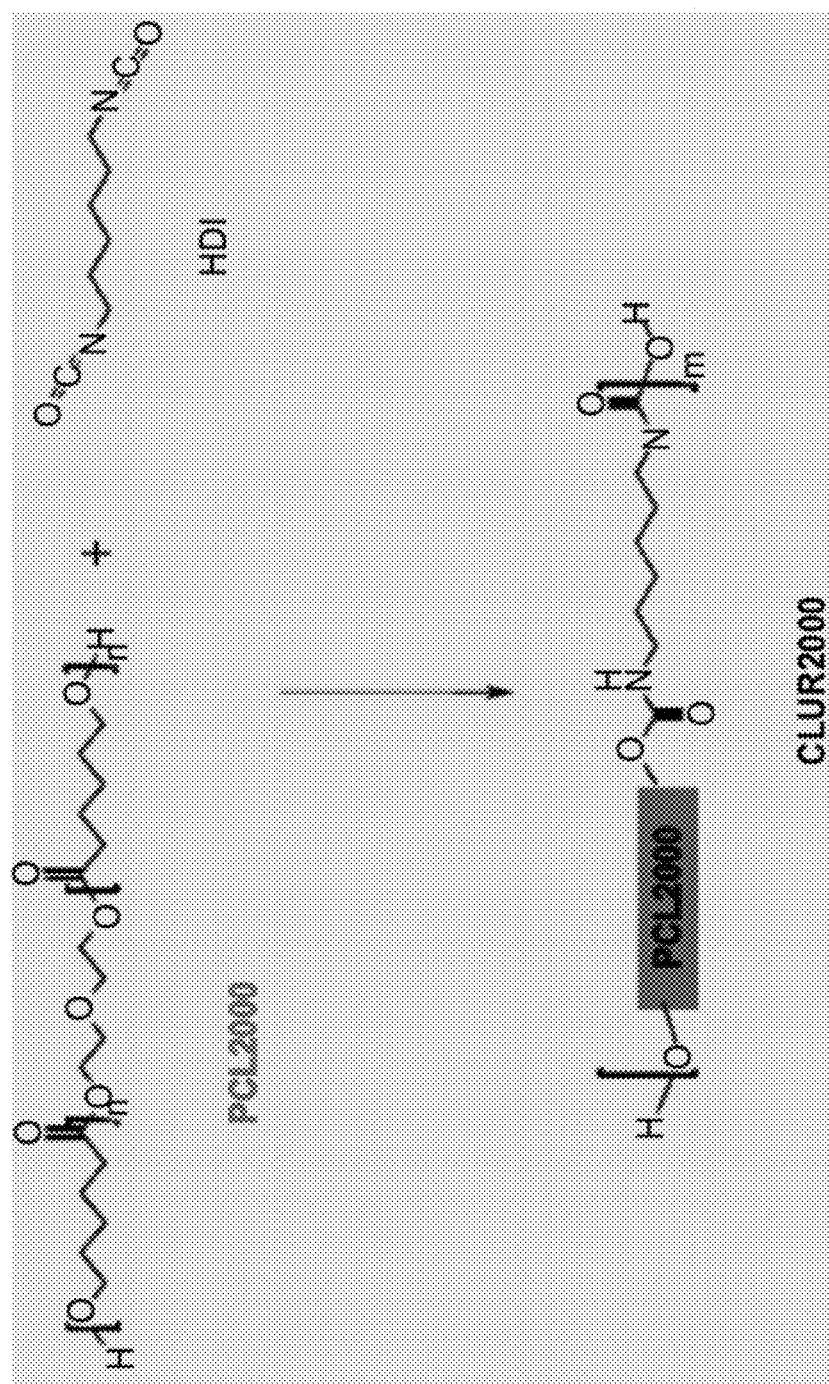
Figure 11:
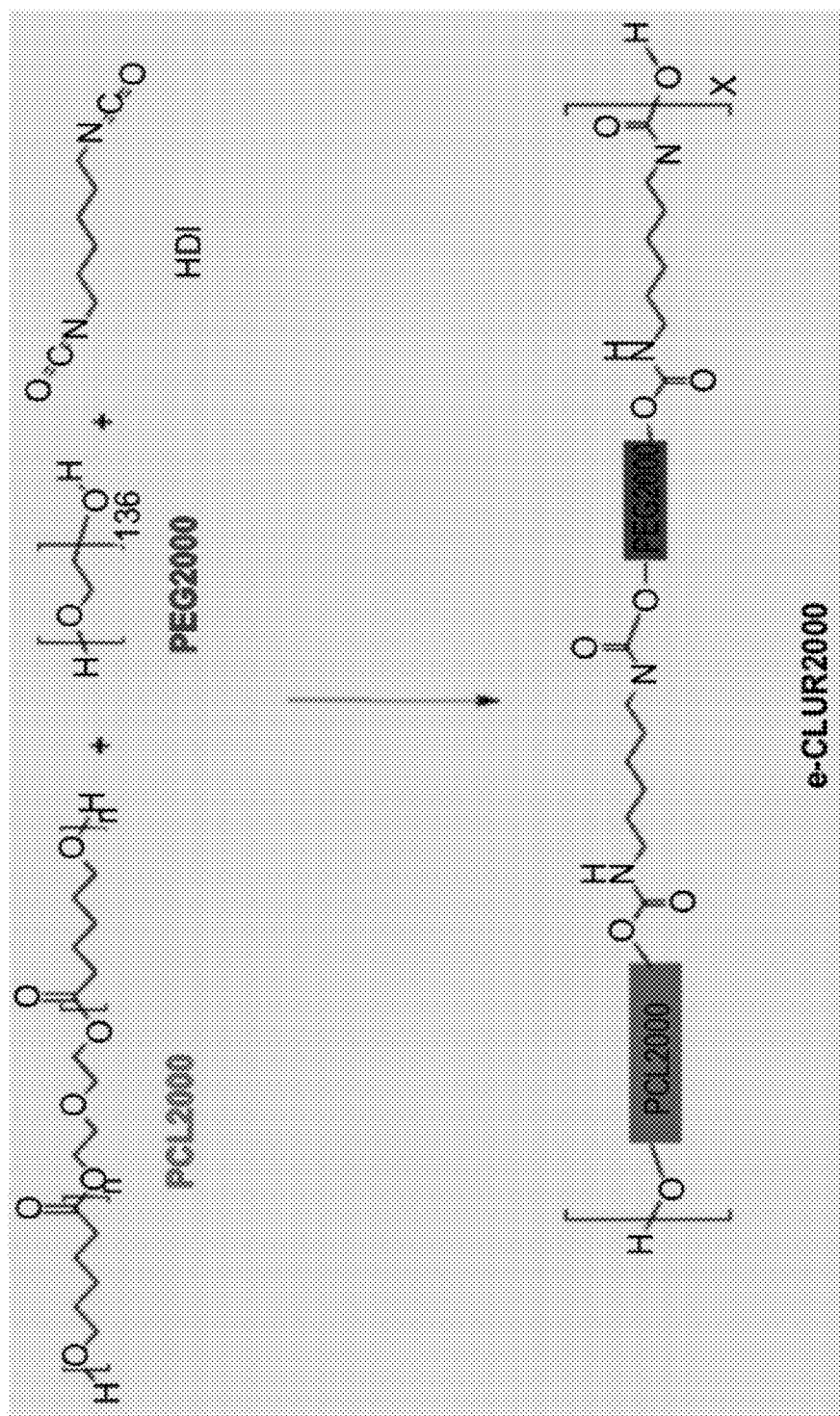
Figure 12A:
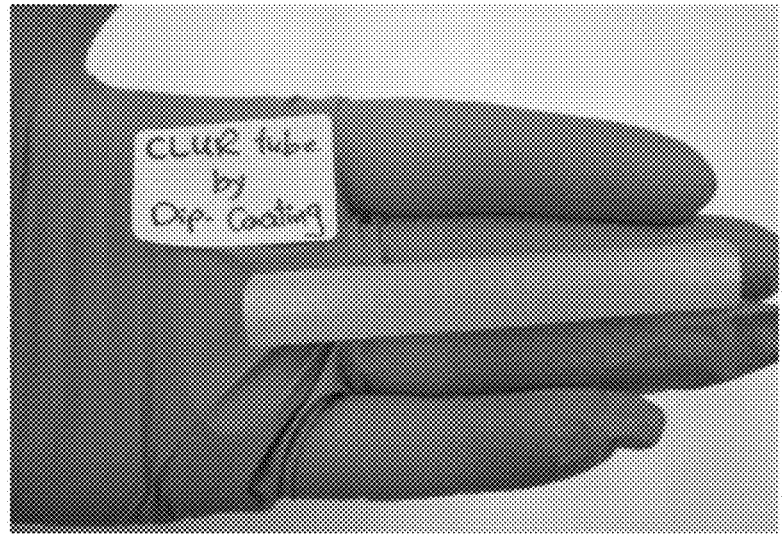
Figure 12B:
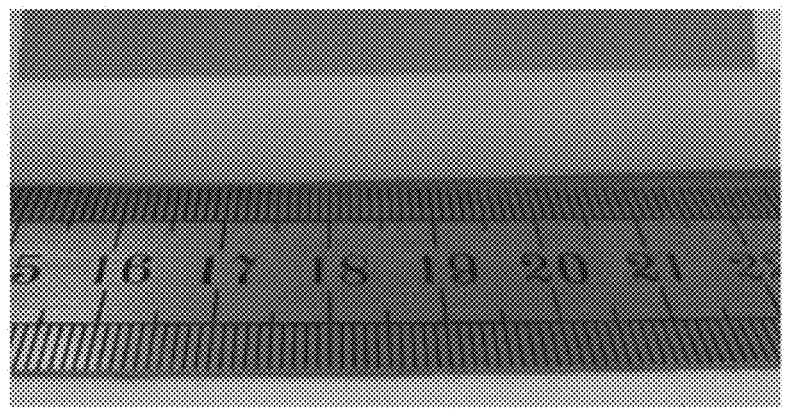
Figure 13:
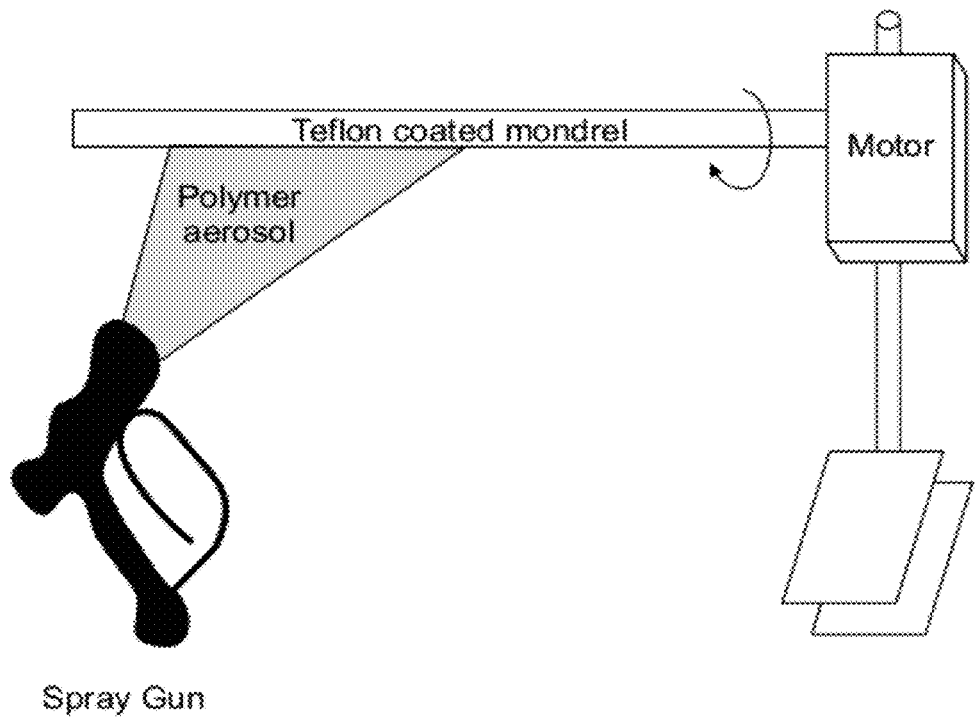
Figure 14:
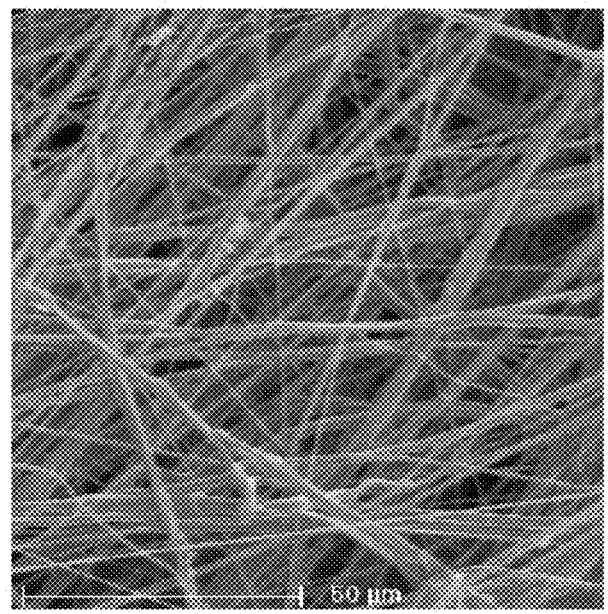
Figure 15:
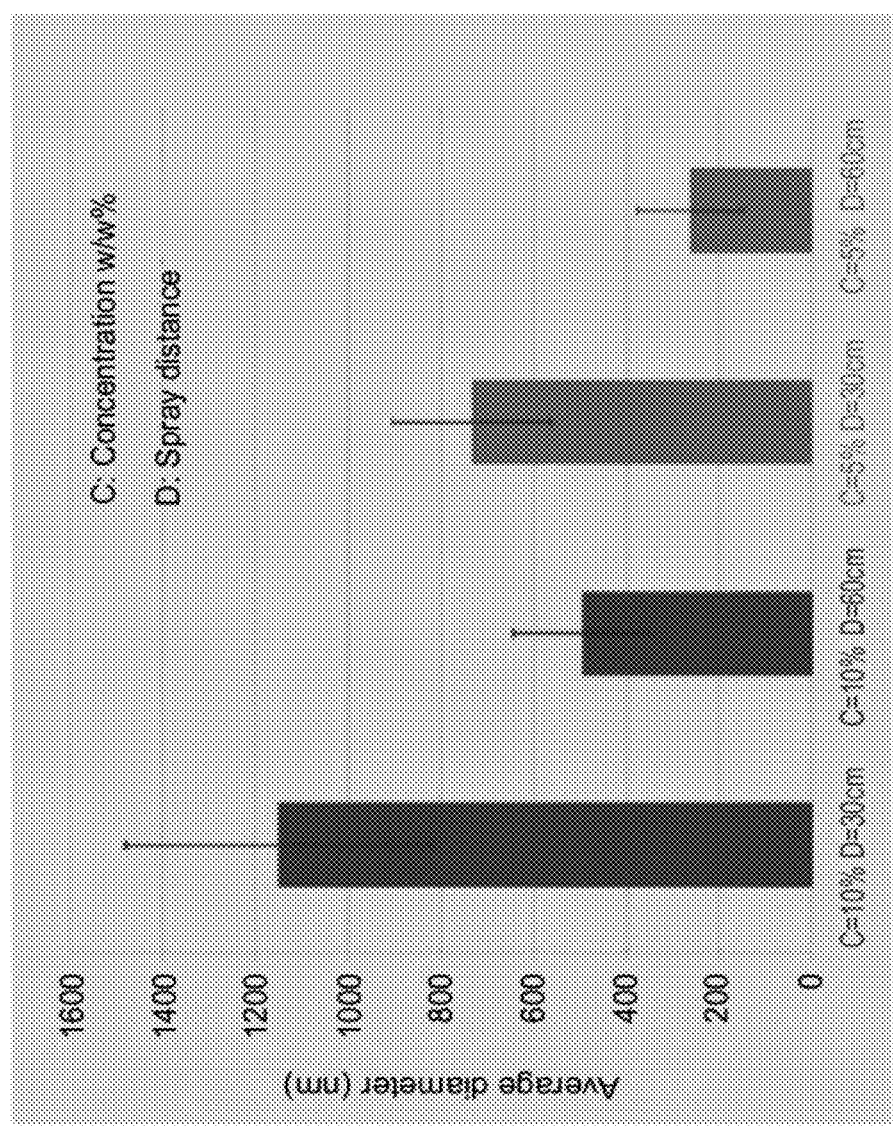
Figure 16:
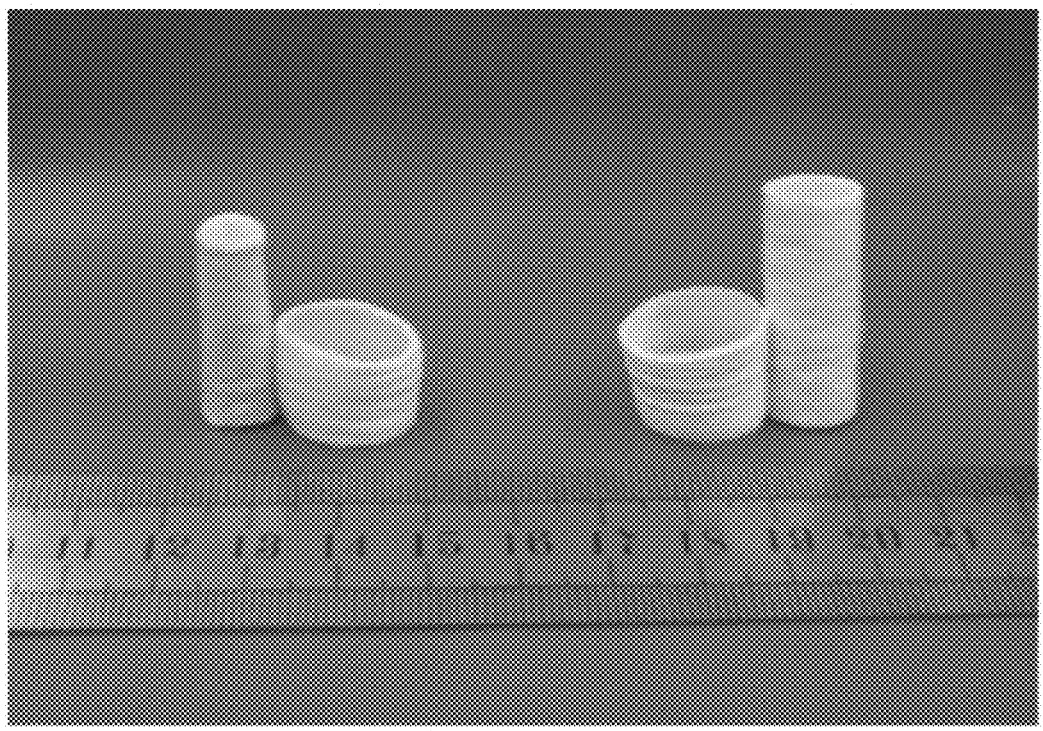
Figure 17A:
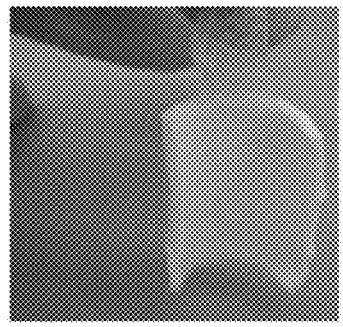
Figure 17B:
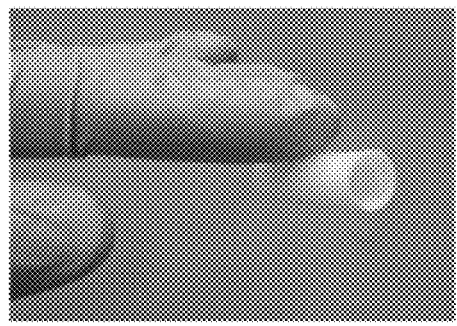
Figure 17C:
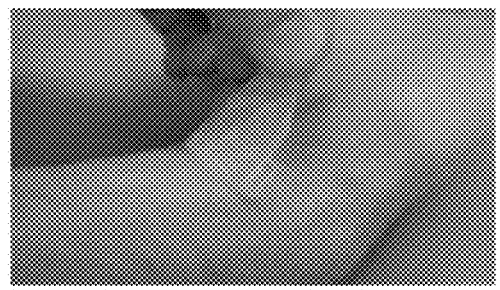
Figure 17D:
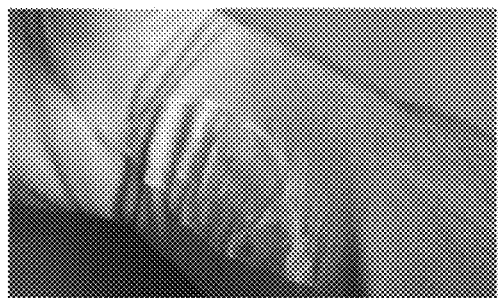
Figure 18:
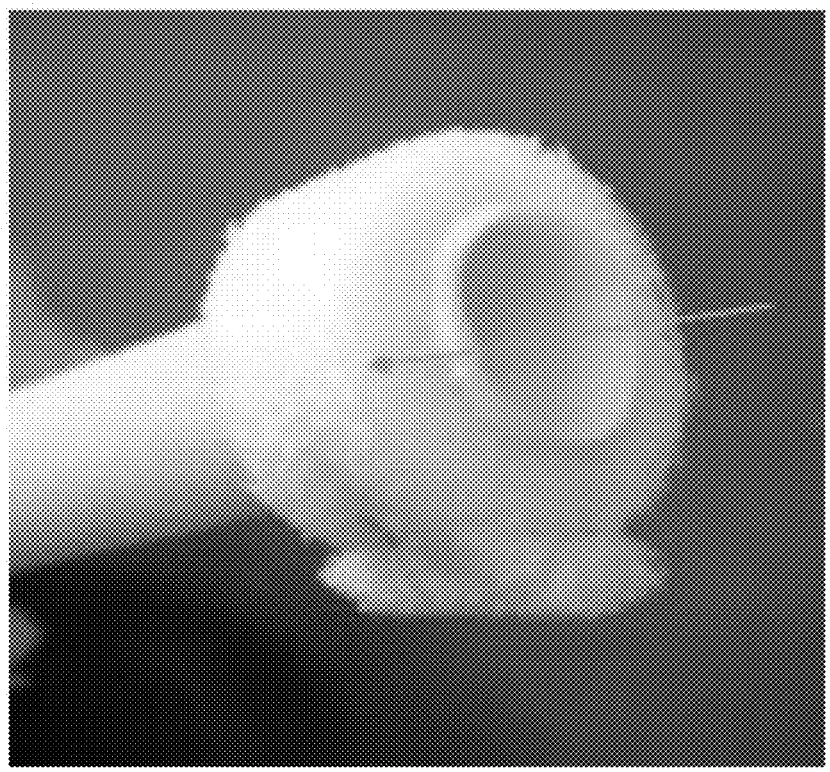
Figure 19A:
Figure 19B:
Figure 20:
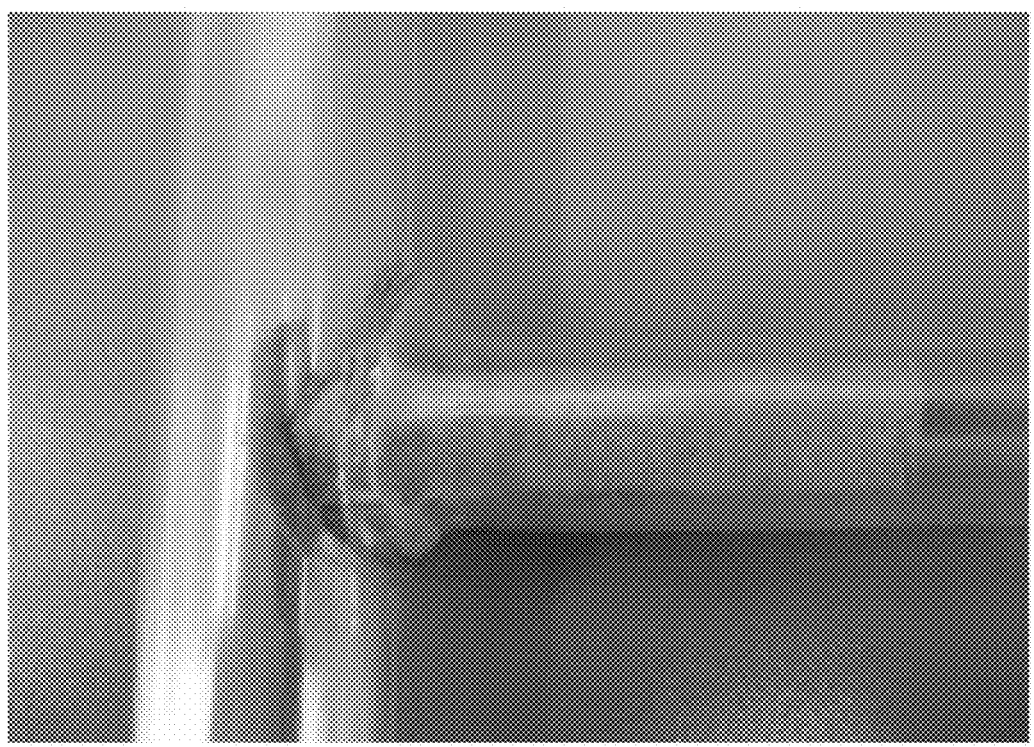
Figure 21A:
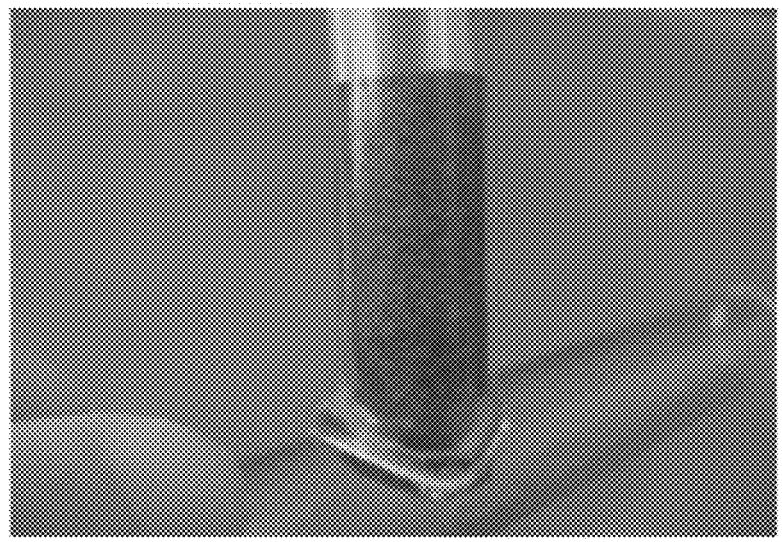
Figure 21B:
Figure 22A:
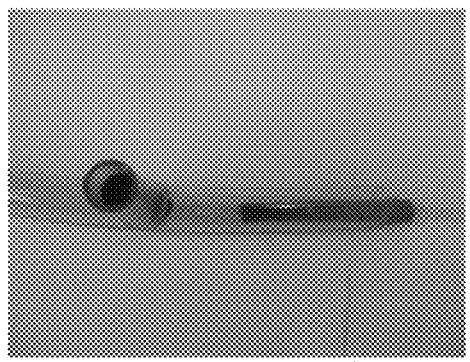
Figure 22B:
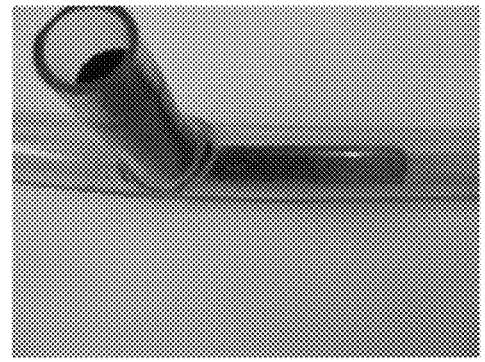
Figure 22C:
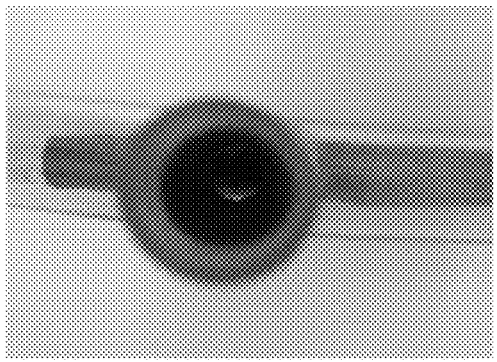
Figure 22D:
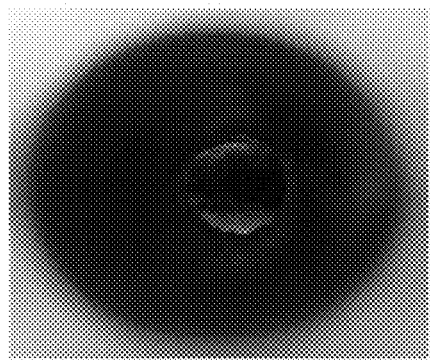
Figure 23A:
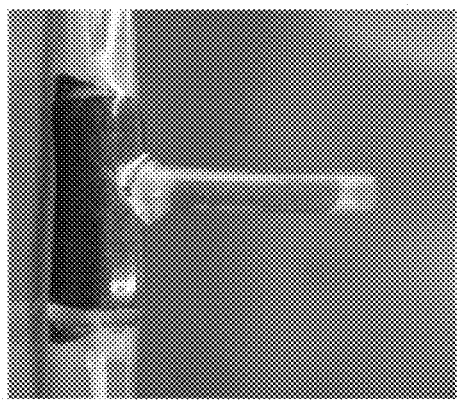
Figure 23B:
Figure 24:
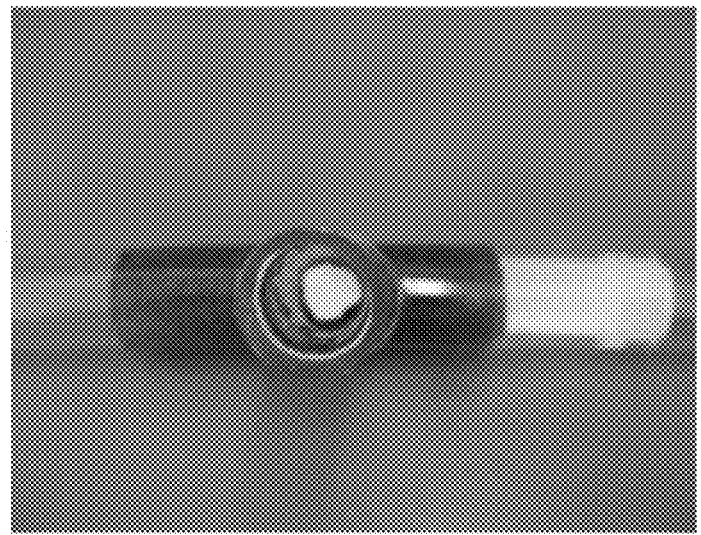
Figure 25A:
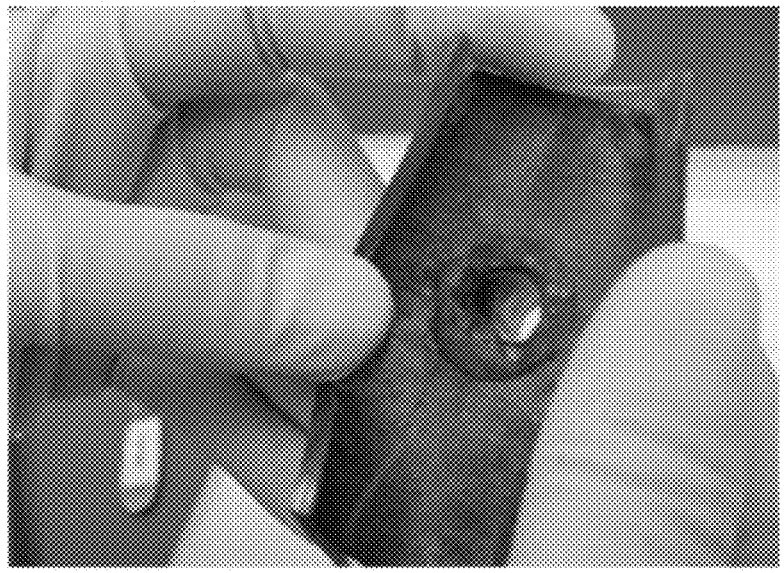
Figure 25B:
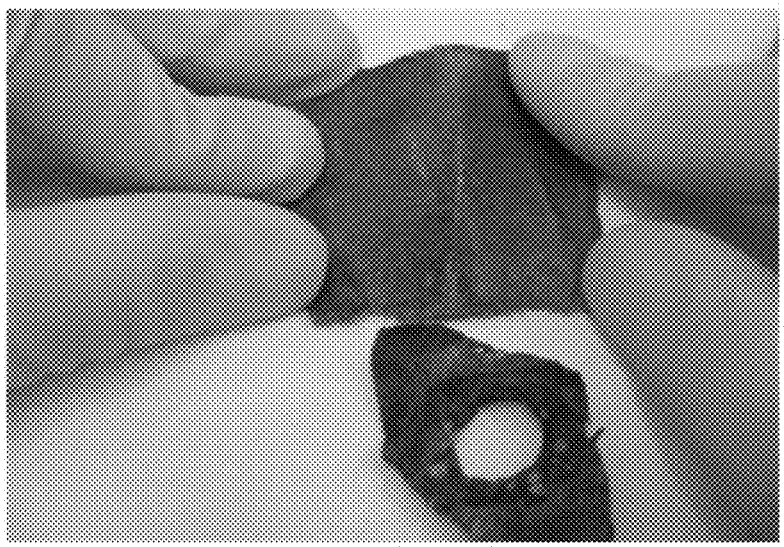
Figure 26A:
Figure 26B:
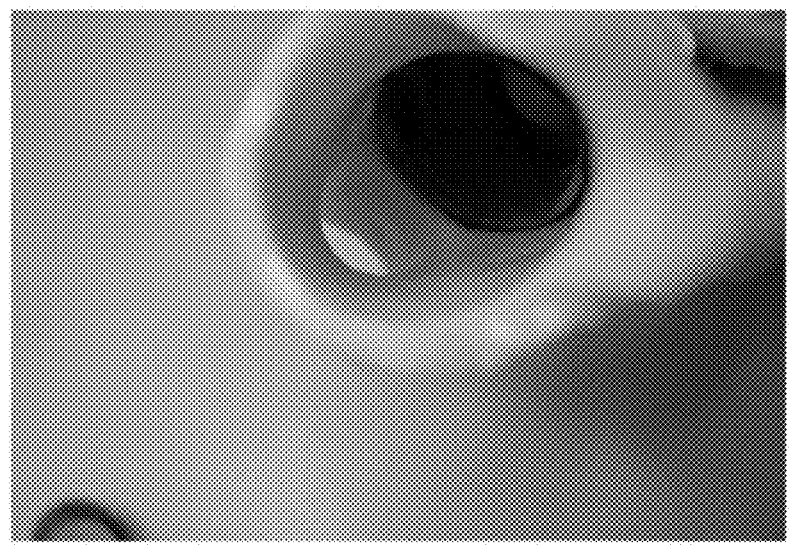
Figure 29:
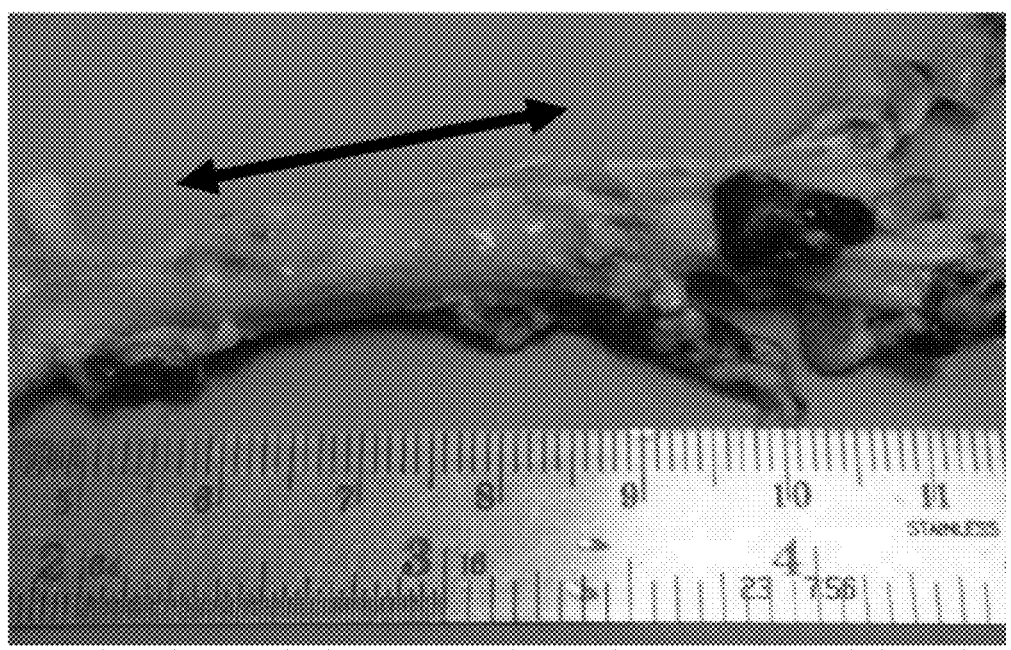
Figure 30:
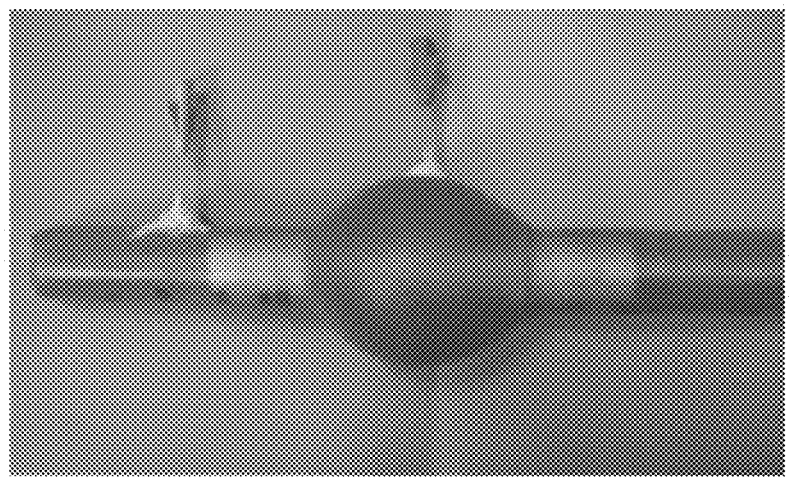
Figure 31:
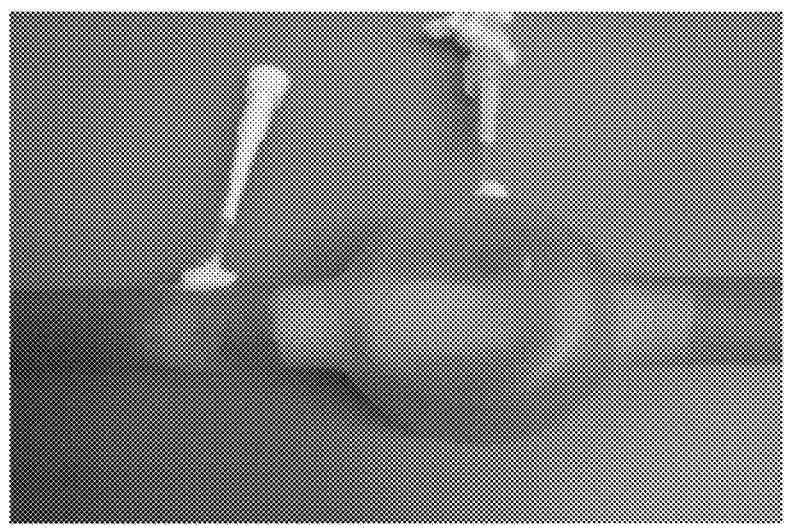
Figure 32:
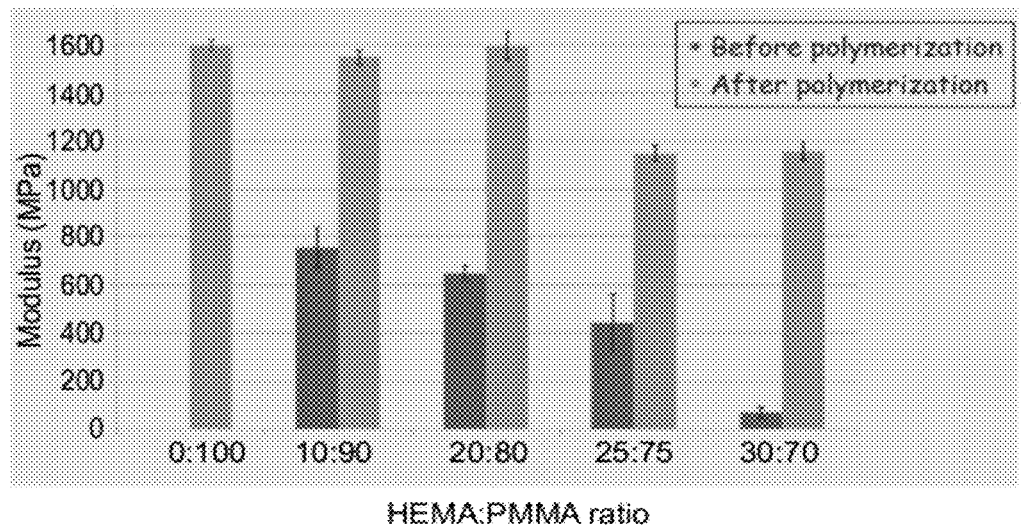
Figure 33:
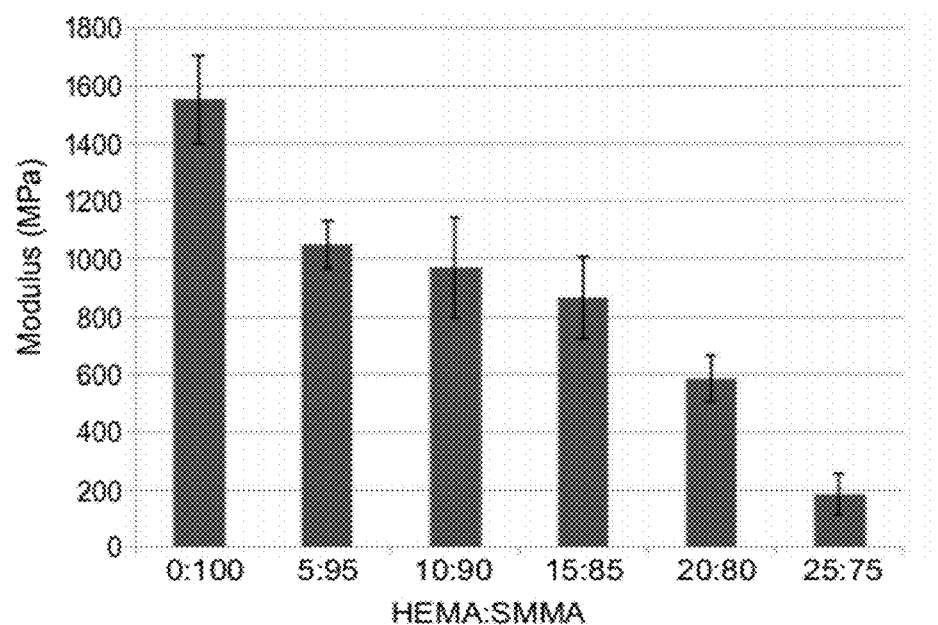
Figure 34:
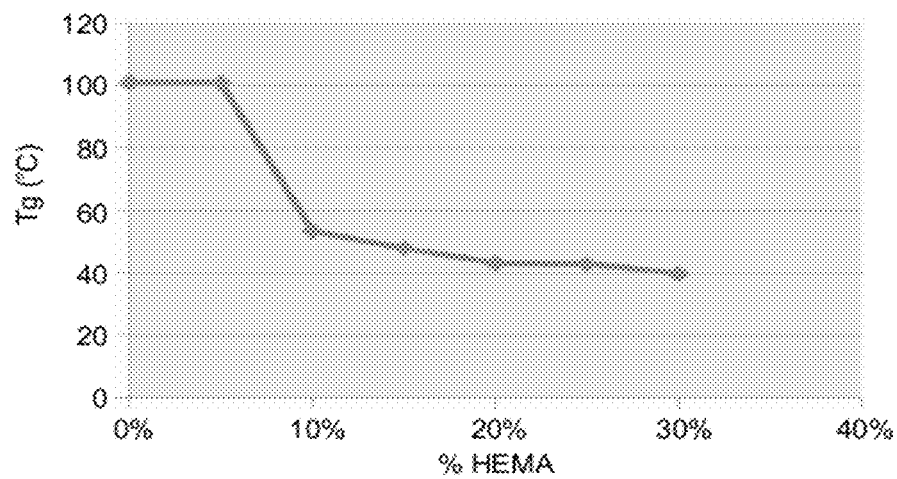
Figure 35:
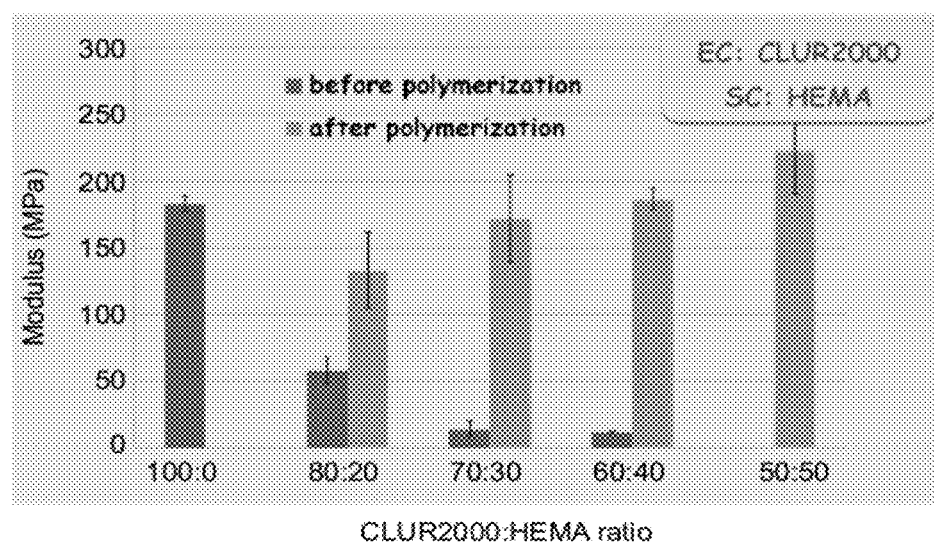
Figure 36:
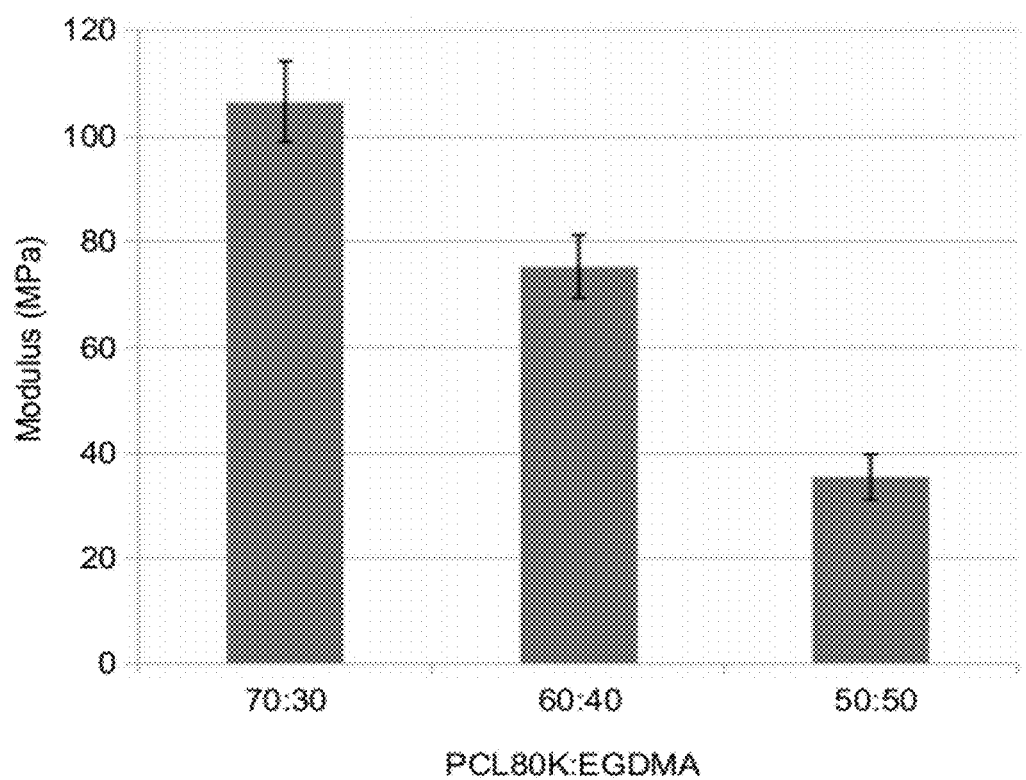
Figure 37:
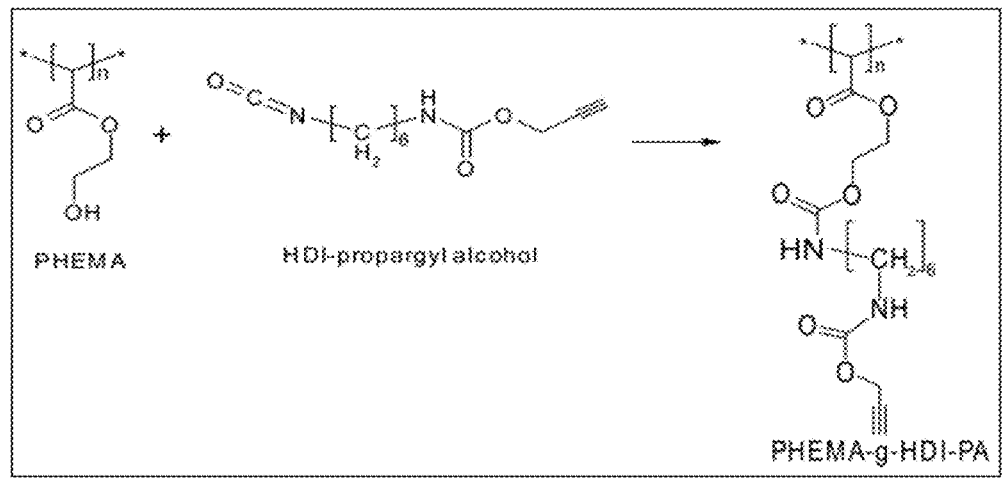
Figure 38:
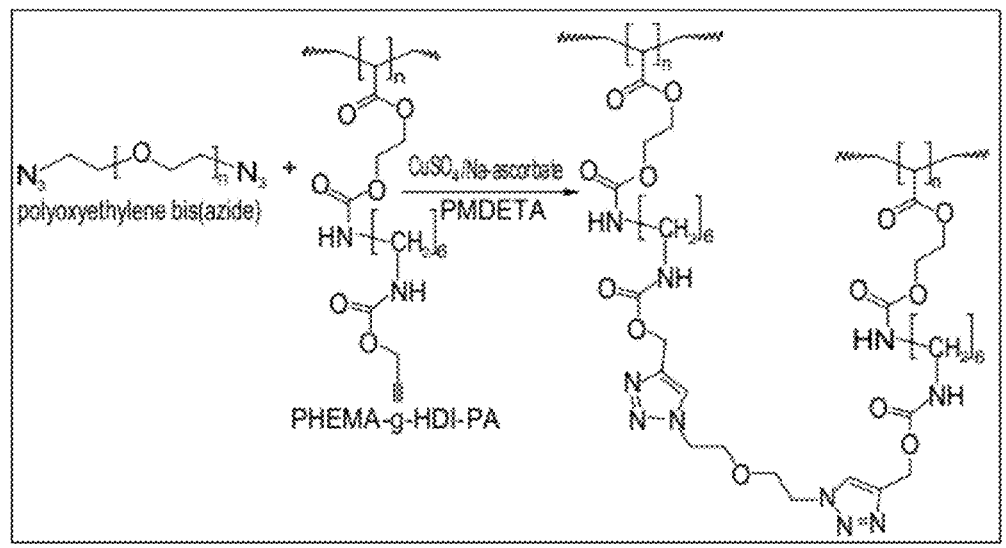
Figure 39:
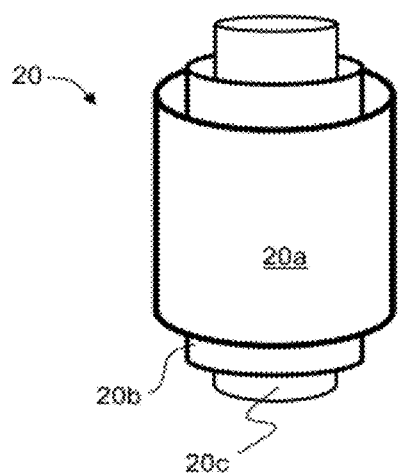
Figure 40A:
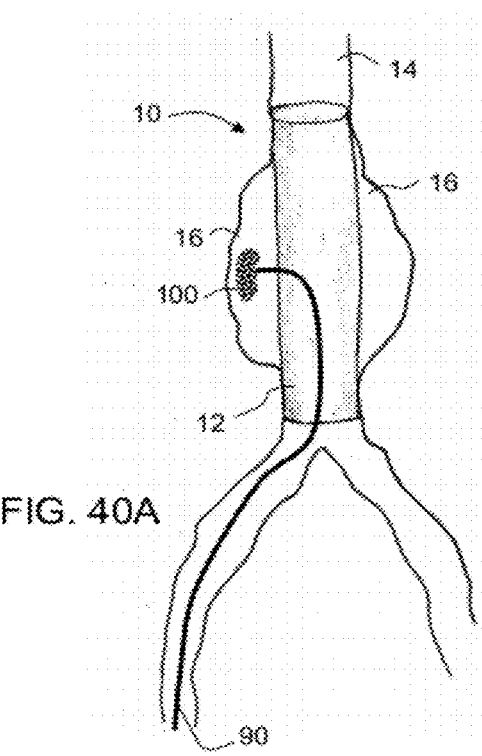
Figure 40B:
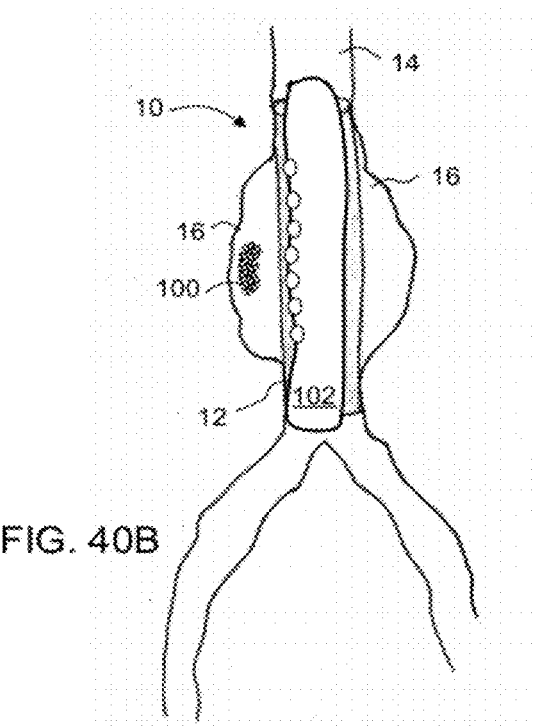

FIGS. 1A-B are schematic illustrations of a tubular structure, according to various exemplary embodiments of the present invention;

FIGS. 2A-E are schematic illustrations of a tubular structure which comprises a primary tubular member and two branch tubular members, according to some embodiments of the present invention;

FIG. 3 is a schematic illustration of a branched tubular structure in embodiments of the invention in which a wall or a part of a wall of one or more of the branch members is folded upon itself;

FIGS. 4A-B are schematic illustrations of a branched tubular structure in embodiments in which one or more of the branch members is weldable in situ;

FIG. 5 is a schematic illustration of a branched tubular structure in embodiments of the invention in which the structure comprises two parallel lumens;

FIG. 6 is a schematic illustration of a tubular structure in embodiments of the invention in which the structure comprises a lumen extending over a main host conduit and a secondary host conduit, but comprises an opening to form an outlet for allowing flow of body liquid to a third host conduit;

FIG. 7 is a schematic illustration of an embodiment of the invention in which a tubular structure is deployed at the upper part of the abdominal aorta, e.g., at vicinity of the renal arteries;

FIG. 8 is a schematic illustration of a device for delivering a branched tubular structure in embodiments of the invention in which more than one branch members of the tubular structure is delivered through the same conduit;

FIGS. 9A-B are schematic illustrations of a tubular structure in embodiments of the invention in which the structure comprises one or more compressible members;

FIG. 10 is a scheme depicting a synthesis of the exemplary polymer CLUR2000 by reacting a polycaprolactone (PCL2000) and hexamethylenediisocyanate (HDI);

FIG. 11 is a scheme depicting a synthesis of the exemplary polymer e-CLUR2000 by reacting a polycaprolactone (PCL2000), a polyethylene glycol (PEG2000) and hexamethylenediisocyanate (HDI);

FIGS. 12A-B are photographs showing tubular structures prepared from the exemplary polymers CLUR2000 (FIG. 12A) and e-CLUR2000 (FIG. 12B) by dip coating;

FIG. 13 is a drawing depicting an exemplary technique for producing polymeric devices according to some embodiments of the invention, comprising spraying an aerosol on a rotating mandrel;

FIG. 14 is a scanning electron micrograph showing fibers of the exemplary polymer e-CLUR2000 produced by air-spraying a solution of 5% e-CLUR2000 in chloroform onto a mandrel from a distance of 30 cm;

FIG. 15 is a graph showing the dependence of the diameter of e-CLUR2000 fibers on the concentration of e-CLUR2000 in a sprayed solution and on the distance from which the solution was sprayed;

FIG. 16 is a photograph showing tubular structures prepared from CLUR2000 before (narrow structures) and after (wide structures) expansion of the tubular structures (the edges of the tubular structures after expansion have been cut off, thereby shortening the structures);

FIGS. 17A-D are photographs showing the adhesiveness of layers of polyacrylic acid applied onto CLUR2000 films (visible in FIGS. 17A, 17C and 17D), which can support the weight of a cadaveric pig aorta section (FIG. 17A) and a polymeric structure (FIG. 17B) coated by polyacrylic acid;

FIG. 18 is a photograph showing a polymeric device comprising a polyurethane foam cuff (arrow points to the cuff);

FIGS. 19A-B are photographs of an exemplary endograft member prepared from CLUR2000, for constructing a branched endograft in situ;

FIG. 20 is a photograph showing the insertion of the endograft member shown in FIGS. 19A and 19B into an in vitro model of an aorta-renal branch;

FIGS. 21A-B are photographs of the endograft member shown in FIG. 20 after the endograft member has been expanded by a balloon;

FIGS. 22A-D are photographs showing the gradual alignment of a primary endograft member (with red dots) with the branch endograft member shown in FIGS. 21A-B in an in vitro model of an aorta-renal branch, until the circle of red dots on the primary member is in alignment with the branch member;

FIGS. 23A-B are photographs of the endograft members shown in FIGS. 22A-22D after the primary endograft member has been expanded by a balloon;

FIG. 24 is a photograph showing an exemplary branched endograft generated by forming a hole in the wall of the primary endograft member shown in FIG. 23B;

FIGS. 25A-B are photographs of the branched endograft shown in FIG. 24 following dissection, which show the welded area where the primary endograft member and branch endograft member are in contact (FIG. 25A), and a smooth inner surface of the tubular structures (FIG. 25B);

FIGS. 26A-B are photographs showing an exemplary endograft according to some embodiments of the invention being expanded in a cadaveric pig aorta section by inflation of a balloon with warm water (FIG. 26A) and a view of the endograft in the aorta from the opposite side (FIG. 26B);

FIG. 27 is a photograph showing an exemplary endograft mounted on a balloon for deployment in vivo according to some embodiments of the invention;

FIG. 28A-F are images showing placement of the mounted endograft shown in FIG. 18 in an aorta of a live pig (FIG. 28A), gradual inflation of the balloon (FIGS. 28B-28D), deflation of the balloon (FIG. 28E) and after the balloon has been withdrawn (FIG. 28F);

FIG. 29 shows an explanted pig aorta with an implanted endograft (arrow indicates section which contains endograft);

FIG. 30 is a photograph of an in vitro model of an aneurysm with a device according to some embodiments of the invention deployed therein;

FIG. 31 is a photograph showing a vacuum applied to a model aneurysm (center) having a device according to some embodiments of the invention deployed therein;

FIG. 32 is a graph showing the modulus of films with various weight ratios of 2-hydroxyethyl methacrylate (HEMA) to polymethyl methacrylate (PMMA) both before and after polymerization of the HEMA;

FIG. 33 is a graph showing the modulus of films with various weight ratios of non-polymerized 2-hydroxyethyl methacrylate (HEMA) to poly(styrene-co-methyl methacrylate) (SMMA);

FIG. 34 is a graph showing the effect of HEMA concentration on the glass transition temperatures of SMMA;

FIG. 35 is a graph showing the modulus of films with various weight ratios of a 2-hydroxyethyl methacrylate (HEMA) smart component (SC) to a CLUR2000 expandable component (EC) both before and after polymerization of the HEMA;

FIG. 36 is a graph showing the modulus of films with various weight ratios of non-polymerized ethylene glycol dimethacrylate (EGDMA) to the polycaprolactone PCL80K;

FIG. 37 is a scheme depicting a synthesis of an exemplary polymer (PHEMA-g-HDI-PA) comprising alkyne groups, effected by reacting poly(2-hydroxyethyl methacrylate) (PHEMA) with a conjugate of hexamethylenediisocyanate (HDI) and propargyl alcohol (PA);

FIG. 38 is a scheme depicting an exemplary method of in situ preparation of a cross-linked polymeric material (depicted on right), effected by reacting an exemplary polymer (PHEMA-g-HDI-PA) comprising alkyne groups with polyoxyethylene bis(azide) via Cu(I) catalysis in the presence of N,N,N',N',N"-pentamethyldiethylenetriamine (PMDETA);

FIG. 39 is a schematic illustration of a tubular member formed of several sequential layer members, according to some exemplary embodiments of the present invention; and FIGS. 40A and 40B are schematic illustrations of embodiments of the invention in which a filling material is injected into an aneurismal sac.

DESCRIPTION OF SPECIFIC EMBODIMENTS OF THE INVENTION

The present invention, in some embodiments thereof, relates to a polymeric device, and more particularly, but not exclusively, to a polymeric device useful for the treatment of an aneurysm and to polymeric systems useful for forming such a device.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Embodiments of the present invention relate to devices, polymeric systems and methods that perform in situ generation of a tubular structure in a body vessel. The devices, methods and systems described herein are suitable for lining a body vessel, and are therefore particularly useful for treating an aneurysm in a subject in need thereof, and in treating abdominal aortic aneurysms (AAA) in particular.

The devices, systems and methods described herein result in isolation of the weak aneurysmal arterial wall from the aortic blood stream, which immediately minimizes the risk of life-threatening internal bleeding due to sudden rupture of the aneurysm; and in restoration of the artery's cylindrical luminal geometry distorted by the vessel's deformation. The formed tubular structure attaches tightly and firmly to the normal aortic lumen, thus preventing its dislodgment from its position and also avoiding the occurrence of endoleaks.

The tubular structure comprises a polymeric substance which is soft when needed to facilitate expansion of the structure, and stiff when needed to retain an expanded state thereafter. The dimensions of the tubular structure are therefore highly controllable.

In addition, the relatively simple polymeric composition is advantageous in that the structure does not need to be assembled from various small components. Consequently, the risk of leaks at an interface between components of the device is greatly reduced, and the cost and difficulty of preparing such a device is not particularly high. In addition, the device does not rely on materials such as fabrics which are relatively likely to leak.

According to an aspect of some embodiments of the present invention there is provided a medical device comprising a non-metallic expandable tubular structure, the tubular structure being implantable in a body vessel and being made, at least in part, from a polymeric system characterized by a stiffness which changes upon stimulation under physiological conditions, such that said tubular structure is capable of expanding, becoming stiffer and retaining an expanded state thereafter.

As used herein, the phrase "body vessel" refers to a tubular part of a body, for conveying a body fluid.

According to some embodiments, the body vessel is a blood vessel.

As used herein, the phrase "physiological conditions" describes any physical or chemical parameter that characterizes a physiological environment. These include, but are not limited to, an aqueous medium (e.g., in a body vessel such as a blood vessel), a temperature of 37±5° C., pH of 6.5-7.5, and a presence of enzymes (e.g., hydrolases, esterases, amidases, etc.).

As further defined hereinbelow, the term "stiffness" is correlated with the modulus of elasticity of a material, such that an increase or decrease of a given percentage (e.g., 20%) in a stiffness of a material can be measured as an increase or decrease of such a percentage in the modulus of elasticity. The modulus of elasticity may be determined by standard techniques known in the art.

The term "changes" encompasses both a decrease and an increase in the stiffness of the polymeric system. Preferably, an increase in the stiffness of the polymeric system is effected upon the described stimulation.

As used herein, the term "stimulation" refers to an action and/or conditions that induce a change in stiffness. The stimulation may be an external stimulation such as an active procedure performed on the polymeric system (e.g., a procedure which provides a change in stiffness "on command"). The stimulation may also be intrinsic, such as passive exposure of the polymeric system to surrounding conditions (e.g., physiological conditions). The stimulation may alter a stiffness due to physical processes (e.g., changes of physical properties due to changes in temperature), chemical reactions (e.g., polymerization, cross-linking), and/or or a change in composition (e.g., by removal of a component from the system by diffusion or by incorporation of a component in the system by swelling). Various exemplary stimulations and the phenomena resulting therefrom are elaborated hereinafter.

According to some embodiments, the stiffness of the polymeric system is capable of changing in response to at least one external stimulation (e.g., an external stimulation as described herein).

In some embodiments, the stimulation which occurs under physiological conditions (external stimulation and/or intrinsic stimulation) allows a change in stiffness to be made in situ in a controlled and/or pre-determined manner.

According to optional embodiments, a stiffness of the polymeric system is increased by a stimulation, such that the stimulation is capable of causing the tubular structure to become stiffer after being expanded, thereby retaining an expanded state. Optionally, the increase of stiffness is an increase by at least 20%, optionally at least 50%, optionally at least 100%, optionally at least 300% and optionally at least 900% % of the stiffness.

According to optional embodiments, a stiffness of the polymeric system is decreased by a stimulation, such that the stimulation is capable of causing the tubular structure to become less stiff (to soften) prior to expansion, thereby becoming capable of expanding. Optionally, the decrease of stiffness is a decrease of at least 20%, optionally at least 40%, optionally at least 60%, optionally at least 80%, and optionally at least 90%.

It is to be appreciated that a stiffness of the polymeric system may be changed by more than one type of stimulation (e.g., types of stimulation as described herein). Optionally, at least one type of stimulation increases the stiffness and at least one type of stimulation decreases the stiffness, such that a stimulation is capable of rendering the tubular structure to become less stiff prior to being expanded, and another stimulation is capable of rendering the tubular structure stiffer after being expanded. Alternatively or additionally, two or more types of stimulation have a qualitatively similar effect on the stiffness (e.g., increasing the stiffness or decreasing the stiffness).

In some embodiments of the invention, if more than one stimulation are effected, the last stimulation performed increases the stiffness of the polymeric system. If a single stimulation is effected, it is performed so as to increase the stiffness of the polymeric system while it is at an expanded state.

The following describes exemplary medical devices according to some embodiments of the present invention.

Referring now to the drawings, FIGS. 1A-B illustrate a medical device 10, according to various exemplary embodiments of the present invention. Device 10 comprises an expandable tubular structure 12, which is preferably, but not necessarily, non-metallic. Structure 12 is preferably implantable in a vessel or conduit 14 of a body liquid, such as, but not limited to, a blood vessel, a urinary tract, a semen conduit, a colon, a bile duct, and the like. In the representative illustrations of FIGS. 1A-B, which are not to be considered as limiting, structure 12 is shown implanted in a lumen of a blood vessel, e.g., the abdominal aorta. When an aneurysm 16 is formed at the wall of the abdominal aorta, structure 12 can be used to isolate, at least partially, but preferably completely, the aneurysmal wall from the blood flow.

While the embodiments below are described with a particular emphasis on aneurysm in the abdominal aorta, it is to be understood that more detailed reference to aneurysms and the abdominal aorta is not to be interpreted as limiting the scope of the invention in any way.

In various exemplary embodiments of the invention structure 12 is made, at least in part, from a polymeric system. The polymeric system is preferably configured for changing the stiffness of structure 12 upon stimulation, as will be described in detail hereinbelow.

The term "stiffness" as used herein represents the degree to which an object resists to strain due to application of external force on this object. A suitable measure for characterizing the stiffness structure 12 is the modulus of elasticity of the polymeric system. When the modulus of elasticity is increased, the polymeric system is said to undergo stiffening, and when the modulus of elasticity is decreased, the polymeric system is said to undergo softening.

The stimulation allows structure 12 to be expanded from a collapsed state to an expanded state and retains its expanded state thereafter, in a manner that will now be explained.

In some embodiments of the present invention, the stimulation reduces the modulus of elasticity, namely the polymeric system undergoes softening during stimulation. In these embodiments, structure 12 is expanded during the time period at which the polymeric system is stimulated. Thereafter, or shortly before the expansion is completed, the stimulation is terminated. As a result, the modulus of elasticity increases, the polymeric system undergoes stiffening, and structure 12 becomes stiffer hence retains its expanded state.

In some embodiments of the present invention, the stimulation increases the modulus of elasticity, namely the polymeric system undergoes stiffening during stimulation. In these embodiments, structure 12 is expanded before the stimulation is activated. Thereafter, the stimulation is activated to increase the stiffness, the polymeric system undergoes stiffening, and structure 12 becomes stiffer hence retains its expanded state.

Also contemplated are embodiments in which the polymeric system is responsive to more than one type of stimulations. For example, a first type of stimulation reduces the modulus of elasticity, and a second type of stimulation increases the modulus of elasticity. In these embodiments, structure 12 is expanded during the time period at which the first type of stimulation is applied. Thereafter, or shortly before the expansion is completed, the second type of stimulation is applied such that the polymeric system undergoes stiffening, and structure 12 becomes stiffer.

The dimensions of structure 12 are larger in its expanded state than in its collapsed state. In its collapsed state, the dimensions are selected to allow the physician to conveniently deliver structure 12 to its deployment site (e.g., near aneurysm 16), preferably via a minimally invasive procedure. In the expanded state, the dimensions are such that its diameter matches or is slightly larger than the internal diameter of conduit 14. FIG. 1A shows structure 12 in its collapsed state and FIG. 1B shows structure 12 in its expanded state.

The present inventors contemplate many types of stimulations. In some embodiments of the present invention the stimulation comprises thermal stimulation. In these embodiments, the polymeric system preferably comprises a thermoplastic substance which undergoes softening at elevated temperatures (e.g., above 45° C., preferably from about 45° C. to about 60° C.) and hardening at lower temperatures (e.g., at physiological temperature of about 37° C.), as is further described hereinunder. In some embodiments of the present invention the softening of the thermoplastic polymer is characterized by a change of at least X % in its stiffness, where X equals 20 or 30 or 40 or 50 or more.

In some embodiments, the stimulation comprises mechanical stimulation. For example, the stimulation can include application of stress such as to induce a change in the strain of structure 12. In these embodiments, the polymeric system can be a strain rate sensitive polymeric system.

The term "strain sensitive polymeric system" as used herein refers to a polymeric system for which the modulus of elasticity at one strain is different from the modulus of elasticity at another strain.

The term "strain rate sensitive polymeric system" as used herein refers to a polymeric system which is characterized by a first modulus of elasticity under a normal load, and a second modulus of elasticity (different from the first modulus of elasticity) under a sufficiently high strain rate, e.g., when a polymeric material therein is being swollen.

Also contemplated is stimulation by light or ultrasound radiation, in which case the polymeric system comprises optically sensitive material(s) or ultrasound sensitive material(s), such as an optically sensitive polymeric system or an ultrasound sensitive polymeric system.

As used herein, "stimulation by light" and "optical stimulation" refer to irradiation by light at any wavelength, including the ultraviolet, visible and infrared ranges.

The term "optically sensitive polymeric system" as used herein refers to a polymeric system for which the modulus of elasticity is changed, preferably increases, when the polymeric system is exposed to optical radiation. An example of an optically sensitive polymeric system suitable for the present embodiments comprises a polymer that is cured when exposed to optical radiation. Additional examples are systems composed of one or more polymeric materials and/or of a polymeric material and a "smart" component, which interact when exposed to optical radiation.

The term "ultrasound sensitive polymeric system" as used herein refers to a polymeric system for which the modulus of elasticity is changed, preferably increases, when the polymeric system is exposed to ultrasound radiation.

Additionally contemplated is electrical stimulation in which case the polymeric system is preferably an electrically sensitive polymeric system.

The term "electrically sensitive polymeric system" as used herein, refers to a polymeric system for which the modulus of elasticity is changed, preferably increases, when a voltage is applied thereto.

Further contemplated is chemical stimulation, in which case the polymeric system for which the modulus of elasticity is changed, preferably increases, upon chemical reaction(s). The chemical stimulation can involve an addition of a chemical substance to the polymeric system or a chemical reaction that takes place when the polymeric system is exposed to e.g., aqueous media, change in pH, enzymes, catalytic substances, etc.

For example, a polymeric system is preferably responsive to a catalytic substance (e.g., an enzyme) such that its modulus is changed, preferably increases, following a reaction between one or more components in the polymeric system and the catalytic substance.

Also contemplated are embodiments in which structure 12 is made or partially made from a polymeric system that absorbs a controlled amount of water when exposed to the physiological environment, such that its stiffness is decreased. Following the expansion, a subsequent phenomenon takes place to increase the stiffness to the desired final level, as explained in detail hereinunder.

Thus, the structure of the present embodiments can undergo changes in its stiffness via different scenarios. In one scenario, the polymeric system has the required final mechanical properties which are temporarily changed in vivo to allow navigation in the body vessel, and expansion at the desired site. Specifically in this scenario, the stiffness of an essentially suitably stiff structure is reduced by an appropriate stimulus, to allow navigation and expansion. Once the structure is expanded at the desired site, its original stiffness is restored by a second stimulus which may be artificial or provided by the physiological environment itself. In another scenario, the structure has the required initial mechanical properties, namely sufficient flexibility to allow navigation in the body vessel, and expansion at the desired site. Once the structure is expanded at the desired site, its stiffness is increased by a stimulus which is typically artificial but may be, in some embodiments, provided by the physiological environment itself.

Structure 12 is typically expanded by means of an inflatable balloon which is temporarily introduced into the lumen of structure 12. The balloon can be caused to inflate by introducing an inflating fluid (liquid or gas) into the balloon so as to increase its internal pressure. In some embodiments of the present invention the inflating fluid is a physiologically acceptable liquid such as a saline solution, as known in the art. The inflating fluid can be at the temperature of the body or a different temperature, as desired. For example, when the polymeric system is responsive to thermal stimulus, the temperature of the inflating fluid can be selected such as to induce the thermal stimulus (e.g., apply heat to structure 12) while the balloon is in the process of inflating.

In various exemplary embodiments of the invention the polymeric system is capable of contracting upon stimulation and retaining its contracted state thereafter. These embodiments are particularly useful when structure 12 is delivered to the deployment site during a minimally invasive guided procedure. In such procedure, once structure 12 is expanded at the site, the physician may decide to reposition structure 12, e.g., to achieve a better sealing or to better support of the damaged conduit or to avoid blocking a branch conduit. The physician can then apply the stimulation to which the polymeric material is sensitive so as to induce temporary contraction of structure 12 to a dimension which is sufficiently smaller than the dimension of conduit 14 (see, e.g., FIG. 1A). While structure 12 is at its suitably contracted state, the physician can conveniently maneuver structure 12 to its new position. Thereafter, structure 12 is expanded as further detailed hereinabove.

FIGS. 2A-E, 3, 4A-B, 5, 7 and 8 are schematic illustrations of device 10 in embodiments of the invention in which tubular structure 12 is a branched tubular structure.

In the schematic illustration of FIGS. 2A-E, structure 12 comprises a primary tubular member 20, a first branch tubular member 22 and a second branch tubular member 24. Primary member 20 preferably has a characteristic diameter which is larger than the characteristic diameter of each of members 22 and 24. For example, when structure 12 is deployed in the lower part of the abdominal aorta, the outer diameter of member 20 can match the inner diameter of the aorta, and the outer diameters of members 22 and 24 can match the inner diameters of the iliac arteries 26 and 28, respectively. The matching between the diameters of members 20, 22 and 24 and the diameters of the conduits in which they are deployed can be ensured by providing members 20, 22 and 24 with a sufficiently small initial diameter and expanding them in situ, as further detailed hereinabove.

Each of branch members 22 and 24 can serve for supporting and/or sealing of the hosting conduit or as a fixation element for fixating structure 12 in its deployment site. The configuration illustrated in FIGS. 2A-E are particularly useful for supporting the abdominal aorta having an aneurysm near the aortic bifurcation or an aneurysm that extends into one or both common iliac arteries. When the aneurysm is near the aortic bifurcation but does not extend into the common iliac arteries, both branch members 22 and 24 may serve as fixation elements and can be made relatively short (e.g., 2-3 centimeters).

Figure 2A:
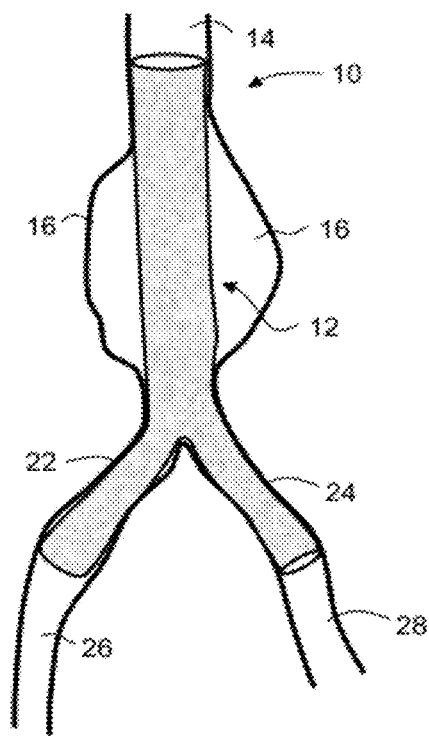

When the aneurysm extends into both common iliac arteries, the branch members that are deployed in the aneurismal iliac arteries serve for supporting and/or sealing of these arteries. This embodiments is schematically illustrated in FIG. 2A.

Figure 2B:
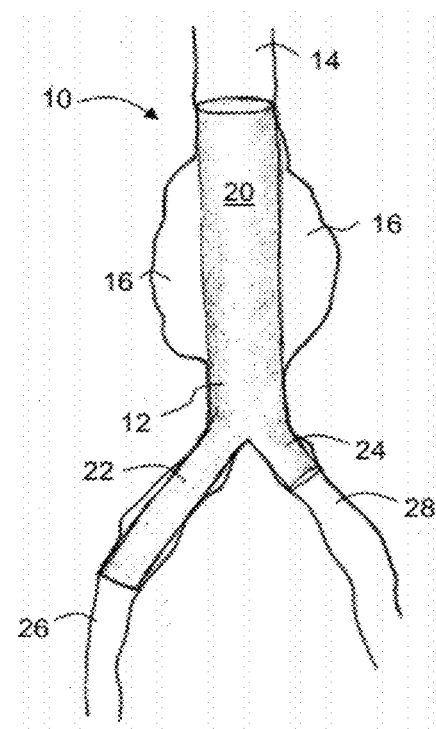
Figure 2C:
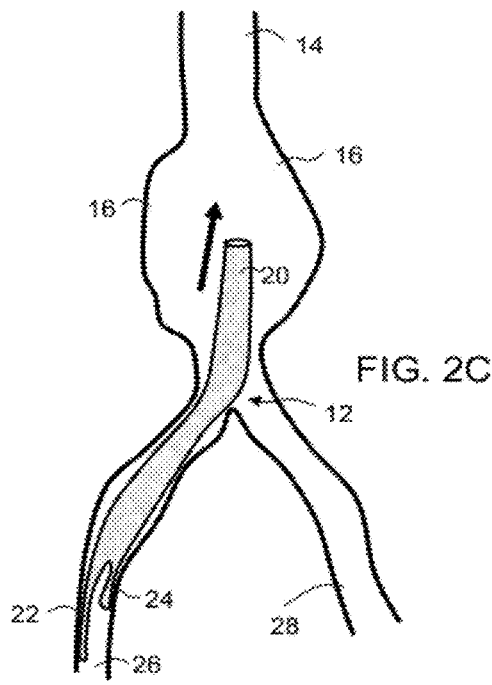

When the aneurysm extends into one of the common iliac arteries, the branch member that is deployed in the aneurismal iliac artery serves for supporting and/or sealing of that artery, and the other branch member serves as a fixation element. In these embodiments, the branch member that is deployed in the aneurismal artery is preferably longer that the branch member that is deployed in the healthy artery. This embodiments is schematically illustrated in FIG. 2B.

Figure 2D:
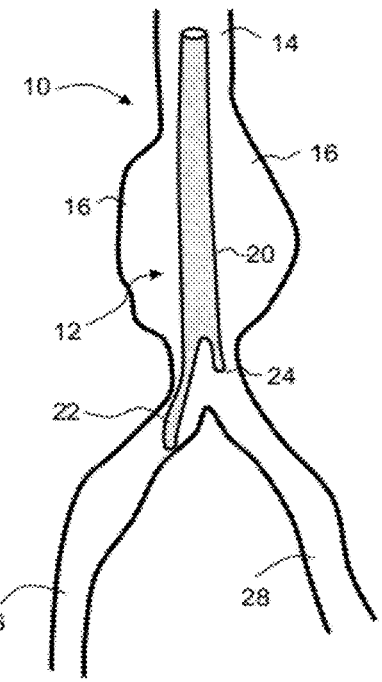
Figure 2E:
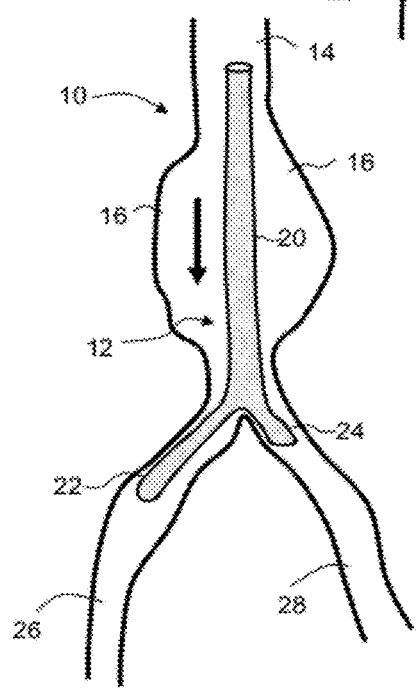

A suitable procedure for deploying branched structure 12 according to some embodiments of the present invention is as follows. Structure 12 is firstly delivered through one of the common iliac arteries, for example, the right common iliac artery 26 (see FIG. 2C) into the abdominal aorta until at least one of the branch members (e.g., member 24) passes the aortic bifurcation (FIG. 2D). Structure 12 is then pulled back (FIG. 2E) until each of the branch members resides one of the common iliac arteries. The forward and backward delivery of structure 12 can be performed via a catheter (not shown) as known in the art. Once structure 12 is in its position, members 20, 22 and 24 are expanded and fixated at their respective sites (FIGS. 2A and 2B).

FIG. 3 is a schematic illustration of structure 12 in embodiments in which a wall of one or more of the branch members is folded upon itself. In the present illustration, member 24 is folded upon itself to form an inner tubular wall 32 within member 24. Once structure 12 is delivered to the appropriate site, the folded part of member 24 can be unfolded in situ as indicated by arrow 34. Thereafter, the different members of structure 12, e.g., namely the primary tubular member and the branch members, can be expanded as further detailed hereinabove.

The folded configuration facilitates the maneuvering of structure 12 within host conduit 14, since the length of member 24 while being delivered to the deployment site is significantly shorter than its deployment length. Thus, when structure 12 is delivered, e.g., according to the procedure shown in FIGS. 2C-E, it is sufficient to pull structure 12 back immediately once the folded member passes the aortic bifurcation, since the unfolding can be done at the respective secondary conduit (e.g., iliac artery).

FIGS. 4A-B are schematic illustrations of structure 12 in embodiments in which one or more of the branch members is weldable in situ. For example, structure 12 can be provided as a kit which contains members 20 and 22 as a single unit (e.g., with member 22 as an integral extension of member 20), and member 24 as a separate unit (FIG. 4A) which can be welded to a receiving region 40 on member 22 or 20 in situ. One end of member 24 can be provided with a generally annular element 42 sizewise and shapewise compatible with receiving region 40 for facilitating the welding. Members 20 and 22 can be delivered through one of the iliac arteries (the right iliac artery in the present illustration), and member 24 can be delivered through the other iliac artery (the left iliac artery in the present illustration). Once all members are in place, they are welded in situ (FIG. 4B). The welding can be performed, for example, by applying heat and/or a pressure of at least 2 atmospheres.

The term "welding" as used herein refers to a process in which the respective members are melted, at least partially, at the point of joining between the two members, wherein the combined pool of molten material subsequently cools to form one continuous mass of material such that both members are integral parts of each other.

In some embodiments of the present invention an artificial foreign filler material such as gluing agent or the like is used in the welding process. The preferred embodiment, however, is welding in the absence of additional artificial foreign material.

Member 24 can be welded to members 20 and 22 after positioning element 42 against the luminal surface of members 20 and 22 at receiving region 40, with element 42 residing inside members 20 and 22. Alternatively, the welding between members 20 and 22 and member 24 can be performed with element 42 being placed against the external surface of members 20 and 22 at receiving region 40.

Fluid intercommunication between the lumens of the various members is established by an opening that can be formed in situ at receiving region 40 using a suitable puncturing device, such as tapered tip or the like. Alternatively, receiving region 40 can be provided with a preformed opening (not shown, see, for example, 62 in FIG. 6). When the opening is formed in situ, the puncturing is preferably executed after member 24 contacts receiving region 40. The formation of the opening is typically accompanied by formation of one or more peripheral flaps (not show in FIG. 4, see 64 in FIG. 6). These flaps are preferably welded to the inner wall of one of the members, preferably, but not necessarily member 24. Such welding can enhance sealing at the interface between member 24 and member 20.

The welding in any of the above embodiments can be achieved by any suitable welding device that is adapted to be introduced into the body vessel. Such device typically generates heat sufficiently to melt or partially melt the polymeric system at the point of joining between the two members. Optionally and preferably the heating is accompanied with application of pressure at the joining point. In some embodiments of the present invention the inflatable balloon serves as a welding device. In these embodiments, the balloon is preferably filled with an inflating fluid at elevated temperatures (e.g., from about 50° C. to about 70° C.) so as to generate sufficient heat at region 40. The balloon can also be configured to protrude and extend into the branch members so as to weld the peripheral flaps to the respective wall.

FIG. 5 is a schematic illustration of structure 12 in embodiments of the invention in which structures 12 comprises two parallel lumens 50 and 52. Lumens 50 and 52 can be provided as a kit which contains two tubular members 54 and 56 each defining a single lumen therein. Member 54 can be delivered through one of the iliac arteries (the right iliac artery in the present illustration), and member 56 can be delivered through the other iliac artery (the left iliac artery in the present illustration). Once both members are in place, they are welded in situ, as further detailed hereinabove.

FIG. 6 is a schematic illustration of structure 12 in embodiments in which structures 12 comprises a lumen extending over a main host conduit 14 (e.g., the abdominal aorta) and a secondary host conduit 26 (e.g., the right iliac artery), but comprises an opening 62 to form an outlet for allowing flow of body liquid to a third host conduit 28 (e.g., the left iliac artery). Opening 62 can be formed in the wall of structure 12 in situ, for example, following the expanding of structure 12 at the deployment location. Preferably, opening 62 is formed such as to create outwardly extending peripheral flaps 64.

It is recognized that device 10 can be deployed also in other locations along the aorta. For example, in some embodiments of the present invention device 10 is deployed to support and providing sealing at the upper part of the abdominal aorta or the thoracic aorta, e.g., at vicinity of the renal arteries. These embodiments are illustrated in FIG. 7. Shown in FIG. 7 is aorta 70, common iliac arteries 72 and 74, and renal arteries 76 and 78. Aorta 70 has an aneurism 80 between the iliac arteries and the renal arteries. Structure 12 is deployed such that it extends both below and above renal arteries 76 and 78. To allow passage of blood into renal arteries 76 and 78, structure 12 may include openings at the connection between the renal arteries and the aorta. These openings are not shown, but one of ordinary skills in the art, provided with the details described herein would know how to add openings to FIG. 7. Generally, these openings can be similar to opening 62 described above.

In some embodiments, structure 12 comprises a primary member 20 and one or more tubular branch members 82, 84 adapted for being introduced into renal arteries 76 and 78. Optionally and preferably, members 82 and 84 are provided separately from member 20 and are welded to member 20 in situ as further detailed hereinabove. In these embodiments, members 82 and/or 84 are preferably delivered into the respective renal arteries before member 20. Similarly to member 24 described above, one or more of members 82 and 84 can be provided with a generally annular element (not shown see 92 and 94 in FIG. 8) for facilitating and strengthening the welding. In some embodiments, structure 12 can comprise additional branch members 86 and 88 which can be adapted for being introduced into iliac arteries 72 and 74. Any of branch members 86 and 88 can be provided either separately from member 20, in which case the respective member is welded in situ, or as an integral extension of member 20, as further detailed hereinabove. Any of branch members 86 and 88 can be folded upon itself as further detailed hereinabove.

A supra-renally deployed structure is advantageous particularly in cases in which the landing areas available for fixation of the structure below the renal arteries are too short to allow secure fixation of the device. Some embodiments of the present invention allow providing firm attachment of the structure to the healthy aortic vessel above the renal arteries, while allowing continuous blood flow from the aorta into the renal arteries. Additionally, this embodiment prevents or reduces endoleaks along the structure, including the aortic-renal branching points. Furthermore, this embodiment also prevents migration of the structure.

Any of the tubular members of structure 12 can be provided as a single unit or as two or more tubular units, each constituted to form a layer of the respective member. Thus, a respective tubular member can be provided as a kit or sub-kit which includes several such tubular units. This embodiment is illustrated in FIG. 39, showing a tubular member (member 20 in the present non-limiting example) which is formed of several (3 in the present non-limiting example) sequential, preferably weldable, layer members, generally designated 20a, 20b and 20c, deployed one within the other in a multilayer relationship. For clarity of presentation, layer members 20a, 20b and 20c are shown as having different lengths however, this need not necessarily be the case, since, for some applications, it may be desired to have equal-length layer members. In some embodiments, the layer members are coaxial.

The individual layer members forming the tubular member can be delivered to the body vessel in a consecutive manner. Initially, all layer members can have a reduced diameter so as to allow maneuvering the layer member to the desired site. Once the first (outermost) layer member is at the desired site, it can be expanded to the expanded state as further detailed hereinabove. Subsequently, the next-to-outermost layer member is delivered to occupy the volume defined by the first layer. This layer is then expanded and creates a volume which the third layer member can occupy and so on. In various exemplary embodiments of the invention each layer member is welded to its adjacent layer member(s). The welding technique can be any of the techniques described above.

A suitable device for delivering structure 12 in embodiments in which more than one branch member and/or more than one layer member is delivered through the same conduit is illustrated in FIG. 8. Shown in FIG. 8 is a catheter 90 and three tubular members 20, 82 and 84 mounted serially on catheter 90. Although FIG. 8 illustrates members 20, 82 and 84, the skilled person would appreciate that other members, e.g., layer members 20a, 20b and 20c can additionally or alternatively be mounted on catheter 90. In use, the physician guides catheter 90 through the main conduit (e.g., aorta 80) to one of the secondary conduits, e.g., renal artery 76, and use catheter 90 to introduce member 82 into the respective conduit. Without extracting the catheter out of the body, and while the catheter is still in the main conduit, the physician then guide catheter 90 to another secondary conduit, e.g., renal artery 78, and use catheter 90 to introduce member 84 into that conduit. The physician can then use the same catheter to introduce member 20 into the main conduit.

FIGS. 9A-B are schematic illustrations of tubular structure 12 in embodiments of the invention in which structure 12 comprises an annular compressible member 96 such as a foam mounted on an end of tubular structure 12. Compressible member 96 serves for enhancing the fixation of tubular structure 12 in the host conduit and preventing or at least minimizing the risk of endoleaks. Said compressible member 96 can be annular but can also have other geometries. Any of the ends of structure 12 can include such annular compressible member. FIG. 9A illustrates structure 12 with a single compressible member, and FIG. 9B illustrates structure 12, once deployed in conduit 14, with two annular compressible members. It is appreciated that more than two compressible members can be used. For example, when structure 12 is a branched structure, each of the branch members can include a compressible member for improved fixation.

The present inventors also contemplate other fixation means. For example, in some embodiments, the outer wall of tubular structure is coated by, or modified to have on its surface, a bioadhesive or an adhesive-forming agent, and in some embodiments, the outer wall of the structure is modified to increase the adhesiveness of its outer wall.

The bioadhesive or the adhesive-forming agent can be a naturally-occurring substance or a synthetic substance.

As used herein, the term "bioadhesive" refers to an adhesive which facilitates adherence of an object to a biological tissue under physiological conditions. Examples include, without limitation, polyacrylic acid, tragacanth, poly(ethylene oxide), cellulose derivatives (e.g., methyl cellulose, hydroxypropyl methyl cellulose, methylethyl cellulose), alginates, karaya gum, soluble starch, gelatin, hyaluronic acid and poly(ethylene glycol). Polyacrylic acid is an exemplary bioadhesive.

As used herein, the phrase "adhesive-forming agent" refers to an agent which is not an adhesive material per se, but which forms an adhesive material (e.g., by polymerization). Suitable examples include cyanoacrylates such as methyl 2-cyanoacrylate, ethyl-2-cyanoacrylate, n-butyl cyanoacrylate and 2-octyl cyanoacrylate, as synthetic substances and a fibrin glue as a naturally-occurring substance.

An exemplary biodegradable cyanoacrylate-based adhesive which is suitable for use in the context of embodiments of the present invention is disclosed in WO 2010/026590.

In some embodiments, an outer wall of the tubular structure is optionally modified (e.g., by chemical reaction) so as to comprise hydrophilic functional groups, such as hydroxyl, thiol, nitro and charged functional groups (e.g., carboxylic acid, amine, sulfate, sulfonate, phosphate, phosphonate). Optionally, the hydrophilic groups are charged groups, and optionally negatively charged groups. In some embodiments, the functional groups are carboxylic acid groups.

Carboxylic acid groups may be introduced to a surface, for example, by plasma treatment with $CO_2$ gas.

According to optional embodiments, the device is configured so as to facilitate tissue engineering.

Optionally, the device is configured for tissue engineering by having a porosity on an outer surface which renders the device suitable as a scaffold for tissue regeneration, while still preventing the occurrence of endoleaks.

In one embodiment, the whole device is suitably porous, and includes an external non-porous skin, to prevent blood leakage. When the device is deployed and expanded, the porous wall of the device is compressed against the luminal wall of the blood vessel, generating a tight seal that prevents both endoleaks and migration. Simultaneously, in front of the aneurismal sac, the porous wall of the device retains its porosity, being able to function as a suitable three-dimensional scaffolding construct on which cells are able to grow, differentiate and generate new tissue.

In some embodiments of the invention, the device contains cells removed from a donor site prior to implantation of the device, or aim at regenerating tissue at the site of implantation, by the combined action of biomolecules and cells, in situ, and combinations thereof.

Additionally, tissue regeneration may optionally be promoted by incorporating cells, such as endothelial cells and smooth muscle cells, and/or bioactive molecules into the scaffold, such as growth factors (e.g. VEGF and PDGF), to induce enhanced vascularization.

The luminal surface of the device may optionally be rendered blood compatible following various strategies. For example, polyethylene glycol (PEG) chains can prevent protein adsorption and cell attachment. PEG is optionally covalently bound to the surface. Alternatively, RGD-containing oligopetide sequences are optionally covalently bound to the surface to accelerate endothelialization of the luminal surface of the device.

In order to reduce the likelihood of endoleaks, the device may further be configured to result in filling of the aneurismal sac, using various polymeric systems.

In some embodiments, the device is configured to allow releasing a filling material into the aneurismal sac. This embodiment is illustrated in FIGS. 40A and 40B. FIG. 40A illustrates an embodiment in which a catheter, which may be catheter 90 or an additional catheter, is introduced into the lumen of structure 12 and caused to puncture the wall of structure 12. The catheter comprises, or is in the form of, a conduit which releases filling material 100 into the aneurism 16. FIG. 40B illustrates an embodiment in which filling material 100 is delivered via a perforated balloon 102. In this embodiment, structure 12 is provided with one or more openings to allow filling material to penetrate the wall of structure 12 into aneurism 16. Once filling material 100 is spread in the aneurismal sac, the openings in the wall of structure 12 are sealed, typically by filling material 100 itself.

Alternatively, or additionally the wall of structure 12 can be made fibrous to allow a spontaneous self-sealing process caused by virtue of the elasticity of the fibers forming the wall. For example, structure 12 can be made multilayered with one or more layers, e.g., intermediate layers, that have self-sealing property to prevent leakage following piercing. Layers having a self-sealing property can be made from thin and randomly-oriented elastic fibers, with a relatively high porosity ranging. Preferably, such layers are relatively thick, e.g., forming more than 50% of the wall of structure 12. Other layers of structure 12 can be made less porous.

Upon puncturing, the puncturing catheter passes through the self-sealing layer, by forcing the fibers apart, hence no rupturing occurs. The rupturing is prevented due to the combination of high elasticity of the fibers, large number of voids and small number of bonds between the fibers. Once the puncturing catheter is extracted out of the wall, the original fibers web is reconstructed, partly due to the fiber elasticity and partly due to the pressure applied by the other layers.

Optionally, the filling material is a reverse thermo-responsive polymer, which then gels to a desired consistency.

Optionally, the reverse thermo-responsive polymers are also able to crosslink at the site, once having filled the sac and gelled at the site In some embodiments, the filling material can comprise polymerizable and/or crosslinkable precursors, typically oligomeric, which are released into the sac and which then polymerize and/or crosslink, generating a stable and suitably robust filling material.

The filler can be biodegradable or not, and may comprise also biological cells.

The tubular structure of the present embodiments can be fabricated in more than one way. In some embodiments of the present invention, a polymeric solution is deposited to form one or more tubular layers, e.g., on a rotating mandrel. The solution can be deposited by any conventional process, such as, but not limited to, a spinning process, a blowing process and the like. Contemplated spinning processes include, without limitation, wet spinning process, gel spinning process, dry spinning process, dispersion spinning process, reaction spinning process, tack spinning process, air spraying and electrospinning process. These spinning processes are described in the Background section above and can be found in many text books and patents, see, e.g., U.S. Pat. Nos. 3,737,508, 3,950,478, 3,996,321, 4,189,336, 4,402,900, 4,421,707, 4,431,602, 4,557,732, 4,643,657, 4,804,511, 5,002,474, 5,122,329, 5,387,387, 5,667,743, 6,248,273 and 6,252,031 the contents of which are hereby incorporated by reference. Representative examples of spinning processes in various preferred embodiments of the present invention are further detailed hereinunder.

In a blowing process, an extruder is used to melt the polymeric material and pump it into, for example, a tubular die. Air blown into the center of the tube causes the melt to expand in the radial direction. The melt in thus extended in both radial and down-stream direction. Alternatively, the polymeric material can be air sprayed onto a rotating mandrel.

Also contemplated is a process known as dip coating. In this process, a mold, typically cylindrical, can be dipped into the polymer solution, preferably at a constant velocity, to obtain a uniform coating on the mold.

Additionally contemplated is a an injection process in which a reciprocating or rotating screw both melts polymer pellets and provides the pressure required to inject the melt into a cold mold, which provides the structure with the tubular shape.

Additionally contemplated is the use of the filament winding technique.

The following describes exemplary polymeric systems suitable for use in the context of embodiments of the invention.

Generally stated, polymeric systems which are suitable for use in the context of embodiments of the present invention can be categorized into mono-component systems and multi-component (e.g., bi- or tri-component) systems. Suitable polymeric systems can alternatively be categorized as systems employing known substances and as systems employing novel substances or novel combinations of substances. Suitable polymeric systems can further alternatively be categorized as systems employing thermoplastic polymers, which are responsive to a thermal stimulation, and "smart" systems, which undergo a physical phenomenon and/or chemical reaction upon stimulation, as is further detailed hereinunder. Suitable polymeric systems can alternatively be categorized as systems having the mechanical properties required from the final device, and its properties are adjusted to perform successfully during the early stages of its use, and systems having the mechanical properties required from the device during the early stages of its use, and its properties are adjusted to perform successfully during the final stage of its use.

According to some embodiments of the invention, the polymeric system comprises a thermoplastic polymer (e.g., a thermoplastic elastomer) which undergoes softening at a temperature above 37° C. The softening is optionally a decrease of at least 20%, optionally at least 30%, optionally at least 40%, optionally at least 50%, optionally at least 60%, optionally at least 70%, optionally at least 80%, optionally at least 90%, and optionally at least 95%, in the stiffness of the thermoplastic polymer at the temperature above 37° C., as compared to the stiffness of the polymer at 37° C. Other percentages between 20 and 100 are also contemplated.

The stiffness of the thermoplastic polymer before and after softening is as defined hereinabove and accordingly can be measured as described hereinabove.

According to some embodiments, the abovementioned decrease in stiffness occurs at a temperature in a range of from 40° C. to 60° C.

The thermoplastic polymer may represent, for example, at least 20% by weight of the polymeric system, optionally at least 40% by weight, optionally at least 50% by weight, at least 60% by weight, at least 80% by weight, at least 90% by weight, and optionally at least 99% by weight of the polymeric system.

In some embodiments, the polymeric system consists of a thermoplastic polymer as described herein.

In some embodiments, the polymeric system comprises or consists of two or more types of a thermoplastic polymer, which together exhibit the desired thermoplastic characteristics, as described hereinabove.

As used herein, the term "thermoplastic" refers to a polymer which is sufficiently soft above a certain temperature so as to readily allow plastic deformation of the polymer, and which is sufficiently stiff below a certain temperature so as to retain a desired shape. The softening of a thermoplastic polymer often occurs at temperatures near and/or above a transition temperature (e.g., a glass transition temperature, a melting point) of the polymer. Such a transition temperature may be determined, for example, by calorimetry.

It is to be noted that the softening of a polymer can occur also at temperatures lower (or higher) than a transition temperature as determined for a certain polymer.

The stiffness of a tubular structure made, at least in part, from a thermoplastic polymer as described herein can therefore be manipulated by increasing or decreasing the temperature of its environment, so as to effect a decrease or increase of its stiffness, respectively.

Thus, a polymeric system comprising a thermoplastic polymer according to embodiments of the present invention may optionally be softened by exposing the polymeric system to a sufficiently high temperature, shaped as desired (e.g., expanding a tubular structure comprising the polymeric system), and cooled to a temperature at which the polymeric system is sufficiently stiff so as to retain its shape (e.g., such that a tubular structure comprising the polymeric system retains an expanded state).

Optionally, the temperature at which the thermoplastic polymer is softened as described above (e.g., a temperature which facilitates expanding the tubular structure) is a temperature which does not cause excessive damage to tissue, for example 60° C. or less, optionally 55° C. or less, and optionally 50° C. or less.

In some embodiments, the thermoplastic polymer is selected such that the tubular structure is capable of retaining an expanded state at a physiological temperature of 37° C., or between 37° C. and 40° C. or even 42° C. or 45° C., such that an expanded state is retained also in fevered subjects.

In such embodiments, the stimulation upon which the tubular structure becomes stiffer optionally comprises cooling of the tubular structure from a temperature above body temperature, at which the thermoplastic polymer is sufficiently soft so as to render the tubular structure expandable, to a body temperature (a physiological temperature). Optionally, the stimulation comprises a further type of stimulation in addition to the aforementioned cooling (e.g., any other type of stimulation described herein).

It is to be appreciated that the stimulation by cooling may optionally comprise passive cooling, for example, by merely having the tubular structure in the body, without external heating, for sufficient time to allow cooling to body temperature. Alternatively or additionally, the stimulation may comprise active cooling, for example, causing a fluid having a temperature below body temperature pass through the tubular structure (e.g., by means of passing such a fluid through an inflating balloon).

In some embodiments, the thermoplastic polymer is characterized by a transition temperature (e.g., a glass transition temperature, a melting point) in a range of from about 45° C. to about 60° C.

A thermoplastic polymer as described herein encompasses a polymer, a co-polymer and/or a mixture of one or more polymers and/or copolymers.

Examples of thermoplastic polymers according to some embodiments of the invention include, for example, a polyester, a polycarbonate, a polyurethane, a polyether urethane, a polyether carbonate, a polyester carbonate, a polyester urethane, a polyanhydride, a polyamide, a polyolefin, a polyacrylate, a polymethacrylate, a halogenated polymer and a silicone polymer, and combinations and copolymers thereof, all being characterized as thermoplastic as defined herein.

In some embodiments, the thermoplastic polymer is a polycaprolactone (as an exemplary polyester), or a copolymer thereof, such as a polyester carbonate, a polyester urethane, a polycaprolactone-polyether copolymer (e.g., polycaprolactone-polyethylene glycol, polycaprolactone-polypropylene glycol, polycaprolactone-polytetramethylene glycol), and/or a copolymer of polycaprolactone and another polyester (e.g., polycaprolactone-polylactic acid).

Further examples of suitable polyesters include polybutylene succinate, polyethylene adipate and polyethylene sebacate.

Examples of suitable polyamides include polybutylene sebacamide and polyhexamethylene sebacamide.

According to optional embodiments, thermoplastic polymers suitable for use in the context of these embodiments of the present invention are represented by the following general formula:

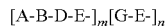

wherein:

A is $[-O-X_1-C(=O)-]_o$;
B is $-O-[X_2-O-]_p$;
D is $[-C(=O)-X_3-O-]_q$;
E is $-C(=O)-NH-X_4-NH-C(=O)-$;
G is $[-O-X_5]_r-O-$;
o, p, q and r are each independently integers from 1 to 1,000;

m and n are each independently 0 or an integer from 1 to 1000, wherein at least one of m and n is an integer from 1 to 1000; and $X_1$-$X_5$ are each independently an alkylene (e.g., an alkylene of 2 to 10 carbon atoms).

The above general formula encompasses copolymers (e.g., block polymers, random polymers) obtainable by reaction of an alkylene diisocyanate (e.g., hexamethylene diisocyanate) with a diol to form urethane bonds. The moiety E in the above formula represents a diurethane residue obtained by reaction of the diisocyanate.

The diol is selected from the group consisting of an alkylene glycol (e.g., ethylene glycol, tetramethylene glycol) or oligomer or polymer thereof, as represented by the moiety G, and a hydroxyl-terminated polyester having a structure represented by the moieties A-B-D, wherein A and D are each derived from a hydroxycarboxylic acid (e.g., caprolactone, lactic acid) and B is an alkylene glycol (e.g., ethylene glycol, tetramethylene glycol) or oligomer or polymer thereof which links to the carboxylic acid ends of A and D via an ester bond. Some such hydroxyl-terminated polyesters are commercially available, for example, polycaprolactones comprising a diethylene glycol linking the carboxylic acid ends.

The polymer of the above formula may be terminated, without limitation, by a hydroxyl group (—OH), by an alkoxy group (e.g., methoxy, ethoxy, propoxy), and/or by an amine group (e.g., resulting from decomposition of a terminal —NH—C(=O)—OH group to —NH$_2$+CO$_2$), as defined herein.

Exemplary polymers according to the above formula, and methods for their preparation, are presented in the Examples section that follows.

Syntheses of exemplary thermoplastic polymers are described in Example 1 and depicted in FIGS. 10 and 11.

As exemplified in Example 2 in the Examples section that follows, polymers described herein may be used to prepare a tubular structure, for example, by dip coating, by electrospinning and/or by an air-spray technique. Additional techniques for working polymers are known by those skilled in the art, and may optionally be used to prepare a device as described herein.

As exemplified in Example 3 in the Examples section that follows, and shown in FIG. 16, tubular structures prepared from thermoplastic polymers according to some embodiments of the invention may be conveniently expanded (e.g., increasing a diameter by at least approximately 200%) by heating the tubular structure to a temperature of approximately 50° C. As further exemplified therein, the heating may be applied by inserting a balloon filled with a warm liquid (e.g., water, saline) into the tubular device. The balloon used to heat the thermoplastic polymer may optionally be used to expand the tubular structure, as further detailed hereinbelow.

The deployment of devices comprising a thermoplastic polymer (including expansion of the tubular structures in situ) is exemplified in in vitro and in vivo models (see, for example, Examples 6-9 in the Examples section that follows).

As exemplified in FIG. 6, the thermoplasticity of a polymer enables, in some embodiments of the invention, welding of structures comprising the thermoplastic polymer.

Thus, in some embodiments, the softening of a thermoplastic polymer at an elevated temperature described herein makes a tubular structure comprising the thermoplastic polymer weldable. Optionally, the welding comprises applying pressure in addition to applying a temperature which softens the polymer.

The thermoplastic polymers described herein can be also categorized as biodegradable or non-biodegradable thermoplastic polymers.

In some embodiments, the thermoplastic polymer is biodegradable.

As used herein and well known in the art, the term "biodegradable" with respect to a polymer describes a describes a material which can decompose under physiological conditions into breakdown products. Such physiological conditions include, for example, hydrolysis (decomposition via hydrolytic cleavage), enzymatic catalysis (enzymatic degradation), and mechanical interactions. This term typically refers to substances that decompose under these conditions such that 50 weight percents of the substance decompose within a time period shorter than one year.

The term "biodegradable" as used in the context of the present invention, also encompasses the term "bioresorbable", which describes a substance that decomposes under physiological conditions to break down to products that undergo bioresorption into the host-organism, namely, become metabolites of the biochemical systems of the host-organism.

Examples of biodegradable polymers include polyesters (e.g., aliphatic polyesters) such as are described herein (e.g., polycaprolactone and copolymers thereof). Additional examples include, but are not limited to, aliphatic polyesters made of glycolide (glycolic acid), lactide (lactic acid), p-dioxanone, trimethylene carbonate, hydroxybutyrate, hydroxyvalerate, and also biodegradable co-polyamides, polydihydropyrans, polyphosphazenes, poly(ortho-esters), polycarbonates, poly(cyano acrylates), polyanhydrides and any combination thereof.

In some embodiments, the thermoplastic polymer is a non-biodegradable polymer.

The term "non-biodegradable" with respect to a polymer describes a substance which does not undergo degradation under physiological conditions. This term typically refers to substances which decompose under these conditions such that more than 50 percents do not decompose within at least 1 year, preferably within 2 years, 3 years, 4 years, and up to 10 years and even 20 or 50 years.

Exemplary non-biodegradable thermoplastic polymers as described herein include, but are not limited to, silicone polymers, such as poly(di-p-tolylsiloxane (Tg=50° C.), poly (phenyl-p-tolyl siloxane) (Tg=40° C.), poly(di-phenylsiloxane) (Tg=40° C.); ethylene based polymers, such as different ethylene-octene co-polymers (also referred to as Exact; e.g., Exact9061 (m.p.=41° C.), Exact9071 (m.p.=50° C.), Exact9361 (m.p.=41° C.), and Exact9371 (m.p.=55° C.)); ethylene vinyl acetate copolymers; and polyesters such as, for example, polybutylene terthphtalate, polyhexamethylene terthphtalate, polyoctamethylene terthphtalate, polyethylene adipate, polybutylene adipate, polyethylene pimelate, polybutylene pimelate, polypropylene adipate, polybutylene azealate, polyproylene azealate, and polyproylene sebacate; and polymethacrylates such as polypropyl methacrylate, and combinations and copolymers thereof, all being characterized as thermoplastic as defined herein.

As described herein, thermoplastic polymers such as described herein are particularly useful for constructing a device, such as a device comprising a tubular structure, which can be expanded in a body vessel in situ, and retain an expanded state. Such a feature facilitates the deployment of a device in a vessel for lining the vessel (e.g., by expanding the tubular structure in a vessel until the walls of the tubular vessel are in full contact with the walls of the vessel). As further described herein, the abovementioned feature is useful for treating an aneurysm.

Hence, according to another aspect of embodiments of the present invention, there is provided a use of a thermoplastic polymer in the manufacture of a medical device for lining a body vessel and/or for treating an aneurysm in a blood vessel. The thermoplastic polymer (e.g., a thermoplastic polymer as described herein) is characterized in that it undergoes a decrease of its stiffness of at least 20% at a temperature ranging from 40° C. to 60° C., as detailed hereinabove.

According to another aspect of embodiments of the invention, there is provided a thermoplastic polymer (e.g., a thermoplastic polymer described herein) which undergoes a decrease of its stiffness of at least 20% at a temperature ranging from 40° C. to 60° C., which is identified for use in a method of lining a body vessel and/or in a method of treating an aneurysm in a subject in need thereof.

According to another aspect of embodiments of the invention, there is provided method of lining a body vessel and/or of treating an aneurysm of a blood vessel in a subject in need thereof, effected by introducing into the vessel a thermoplastic polymer which undergoes a decrease of its stiffness of at least 20% at a temperature ranging from 40° C. to 60° C. (e.g., a thermoplastic polymer as described herein).

In some embodiments, utilizing a thermoplastic polymer as described herein for lining a body vessel and/or for treating an aneurysm of a blood vessel is effected by:

introducing into the vessel a tubular structure made, at least in part, from a thermoplastic polymer as described herein;

heating the thermoplastic polymer so as to decrease its stiffness by at least 20%, as described herein, to thereby obtain a soften thermoplastic polymer;

expanding the softened thermoplastic polymer; and generating conditions for the thermoplastic polymer to cool to a physiological temperature (e.g., 37° C.±5° C.), such that the tubular structure experiences stiffening, thereby lining the vessel and further thereby treating an aneurysm of a blood vessel.

A further discussion of the procedures involved in utilizing a thermoplastic polymer in the above methods is provided hereinunder.

Utilizing a thermoplastic polymer as described herein in the device described herein is associated with a thermal stimulation.

Thus, in some embodiments, a device comprising a tubular structure made of a thermoplastic polymer as described herein is such that upon a thermal stimulation that comprises heating a polymeric system that comprises a thermoplastic polymer, the polymer softens, facilitating its expansion, and upon a thermal stimulation that involves generating conditions for the thermoplastic polymer to cool to a physiological temperature (e.g., 37° C.±5° C.), the polymer stiffens and retains its expanded state.

The thermal stimulation used for softening the polymer can be effected by heating the polymer, for example, by means of placing a structure made from the polymer in a balloon filled with heated solution, as described herein. The heating can be applied prior to introducing the device into the vessel or in situ, upon deployment of the structure. As noted hereinabove, the second thermal stimulation can comprise passively exposing the thermoplastic polymer to a physiological temperature (e.g., by arresting the heating) or by actively cooling the device containing the polymer in situ.

It is to be noted that a polymeric system used for forming a tubular structure as described herein, can comprise, according to these embodiments of the invention, in addition to a thermoplastic polymer, additional components, such that the stimulation(s) applied to such systems are manipulated accordingly.

Further, a polymeric system utilized in any of the devices and methods described herein, can be configured so as to include one, two or even more components, such that the system is capable of changing its stiffness and of generating upon stimulation a polymeric material that has a stiffness higher than that of the system used for forming the tubular structure under physiological conditions.

Accordingly, according to further optional embodiments of the medical device described hereinabove, the polymeric system is configured to produce a polymeric material upon a stimulation (e.g., a stimulation as described herein) under physiological conditions, such that a stiffness of the polymeric material is higher than a stiffness of the polymeric system. Optionally, the increase of stiffness is an increase by at least 20%, optionally at least 30%, optionally at least 40%, optionally at least 50%, optionally at least 60%, optionally at least 80%, optionally at least 100%, optionally at least 200%, optionally at least 300%, optionally at least 500%, and optionally even by at least 900%. Other percentage values are also contemplated As used herein, the term "polymeric material" refers to a material composed primarily of a polymer and/or a related compound (e.g., a cross-linked polymer, a derivative of a polymer, a co-polymer) or a mixture thereof.

A polymeric material differs from a polymeric system in that the polymeric material in the final end product from which the tubular structure is made, whereby the polymeric system comprises a substance or a mixture of substances that are subjected to a stimulation so as to form the final polymeric material.

The present inventors have devised various systems that are suitable for use in the context of embodiments of the present invention. The following list exemplary systems, which are also referred to herein as "smart" systems, which include a "smart" component. The "smart" component is referred to herein as a substance that is responsive to the stimulation, such that its response results in a change of the stiffness of the final polymeric material. Other systems are also contemplated.

In some embodiments, the polymeric system comprises a polymer and at least one compound (e.g., a monomer or oligomer) which undergoes polymerization and/or cross-linking upon a stimulation as described herein.

Stimulation of such a compound may optionally result in polymerization and/or cross-linking of the compound. For example, optical stimulation and/or chemical stimulation may be suitable for inducing free radical polymerization and/or cross-linking of the monomer or oligomer to thereby obtain another polymer (non cross-linked or cross-linked). The resulting polymeric mixture represents a polymeric material as described herein, and is configured to be characterized by a stiffness higher than that of the polymeric system, by selecting the appropriate polymer and monomer or oligomer composing the polymeric system.

Examples of monomers suitable for use in the context of these embodiments of the invention include, but are not limited to, vinylic monomers such as an acrylate, a methacrylate, a diacrylate and a dimethacrylate.

Examples of oligomers suitable for use in the context of these embodiments of the invention include, but are not limited to, PEG 600diacrylate, PPG500diacrylate, PEG 600dimethacrylate, PPG500dimethacrylate, double bond end capped PEG/PPG diblocks and triblocks, low molecular weight polyamides, polyurethanes and polyesters.

In an exemplary embodiment, a polymeric system comprises polymethyl methacrylate, poly(styrene-co-methyl methacrylate) or polycaprolactone-polyurethane (e.g., CLUR2000) as a polymer and 2-hydroxyethyl methacrylate (HEMA) as a monomer (see, Example 10 in the Examples section that follows). In a further exemplary embodiment, a polymeric system comprises polycaprolactone (e.g., PCL80K) as a polymer and ethylene glycol dimethacrylate (EGDMA) as a monomer (see, Example 10).

In some embodiments, the polymeric system comprises a polymer and a hydrophilic (e.g., water-soluble) compound which plasticizes the polymer. Optionally, the hydrophilic compound is a polyalkylene glycol (e.g., polyethylene glycol). The hydrophilic compound optionally has a low molecular weight, e.g., optionally less than 2000 Da, optionally less than 1000 Da, and optionally less than 500 Da. As used herein, the term "plasticize" refers to the reduction of a stiffness of a polymer by another molecule.

Optionally, stimulation causes the hydrophilic plasticizer to escape from the polymeric system (e.g., by diffusion), thereby increasing the stiffness of the polymer which remains. The stimulation may comprise, for example, exposure to an aqueous environment (e.g., blood flow) for a sufficient time period (e.g., at least 5 minutes, optionally at least 10 minutes, optionally at least 20 minutes, optionally at least 1 hour, optionally at least 3 hours, optionally at least 12 hours, and optionally at least 24 hours). Optionally, a sufficient time period ranges from a few minutes to a few hours. Further optionally, it is no more than 24 hours.

Alternatively, stimulation can be a mechanical stimulation, for example, expanding a tubular structure that comprises such a system, which leads to release of the plasticizer from the system, and results in a polymer material with higher stiffness than that of the system. Further alternatively, such a system may react upon exposure to an aqueous environment (e.g., blood flow) as a first stimulation by swelling, which is effected by the hydrophilic substance, whereby the swelled system is then subjected to another stimulation (e.g., mechanical, thermal, chemical, or other), which leads to release of the plasticizer from the system, and results in a polymer material with higher stiffness than that of the system.

In some embodiments, stimulation by exposure to an aqueous environment results in "Solvent Induced Crystallization (SINC)" where the solvent is water, such that the polymer, upon release of the plasticizer, re-organizes in the presence of a small amount of the solvent, into a crystalline form thereof. The latter is characterized by a higher stiffness as compared to non-crystalline or semi-crystalline form of the polymer.

In some embodiments, the polymeric system comprises a polymer having a first functional group and a polymer having a second functional group, wherein the first functional group and the second functional group are capable of reacting with one another upon stimulation under physiological conditions to form cross-links, such that the obtained polymeric material is a cross-linked polymer.

Thus, in these embodiments, cross-linking is effected so as to form a polymeric material with stiffness higher that the polymeric system. Stimulation for effecting such a cross-linking include, but is not limited to, chemical stimulation and/or thermal stimulation (e.g., subjecting the polymeric system to the presence of a suitable catalyst; subjecting a polymeric system that already comprises a suitable catalyst to physiological conditions (e.g., 37±5° C. and/or aqueous environment); subjecting the polymeric system to physiological conditions (e.g., 37±5° C. and/or aqueous environment); or irradiative stimulation, preferably light in the visible or UV spectral range The aforementioned polymeric system optionally comprises a polymer having both the first and second functional groups, such that the polymer is capable of cross-linking with itself. Such a system would be a mono-component system or a bi-component system, in case where a catalyst is required for promoting cross-linking. Alternatively or additionally, the system comprises a first functional group on one polymer and a second functional group on a different polymer, such that the system comprises a pair of polymers capable of cross-linking with one another. Such a system would be a bi-component system or a tri-component system, in cases where a catalyst is required for promoting cross-linking.

Examples of pairs of functional groups capable of reacting with one another include an azide and an alkyne, an unsaturated carbon-carbon bond (e.g., acrylate, methacrylate, maleimide) and a thiol, an unsaturated carbon-carbon bond and an amine, a carboxylic acid and an amine, a hydroxyl and an isocyanate, a carboxylic acid and an isocyanate, an amine and an isocyanate, a thiol and an isocyanate. Additional examples include an amine, a hydroxyl, a thiol or a carboxylic acid along with a nucleophilic leaving group (e.g., hydroxysuccinimide, a halogen).

It is to be appreciated that for each pair of functional groups described hereinabove, either functional group can correspond to the "first functional group" or to the "second functional group".

In exemplary embodiments, the first and second functional groups comprise (in no particular order) an azide and an alkyne. These two functional groups may combine to form a triazole ring, by a mechanism referred to as "click" chemistry. Formation of a triazole ring constitutes cross-linking (e.g., between two polymers and/or within a single polymer), which increases a stiffness of the polymeric system. Optionally, a stimulation which results in such cross-linking comprises exposure to a catalyst of a click reaction. Copper compounds (e.g., Cu(I) compounds) are exemplary catalysts of a click reaction.

In some embodiments, the first and/or the second functional groups can be latent groups, which are exposed upon said stimulation, such that cross-linking is effected once a latent group is exposed. Exemplary such groups include, but are not limited to, functional groups as described hereinabove, which are protected with a protecting group that is labile under the stimulation.

Examples of labile protecting groups and the forms of stimulation to which they are susceptible include, for example, carboxylate esters, which may hydrolyzed to form an alcohol and a carboxylic acid by exposure to an esterase and by exposure to acidic or basic conditions; silyl ethers such as trialkyl silyl ethers, which can be hydrolysed to an alcohol by acid or fluoride ion; p-methoxybenzyl ethers, which may be hydrolysed to an alcohol, for example, by oxidizing conditions or acidic conditions; t-butyloxycarbonyl and 9-fluorenylmethyloxycarbonyl, which may be hydrolysed to an amine by a exposure to basic conditions; sulfonamides, which may be hydrolysed to a sulfonate and amine by exposure to a suitable reagent such as samarium iodide or tributyltin hydride; acetals and ketals, which may be hydrolysed to form an aldehyde or ketone, respectively, along with an alcohol or diol, by exposure o acidic conditions; acylals (i.e., wherein a carbon atom is attached to two carboxylate groups), which may be hydrolysed to an aldehyde of ketone, for example, by exposure to a Lewis acid; orthoesters (i.e., wherein a carbon atom is attached to three alkoxy or aryloxy groups), which may be hydrolysed to a carboxylate ester (which may be further hydrolysed as described hereinabove) by exposure to mildly acidic conditions; 2-cyanoethyl phosphates, which may be converted to a phosphate by exposure to mildly basic conditions; methylphosphates, which may be hydrolysed to phosphates by exposure to strong nucleophiles; phosphates, which may be hydrolysed to alcohols, for example, by exposure to phosphatases; and aldehydes, which may be converted to carboxylic acids, for example, by exposure to an oxidizing agent.

In some embodiments, the polymeric system comprises a polymer and a compound which reacts with the polymer upon stimulation, so as to produce the polymeric material. The polymeric material can be, for example, a cross-linked form of the polymer, a derivative of the polymer (e.g., a chain extension derivative of the polymer) or a co-polymer (either non cross-linked or cross-linked).

Optionally, the compound is a monomer or oligomer which undergoes polymerization upon stimulation. The compound undergoing polymerization may react with a polymer originally present in the polymeric system, for example, by cross-linking with the polymer as a result of polymerization of the monomer or oligomer (e.g., wherein a functional group in the original polymer attaches to a monomer or oligomer during polymerization) and/or by forming a copolymer with the polymer originally present in the system (e.g., by chain extension of the original polymer).

Suitable stimulations for effecting the herein-described interactions between a polymer and the monomer or oligomer include, but are not limited to, thermal stimulation (e.g., exposing to a physiologic temperature); chemical stimulation (e.g., for exposing a latent functional group, as described herein); and/or optical stimulation (e.g., for exposing a latent functional group and/or for initiating polymerization).

Examples of monomers suitable for use in the context of there embodiments include, but are not limited to, acrylates, methacrylates, diacrylates and dimethacrylates, as well as other monomers that polymerize or cross-link at mild conditions such as physiological conditions or biocompatible conditions.

Optionally, the compound is a cross-linker capable of cross-linking the polymer upon stimulation. Suitable cross-linkers include compounds with two or more reactive functional groups (e.g., thiol, amine, unsaturated bond, azide, alkyne and optionally any functional group described herein with respect to the abovementioned first and second functional groups) capable of reacting with a functional group of a polymer, for example, a dithiol, a diamine, an aminothiol, an amino acid (e.g., lysine, cysteine), an oligopeptide, a bis(azide), a dialkyne, a diacrylate and a dimethacrylate, and combinations thereof. The functional groups of the cross-linker may be the same (e.g., as in a dithiol and a diamine) or different (e.g., as in an aminothiol). The cross-linker may be a small molecule (e.g., a monomer) or a large molecule (e.g., an oligomer or a polymer).

In some embodiments, the compound which reacts with the polymer and/or the polymer itself comprise functional groups which are latent groups, which are exposed upon the stimulation, such that cross-linking is effected once a latent group or groups are exposed. Exemplary latent groups and suitable types of stimulation for exposing the latent groups are described hereinabove which are protected with a protecting group that is labile under the stimulation.

In an exemplary embodiment, the cross-linker is a bis(azide), such as an azide-terminated polymer, and the polymer being cross-linked comprises alkyne groups. Cross-linking may result from a click reaction, as described herein.

The present inventors have also contemplated "smart" systems as described herein, which are based on manipulating a crystalline form of a polymer present in the polymeric system. In general, embodiments relating to such a manipulation involve stimulation that effects transformation from an amorphous form to a semi-crystalline form or crystalline form, or from a semi-crystalline form to a crystalline form. Polymeric systems useful in these embodiments are therefore selected so as to undergo crystallization of a polymer upon stimulation.

As used herein, a substance (e.g., a polymer) in an amorphous form comprises at least 60% by weight thereof as amorphous, optionally, at least 70% by weight, at least 80% by weight, at least 90% by weight, and also 100%.

As used herein, a substance (e.g., a polymer) in a crystalline form comprises at least 50% by weight thereof as crystalline, optionally, at least 60% by weight, at least 70% by weight, at least 80% by weight, at least 90% by weight, and also 100%.

Crystallinity of a substance can be determined by methods well known in the art (e.g., by measuring X-Ray diffraction).

In some embodiments, the polymeric system comprises a substance (e.g., a substance comprising a polymer) in an amorphous form. Upon stimulation, at least a portion of the amorphous form undergoes crystallization to form a crystalline or semi-crystalline form of the substance.

In such an embodiment, the crystalline or semi-crystalline form of the substance provides the polymeric system with more stiffness than does the amorphous form of the substance. Optionally, a polymer undergoes crystallization, such that the polymeric material is a crystalline or semi-crystalline polymer which is stiffer than the amorphous form of the polymer.

Optionally, the substance in an amorphous form comprises a compound (e.g., a polymer) characterized by a crystallization temperature at or slightly below 37° C. (e.g., in a range of 30-37° C.), such that exposure to physiological temperature provides stimulation for crystallization. Exemplary polymers exhibiting a suitable crystallization temperature include, but are not limited to, polycaprolactone-polyurethanes (e.g., CLUR polymers) having a molecular weight in a range of 4500-11200. An amorphous state of such polymers may be obtained, for example, by melting the polymer and then rapidly quenching the polymer.

Additionally or alternatively, crystallization of a substance in amorphous form is enhanced by absorption of water into the substance, such that exposure to an aqueous environment in a body provides a stimulation for crystallization. Without being bound by any particular theory, it is believed that absorbed water can induce crystallization of a polymer by increasing a mobility of the polymer chains (e.g., by acting as a plasticizer) so as to allow reordering of molecules to take place, thereby inducing crystallization, as described herein as SINC). Optionally, the substance comprises a cross-linked polymer in a non-crystalline (e.g., amorphous or semi-crystalline) form, the polymer comprising degradable cross-links which interfere with crystallization of the polymer. Stimulation comprises degrading (e.g., hydrolysis) of the cross-links, and at least a portion of the polymer undergoes crystallization following (partial or total) degradation of the cross-links.

Optionally, the cross-links are unstable in an aqueous environment at physiological temperature and/or pH, such that exposure to the aqueous environment in a body provides a stimulation.

Alternatively or additionally, the cross-links are susceptible to enzymatic degradation (e.g., by esterases), such that exposure to enzymes in a body provides the stimulation.

Oligoester and polyester (e.g., aliphatic oligoester and polyester) cross-links are examples of a degradable (e.g., hydrolysable) cross-link.

Similarly, in some embodiments, the polymeric system comprises a substance (e.g., a substance comprising a polymer) in a semi-crystalline form. Upon stimulation, at least a portion of the semi-crystalline form undergoes crystallization to form a crystalline form of the substance, which is characterized by higher stiffness.

In some embodiments, the polymeric system comprises a substance is a non-crystalline form (e.g., an amorphous form or a semi-crystalline form) and an additional hydrophilic substance. Such a system, when exposed to an aqueous environment (e.g., a blood vessel) as a stimulation, can undergo swelling due to the non-crystalline nature of the polymer and/or the hydrophilic nature of the additional substance. As noted hereinabove, such a swelling results in decreased stiffness. Upon expansion, and possibly another stimulation, as described hereinabove, the additional substance is released from the system, the latter "loses" its hydrophilic nature such that swelling is reduced, and is subjected to "Solvent Induced Crystallization" as described hereinabove.

Optionally, the substance in an amorphous form comprises a compound having the general formula:

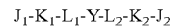

wherein:

$J_1$ and $J_2$ are each a polyalkylene glycol (e.g., a polyethylene glycol);

$K_1$ and $K_2$ are each a hydrophobic (e.g., water-insoluble) segment;

$L_1$ and $L_2$ are each independently a bifunctional linking moiety or absent; and Y is selected from the group consisting of a polyester (e.g., a polycaprolactone), a polyurethane, a polyamide, a silicone polymer, a polyacrylate, a polymethacrylate, and a polyolefin, of suitable molecular weight.

The polyalkylene glycol is optionally capped by an alkyl (e.g., methyl, ethyl, propyl).

Optionally, each of $J_1$ and $J_2$ has an average molecular weight in a range of from 250 to 5000 Da, and optionally in a range of from 300 to 2000 Da (e.g., about 350 Da).

Compounds having the above formula are degradable under physiological conditions such that exposure to physiological conditions provides a stimulation which initiates crystallization.

A substance in a non-crystalline form, as described herein, is optionally prepared by blending a polymer with a compound which inhibits crystallization of the polymer. Optionally the compound is covalently bound to the polymer via a non-biodegradable or a biodegradable connector. For example, a water-soluble material such as polyethylene glycol may be covalently bound to a more hydrophobic polymer (e.g., a CLUR polymer). The water-soluble material may inhibit crystallization of the polymeric substance, for example, by absorbing water into the substance.

The compound optionally solidifies at a higher temperature than does the polymer (e.g., a CLUR polymer). When the polymeric substance is melted and then cooled, the compound will solidify first, thereby preventing or at least reducing the crystallization of the polymer, even at a lower temperature. Optionally, the compound is a polymer having a glass transition of approximately 80-120° C. (e.g., polyacrylic acid), which is significantly higher than the crystallization temperature of many polymers (e.g., CLUR polymers).

In any of the embodiments relating to the "smart" systems as described herein, suitable polymers include biodegradable polymers such as described hereinabove for thermoplastic polymers and non-biodegradable polymers such as, but not limited to, polyamides such as polyhexamethylene adipamide, polyoctamethylene adipamide, polynonamethylene adipamide, polyhexamethylene sebacamide, polyoctamethylene sebacamide, polyhexamethylene azelamide, and polyhexamethylene dodecanediamine; polyolefins such as Low Density Polyethylene and ethylene-octene co-polymers Exact8201 and Exact8230; polyesters such as polydecamethylene terephthalate; Silicone polymers, such as poly(di-p-tolylsiloxane; Biomer, Pellethane, Cardiothane, Biospan, Estane, Tecoflex, as well as polystyrene, polymethyl methacrylate, polyethyl methacrylate, polyvinyl chloride and polypropyl methacrylate.

In any of the embodiments relating to the "smart" systems as described herein, suitable "smart" components, if present in a polymeric system in addition to the above-described polymers include, but are not limited to, hydroxy ethylmethacrylate, ethylene glycol dimethacrylate, diethylene glycol dimethacrylate, triethylene glycol dimethacrylate, tetraethylene glycol dimethacrylate, propylene glycol dimethacrylate, dipropylene glycol dimethacrylate, tripropylene glycol dimethacrylate, tetrapropylene glycol dimethacrylate, trimethylene dimethacrylate, propyl dimethacrylate, ethoxylated methacrylates, with the pendant PEG chain having different molecular weights, t-butyl methacrylate, PEG diacrylates of various molecular weights, PEG dimethacrylates of various molecular weights, PEG dithiols of various molecular weights, PEG di-hydroxy succinimide of various molecular weights, PEG maleimide of various molecular weights, PPG diacrylates of various molecular weights, PPG dimethacrylates of various molecular weights, PPG dithiols of various molecular weights, PPG di-hydroxy succinimide of various molecular weights, PPG maleimide of various molecular weights, diisocyanates of various types and molecular weights, such as hexamethylene diisocyanate (HDI), PEG-diHDI of various molecular weights, PPGdiHDI of various molecular weights, and compounds that can participate in click reaction (e.g., azide-containing compounds or alkyne-containing compounds).

Any combination of the polymers and the "smart" components described herein is contemplated, as long as it results in a polymeric material with the required stiffness upon stimulation, as described herein.

Polymeric systems exhibiting the properties described hereinabove can be useful as a component of a medical device.

Hence, according to another aspect of embodiments of the present invention, there is provided a use of a polymeric system having a stiffness which increases upon stimulation under physiological conditions (e.g., a stimulation described herein), in the manufacture of a medical device, for example, a medical device for lining a body vessel and/or for treating an aneurysm.

According to some embodiments, there is provided a use of a polymeric system described herein in the manufacture of a medical device.

Polymeric systems exhibiting the properties described hereinabove can also be useful per se for a wide variety of applications.

Hence, according to another aspect of embodiments of the present invention, there is provided a polymeric system configured to produce a polymeric material upon a stimulation under physiological conditions, such that a stiffness of the polymeric material is higher than a stiffness of the polymeric system, as such polymeric systems are described herein.

According to optional embodiments of the present invention, the medical device described herein is identified for use in a method suitable for lining a vessel. Optionally, the lining is for treating, e.g., isolating an aneurysm of the respective vessel.

According to another aspect of some embodiments of the invention, there is provided a method suitable for lining a body vessel, the method comprising introducing the medical device described herein, e.g., tubular structure 12, into the vessel. Optionally, the vessel is a blood vessel. The device can be introduced via a minimally invasive procedure, preferably using a catheter or another delivery apparatus, as further detailed hereinabove.

The method optionally further comprises expanding the device (e.g., a tubular structure of the device) in situ to an expanded state thereof. The diameter of the tubular structure in its expanded state is preferably the same or slightly larger than the diameter of the body vessel.

Optionally, the method further comprises decreasing the stiffness of the polymeric system of the device prior to the expansion of device, for example, by applying a suitable stimulation to the polymeric system.

According to some embodiments, the method further comprises subjecting the device to a stimulation which increases the stiffness of the polymeric system, subsequent to the expansion of the device, so as to fixate the expanded state of the device.

According to some exemplary embodiments, the tubular structure is expanded using an inflatable balloon. Preferably, the tubular structure can be mounted on the balloon prior to the delivery into the blood vessel. However, embodiments in which the balloon is delivered in its deflated state into the volume defined by the tubular structure after the tubular structure is in introduced into the body are not excluded from the scope of the present invention. The method optionally comprises inflating the balloon so as to expand the tubular structure.

The balloon may optionally be a balloon designed and/or marketed for being inflated in a vessel of a living body. Such balloons will be familiar to a skilled practitioner (e.g., a surgeon). Representative examples include, without limitation, balloons employed in stent deployment procedures and the like.

In some embodiments of the present invention the tubular structure comprises at least one branch member having a wall which is folded upon itself, and the method comprises unfolding the fold in situ as further detailed hereinabove.

In some embodiments of the present invention the tubular structure comprises one or more weldable branch members, and the method comprises delivering the branch members separately into the site of deployment (sequentially using the same delivering device, or using different delivering devices which may optionally introduced into the site of deployment via different routes). Once the branch members are at the site of deployment the method preferably expands and weld them in situ to each other as further detailed hereinabove. Optionally and preferably, the method comprises establishing fluid intercommunication between the lumens of the various members by forming in situ an opening at the point of joining between the members as further detailed hereinabove.

In some embodiments of the present invention one or more of the tubular members forming the medical device is provided as two or more separate layer members, each constituted to form a layer of the respective member. In these embodiments, the method comprises sequentially deploying the layer members at the site of deployment, preferably, but not necessarily, using the same delivering device, to form, in situ, a multilayer structure. Optionally, the method comprises welding the layers to each other as further detailed hereinabove.

The method may further comprise imaging at least the respective portion of the vessel in order to facilitate proper placement and expansion of the medical device. Examples of imaging techniques include, without limitation, visible light imaging, infrared imaging, magnetic resonance imaging, X-ray imaging, ultrasound imaging, and gamma ray and positron emission techniques. Imaging may be performed using a miniaturized imaging system mounted on a suitable catheter and introduced into body vessel. In some embodiments of the present invention the miniaturized imaging system is mounted on the same catheter that is used for delivering the device to the site of deployment. Alternatively or additionally, external imaging may be employed. Imaging may be performed with the aid of diagnostic agents. The most beneficial use of imaging in the context of the present invention is expected to be addition to the blood vessel of the patient of a diagnostic agent such as a contrast agent, in order to present an image of the blood vessel while introducing the medical device into the blood vessel.

The term "lining", as used herein, describes the process of covering a section of the inside wall of a vessel with at least one layer of material, without significantly impeding flow of a fluid (e.g., blood flow).

Lining a blood vessel may be intended, without limitation, for treating a hole in the vessel wall (e.g., a hemorrhage, a wound, a ruptured aneurysm) by covering the hole, optionally releasing beneficial drugs (e.g., drugs incorporated in the medical device and/or the polymeric system), inhibiting or reducing turbulent blood flow, treating atheromatous plaques and/or blood clots (e.g., by isolating the plaque debris and/or blood clots and/or trapping them so as to prevent or reduce the release of these plaque debris and/or blood clots into the bloodstream).

In some exemplary embodiments, lining a blood vessel is for treating an aneurysm in the blood vessel in a subject in need thereof. For example, the device may isolate the aneurysmal sac from the blood flow, thereby improving blood flow, reducing the likelihood of aneurysm rupture, and/or minimizing the lethality of aneurysm rupture.

Optionally, the aneurysm is an aortic aneurysm (e.g., an abdominal aortic aneurysm, a thoracic aortic aneurysm).

The methodologies disclosed herein are effective at lining a vessel and treating an aneurysm in a controllable and predictable manner. Unlike the traditional EVAR methodologies, the methodologies disclosed herein in accordance with some embodiments of the invention are of a relatively simple construction, are not very costly, and are preferably devoid of fabric features, metallic meshes and numerous interfaces between different components, which increase the risk of leaks. It is therefore believed that the polymer-based methodologies in accordance with some embodiments of the present invention represent an improvement over current EVAR technology.

As used herein throughout, the term "alkyl" refers to a saturated or unsaturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. In some embodiments, the alkyl is unsubstituted. When substituted, the substituent group can be, for example, cycloalkyl, aryl, heteroaryl, heteroalicyclic, halo, oxo, hydroxy, alkoxy, aryloxy, thiohydroxy, thioalkoxy, thioaryloxy, disulfide, sulfinyl, sulfonyl, sulfonate, sulfonate, sulfate, cyano, nitro, azide, phosphonyl, phosphinyl, carbonyl, thiocarbonyl, urea, thiourea, carbamyl, thiocarbamyl, amido, carboxylate, sulfonamido and amine, as these terms are defined herein.

As used herein throughout, the term "alkylene" refers to a divalent radical of alkyl, as defined hereinabove.

As herein, the term "alkene" refers to an unsaturated aliphatic hydrocarbon, as described hereinabove, comprising at least one pair of carbon atoms attached via a double bond.

As herein, the term "alkyne" refers to an unsaturated aliphatic hydrocarbon, as described hereinabove, comprising at least one pair of carbon atoms attached via a triple bond.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, cycloalkyl, aryl, heteroaryl, heteroalicyclic, halo, oxo, hydroxy, alkoxy, aryloxy, thiohydroxy, thioalkoxy, thioaryloxy, disulfide, sulfinyl, sulfonyl, sulfonate, sulfonate, sulfate, cyano, nitro, azide, phosphonyl, phosphinyl, carbonyl, thiocarbonyl, urea, thiourea, carbamyl, thiocarbamyl, amido, carboxylate, sulfonamido and amine, as these terms are defined herein.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, cycloalkyl, aryl, heteroaryl, heteroalicyclic, halo, hydroxy, alkoxy, aryloxy, thiohydroxy, thioalkoxy, thioaryloxy, disulfide, sulfinyl, sulfonyl, sulfonate, sulfonate, sulfate, cyano, nitro, azide, phosphonyl, phosphinyl, carbonyl, thiocarbonyl, urea, thiourea, carbamyl, thiocarbamyl, amido, carboxylate, sulfonamido and amine, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, cycloalkyl, aryl, heteroaryl, heteroalicyclic, halo, hydroxy, alkoxy, aryloxy, thiohydroxy, thioalkoxy, thioaryloxy, disulfide, sulfinyl, sulfonyl, sulfonate, sulfonate, sulfate, cyano, nitro, azide, phosphonyl, phosphinyl, carbonyl, thiocarbonyl, urea, thiourea, carbamyl, thiocarbamyl, amido, carboxylate, sulfonamido and amine, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, cycloalkyl, aryl, heteroaryl, heteroalicyclic, halo, oxo, hydroxy, alkoxy, aryloxy, thiohydroxy, thioalkoxy, thioaryloxy, disulfide, sulfinyl, sulfonyl, sulfonate, sulfonate, sulfate, cyano, nitro, azide, phosphonyl, phosphinyl, carbonyl, thiocarbonyl, urea, thiourea, carbamyl, thiocarbamyl, amido, carboxylate, sulfonamido and amine, as these terms are defined herein. Representative examples are 4,5-dihydroimidazole, piperidine, piperazine, tetrahydrofuran, tetrahydropyran, morpholine and the like.

As used herein, the terms "amine" and "amino" refer to a —NR'R" group, wherein R' and R" are selected from the group consisting of hydrogen, alkyl, cycloalkyl, heteroalicyclic (bonded through a ring carbon), aryl, and heteroaryl (bonded through a ring carbon). Optionally, R' and R" are non-substituted. Optionally, R' and R" are selected from the group consisting of hydrogen and alkyl comprising 1 to 4 carbon atoms.

A "hydroxy" or "hydroxyl" group refers to an —OH group.

An "azide" group refers to a —N=N$^+$=N$^-$ group.

An "alkoxy" group refers to both an —O-alkyl group and an —O-cycloalkyl group.

An "aryloxy" group refers to both an —O-aryl group and an —O-heteroaryl group.

A "thiohydroxy" or "thiol" group refers to a —SH group.

A "thioalkoxy" group refers to both an —S-alkyl group, and an —S-cycloalkyl group.

A "thioaryloxy" group refers to both an —S-aryl and an —S-heteroaryl group.

A "disulfide" group refers to both a —S-thioalkoxy and a —S-thioaryloxy group.

A "carbonyl" group refers to a —C(=O)—R' group, where R' is defined as hereinabove.

A "thiocarbonyl" group refers to a —C(=S)—R' group, where R' is as defined herein.

An "oxo" group refers to a =O group.

A "carboxylate" encompasses both —C(=O)—O—R' and R'C(=O)—O— groups, wherein R' is as defined herein.

A "carbosylic acid" refers to a —C(=O)OH group.

A "thiocarboxy" or "thiocarboxylate" group refers to both —C(=S)—O—R' and —O—C(=S)R' groups, wherein R' is as defined herein.

A "halo" group or "halogen" refers to fluorine, chlorine, bromine or iodine.

A "sulfinyl" group refers to an —S(=O)—R' group, where R' is as defined herein.

A "sulfonyl" group refers to an —S(=O)$_2$—R' group, where R' is as defined herein.

A "sulfonate" group refers to an —S(=O)$_2$—O—R' group, where R' is as defined herein.

A "sulfate" group refers to an —O—S(=O)$_2$—O—R' group, where R' is as defined as herein.

A "sulfonamide" or "sulfonamido" group encompasses both —S(=O)$_2$—NR'R" and R'S(=O)$_2$—N(R")— groups, where R' and R" are as defined herein.

A "carbamyl" or "carbamate" group encompasses —OC(=O)—NR'R" and R'OC(=O)—NR"— groups, wherein R' and R" are as defined herein.

A "thiocarbamyl" or "thiocarbamate" group encompasses —OC(=S)—NR'R" and R'OC(=S)—NR"— groups, wherein R' and R" are as defined herein.

An "amide" or "amido" group encompasses —C(=O)—NR'R" and R'C(=O)—NR"— groups, wherein R' and R" are as defined herein.

A "nitro" group refers to an —NO$_2$ group.

An "isocyanate" refers to a —N=C=O group.

A "cyano" group refers to a —C≡N group.

The term "phosphonyl" or "phosphonate" describes a —P(=O)(OR')(OR") group, with R' and R" as defined hereinabove.

The term "phosphate" describes an —O—P(=O)(OR')(OR") group, with each of R' and R" as defined hereinabove.

The term "phosphinyl" describes a —PR'R" group, with each of R' and R" as defined hereinabove.

A "urea" group refers to an —N(R')—C(=O)—NR"R'" group, where each of R', R" and R'" is as defined herein.

The term "thiourea" describes a —N(R')—C(=S)—NR"R'" group, with each of R', R" and R'" as defined hereinabove.

The term "acrylate" encompasses acrylic acid and derivatives thereof, including esters of acrylic acid, acrylamide and other amide derivatives of acrylic acid. Optionally, "acrylate" is an ester of acrylic acid.

The term "methacrylate" encompasses methacrylic acid and derivatives thereof, including esters of methacrylic acid, methacrylamide and other amide derivatives of methacrylic acid. Optionally, "methacrylate" is an ester of methacrylic acid.

A "diacrylate" refers to a compound comprising two acrylate moieties as denied herein (e.g., acrylate ester moieties).

A "dimethacrylate" refers to a compound comprising two methacrylate moieties as defined herein (e.g., methacrylate ester moieties)

A "diamine" refers to a compound comprising two amine groups.

A "dithiol" refers to a compound comprising two thiol groups.

An "aminothiol" refers to a compound comprising an amine group and a thiol group.

An "amino acid" refers to a compound comprising an amine group and a carboxylic acid group.

An "oligopeptide" refers to 2-10 amino acids linked by amide bonds (peptide bonds).

The term "polyester" refers to a polymer comprising ester groups (i.e., —C(=O)—O—) within the polymer backbone.

The term "polycarbonate" refers to a polymer comprising carbonate groups (i.e., —O—C(=O)—O—) within the polymer backbone.

The term "polyurethane" refers to a polymer comprising urethane groups (i.e., —NR'—C(=O)—O—) within the polymer backbone, wherein R' is as defined herein.

The term "polyether urethane" refers to a polymer comprising ether groups (an oxygen atom linking two groups selected from alkyl, aryl, cycloalkyl and heteroaryl groups) and urethane groups (as defined herein) within the polymer backbone.

The term "polyether carbonate" refers to a polymer comprising ether groups (i.e., an oxygen atom linking two alkyl, aryl, cycloalkyl or heteroaryl groups) and carbonate groups (as defined herein) within the polymer backbone.

The term "polyester carbonate" refers to a polymer comprising ester groups (as defined herein) and carbonate groups (as defined herein) within the polymer backbone.

The term "polyester urethane" refers to a polymer comprising ester groups (as defined herein) and urethane groups (as defined herein) within the polymer backbone.

The term "polyanhydride" refers to a polymer comprising anhydride groups (i.e., —C(=O)—O—C(=O)—) within the polymer backbone. The term "polyamide" refers to a polymer comprising amide groups (i.e., —C(=O)—NR'—) within the polymer backbone, wherein R' is as defined herein.

The term "silicone" refers to a polymer having repeating units of —Si(R')(R")—O—, wherein R' is as defined herein, and R" is defined as for R'.

The terms "polyolefin", "polyacrylate" and "polymethacrylate" refer to polymers obtainable by polymerization of an olefin (alkene), acrylate and methacrylate, respectively.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Materials:
Benzoyl peroxide was obtained from Fluka.
ϵ-Caprolactone was obtained from ACROS Organics.
Ethylene glycol dimethacrylate (EGDMA) was obtained from Aldrich.
Hexamethylene diisocyanate (HDI) was obtained from Aldrich.
2-Hydroxyethyl methacrylate (HEMA) was obtained from Aldrich.
L-lactide and D-lactide were obtained from Boehringer Ingelheim.
D,L-lactide was obtained from ACROS Organics.
N,N-dimethyl-p-toluidine was obtained from Aldrich.
Polyacrylic acid (PAA) was obtained from Aldrich.

Polycaprolactone (PCL2000, PCL1250 and PCL530) was obtained from Aldrich.

Polyethylene glycol 2000 (PEG2000) was obtained from Aldrich.

Polyethylene glycol 6000 (PEG2000) was obtained from Merck.

Polymethyl methacrylate (PMMA) was obtained from Aldrich.

Poly(styrene-methyl methacrylate) (SMMA) was obtained from Aldrich.

Polytetramethylene glycol (PTMG650 and PTMG1000) was obtained from Aldrich.

Stannous 2-ethyl hexanoate was obtained from Sigma.

Methods:

Polymer molecular weights were characterized by gel permation chromatography (GPC), using a Waters 2690 Separation Module with a Waters 410 differential refractometer and Millenium Chromatography Manager.

Thermal properties and crystallinity were characterized using a Mettler TA 3000 differential scanning calorimeter.

Mechanical properties were determined using an Instron apparatus.

Example 1

Polymer Syntheses

Polycaprolactone Polyurethane (CLUR)

Polycaprolactone polyurethane co-polymers are generally prepared by co-polymerizing a polycaprolactone-based polymer with hexamethylene diisocyanate, following the exemplary procedures described hereinafter. The polycaprolactone chain is terminated with functional groups that will allow it to react with the diisocyanate, for example, hydroxy, amine, thiol or carboxylic acid groups.

The polycaprolactone-based polymers PCL2000, PCL1250 and PCL530 were copolymerized with hexamethylene diisocyanate (HDI) to obtain copolymers referred to herein as CLUR (caprolactone urethane) polymers.

As an example, the synthesis of CLUR2000 from PCL2000 and HDI is depicted schematically in FIG. 10 and described in detail as follows.

50.0 grams of OH-terminated PCL2000 was dried at 120° C. under a vacuum for 2 hours with magnetic stirring. Hexamethylene diisocyanate and stannous 2-ethyl hexanoate were added to the reaction mixture at molar ratios of 1:1 (to PCL2000) and 1:100 (to PCL2000), respectively, and reacted at 90° C. for 30 minutes with mechanical stirring under a dry nitrogen atmosphere. The obtained product was dissolved in 150 ml dry dioxane and precipitated in 1200 ml petroleum ether 40-60. The polymer, referred to herein as CLUR2000, was then filtered and dried under a vacuum at room temperature for 24 hours.

Using essentially the same procedures, CLUR1250 was prepared using PCL1250, and CLUR530 was prepared using PCL530. In addition, CLUR530-2000 was prepared using various molar ratios of PCL530 and PCL2000. For example, CLUR530-2000 1:1 was prepared using a 1:1 molar ratio of PCL530 and PCL2000.

The molecular weights, polydispersity indices (PDI), thermal properties and mechanical properties of the CLUR polymers are shown in Table 1.

TABLE 1

Properties of CLUR polymers

| Polymer | Mn (g/mol) | MW (g/mol) | PDI | Tm (° C.) | Crystallinity (%) | Modulus (MPa) |
|---|---|---|---|---|---|---|
| CLUR530 | 126,200 | 137,300 | 1.1 | 40 | 11 | 48 ± 8 |
| CLUR1250 | 98,400 | 111,500 | 1.1 | 38 | 16 | 32 ± 6 |
| CLUR2000 | 107,400 | 121,400 | 1.1 | 48 | 26 | 183 ± 6 |
| CLUR530-2000 1:1 | 120,000 | 130,500 | 1.1 | 36 | 14 | 14 ± 3 |

In comparison, PCL2000 exhibited a Tm of 59° C. and a crystallinity of 51%.

CLUR2000 exhibited water absorption of 3-5%.

Poly(Caprolactone-Ethylene Glycol) Polyurethane (e-Clur):

Poly(caprolactone-ethylene glycol) polyurethane co-polymers are generally prepared by co-polymerizing a polycaprolactone-based polymer with a polyethylene glycol and hexamethylene diisocyanate, following the exemplary procedures described hereinafter. The preparation follows a similar chemistry as the preparation of CLUR polymers described above.

Polycaprolactone-based polymers were copolymerized with polyethylene glycol (2 kDa or 6 kDa) and hexamethylene diisocyanate (HDI), to obtain copolymers referred to herein as e-CLUR polymers.

As an example, the synthesis of e-CLUR2000 (also referred to herein as e-CLUR2K-2K) from PCL2000, PEG2000 and HDI is depicted schematically in FIG. 11.

e-CLUR2000 was prepared using various PEG:PCL molar ratios. The synthesis of e-CLUR2000 with a 1:10 PEG:PCL molar ratio is described in detail as follows.

25.0 grams of OH-terminated PCL2000 and 2.5 grams of PEG2000 were dried at 120° C. under a vacuum for 2 hours with magnetic stirring. Hexamethylene diisocyanate (HDI) and stannous 2-ethyl hexanoate were then added to the reaction mixture at molar ratios of 1:1 and 1:100 (to total PCL2000+PEG2000), respectively, and reacted at 90° C. for 30 minutes with mechanical stirring under a dry nitrogen atmosphere. The obtained product was dissolved in 150 ml dry dioxane and precipitated in 1200 ml petroleum ether 40-60. The e-CLUR2000 polymer was then filtered and dried under a vacuum at room temperature for 24 hours.

Using essentially the same procedures, e-CLUR2000 (e-CLUR2K-2K) was prepared using 2:10 or 3:10 PEG:PCL molar ratios. In addition, e-CLUR2K-6K was prepared using PCL2000 and PEG6000.

The molecular weights, polydispersity indices (PDI), thermal properties and mechanical properties of the e-CLUR polymers are shown in Table 2.

TABLE 2

Properties of e-CLUR polymers

| Polymer (molar % of PEG relative to PCL) | Mn (g/mol) | MW (g/mol) | PDI | Tm (° C.) | Crystallinity (%) | Modulus (MPa) |
|---|---|---|---|---|---|---|
| e-CLUR2K-2K (10%) | 86,000 | 103,900 | 1.2 | 46 | 27 | 194 ± 17 |
| e-CLUR2K-2K (20%) | 98,900 | 112,600 | 1.1 | 48 | 26 | 187 ± 14 |

TABLE 2-continued

Properties of e-CLUR polymers

| Polymer (molar % of PEG relative to PCL) | Mn (g/mol) | MW (g/mol) | PDI | Tm (° C.) | Crystallinity (%) | Modulus (MPa) |
|---|---|---|---|---|---|---|
| e-CLUR2K-2K (30%) | 90,400 | 106.600 | 1.2 | 47 | 21 | 147 ± 6 |
| e-CLUR2K-6K (10%) | 124,600 | 180,400 | 1.4 | 55 | 29 | 191 ± 15 | e-CLUR polymers were considerable more hydrophilic than CLUR polymers, with e-CLUR2000 exhibiting water absorption of 120-150%, in contrast to the 3-5% absorption by CLUR2000.

Polytetramethylene Glycol (PTMG) Polyurethane:

Polytetramethylene glycol polyurethane co-polymers are generally prepared by co-polymerizing polytetramethylene glycol with a bifunctional molecule, such as a diisocyanate (e.g., hexamethylene diisocyanate), following the exemplary procedures described hereinafter.

20.0 grams of PTMG650 were dried at 120° C. under a vacuum for 2 hours with magnetic stirring. Hexamethylene diisocyanate (HDI) and stannous 2-ethyl hexanoate were then added to the reaction mixture at molar ratios of 1:1 and 1:100 (to PTMG650), respectively, and reacted at 70° C. for 1 minute, with mechanical stirring under a dry nitrogen atmosphere. The obtained product was dissolved in 150 ml dry dioxane and precipitated in 1200 ml petroleum ether 40-60. The PTMG polyether-urethane polymer was then filtered and dried under a vacuum at room temperature for 24 hours.

The modulus of the PTMG650 polyurethane was 90±8 MPa.

Poly(Caprolactone-Lactic Acid) Polyurethane:

Poly(caprolactone-lactic acid) polyurethane co-polymers are generally prepared by co-polymerizing a polycaprolactone-based polymer with lactides (e.g., L-lactide, D-lactide or D,L-lactides) and hexamethylene diisocyanate, following the exemplary procedures described hereinafter.

Triblock copolymerss of polylactic acid-polycaprolactone-polylactic acid (PLA-PCL-PLA) were prepared by the ring opening polymerization of the lactide (L-lactide, D-lactide or D,L-lactides) initiated by the hydroxyl end groups of the PCL polymers. Chain extension of the triblock was then carried out using hexamethylene diisocynate (HDI), producing a polyester-urethane.

Poly(Caprolactone-Tetramethylene Glycol) (PCL-PTMG) Polyurethane:

Poly(caprolactone-tetramethylene glycol) polyurethane co-polymers are generally prepared by co-polymerizing a polycaprolactone-based polymer with polytetramethylene glycol and hexamethylene diisocyanate, following the exemplary procedures described hereinafter.

Triblock copolymers of polycaprolactone-polytetramethylene glycol-polycaprolactone (PCL-PTMG-PCL) are prepared by the ring opening polymerization of ε-caprolactone initiated by the hydroxyl end groups of polytetramethylene glycol (e.g., PTMG1000). Chain extension of the triblock is then carried out using hexamethylene diisocyanate (HDI), producing a polyether-ester-urethane.

Example 2

Preparation of Devices

The following describes exemplary methodologies used for preparing a device according some embodiments of the invention.

Dip Coating:

Devices were prepared by dip coating on a suitable mold, typically a cylindrical (6-10 mm diameter) polytetrafluoroethylene-coated mandrel, by slowly dipping the mold into a container containing a solution of 15-20% (w/w) polymer in chloroform, and then slowly withdrawing the mold.

Dipping and withdrawing the mold was performed at a constant velocity in order to obtain a uniform coating. An electronic motor was used to control the vertical movement and speed during the dipping and withdrawing of the mold. The polytetrafluoroethylene-coated mandrel was dipped 7 cm into the polymer solution using a cross head speed (CHS) of 10 mm per minute.

For the formation of devices with a wall thickness of 300-700 μm, 5 to 10 dipping cycles were preformed, and the polytetrafluoroethylene-coated mandrel was then dried at room temperature overnight. After the evaporation was complete and the polymer was dry, the polymer tube was extracted from the mandrel.

CLUR2000 and e-CLUR2000 tubes prepared according to this method are shown in FIGS. 12A and 12B, respectively.

Electrospinning:

Electrospinning is a technique capable of producing nanometric fibers in a relatively well controlled and reproducible manner, producing highly porous 2-dimensional meshes as well as 3-dimensional constructs. Electrospinning is effected by applying a high voltage, using an electrode, to a capillary filled with the polymer fluid to be spun. The resulting fibers are collected on a grounded plate.

In an exemplary procedure, 8-15% (w/w) polymer solutions in chloroform were used, and the grounded plate was metal mandrel with a 5.5 mm diameter. The distance between the electrospinning needle and the collector mandrel was between 10-60 cm, depending on the thickness of the fibers to be obtained. Voltages in a range of from 5 kV to 30 kV were utilized for the formation of device walls with thicknesses in a range of from 300 μm and 700 μm, respectively.

Air Spray:

This technique is capable of forming nanometric and micrometric fibers in a relatively well controlled and reproducible manner, producing porous structures. The air spray technique is effected by passing high pressure dry air through a capillary filled with a solution containing the polymer to form an aerosol, which is sprayed on a collector, such as a rotating polytetrafluorethylene-coated mandrel. An exemplary air spray technique is depicted in FIG. 13.

In an exemplary procedure, 8-15% (w/w) polymer solutions in chloroform were used. The distance between the polymer spray gun and the collector mandrel varied between 10 cm and 60 cm, for the formation of the devices with wall thicknesses ranging from 300 μm to 700 μm. A 2 bar air pressure was applied.

As shown in FIG. 14, the air spray technique produces a polymer in the form of a network of fibers.

As shown in FIG. 15, the diameter of the fibers in the network depends on the type of polymer, its molecular weight, the concentration of the polymer in the aerosol solution and on the distance between the spray gun and the mandrel.

Example 3

Expanded Devices

Tubular structures prepared from CLUR2000 using the air spray technique described in Example 2 were expanded by inserting a balloon into the tubular device and inflating the balloon with warm (50° C.) water.

Due to the shape of the balloon, the tubular structures were expanded primarily in their middle. The less expanded edges of the tubular structures were cut off in order to better observe the expanded middle sections.

As shown in FIG. 16, the diameter of the tubular CLUR2000 structures could be increased considerably by expansion.

Additional air-sprayed CLUR2000 tubular structures were expanded as described above using a balloon which expanded the full length of the tubular structures. The dimensional changes of tubular structures as a result of expansion were then measured and are given in Table 3.

TABLE 3

Dimensional changes of tubular structures as a result of expansion

| Dimension | Before expansion | After expansion | Change |
|---|---|---|---|
| Length (cm) | 7.5 | 7.5 | +0% |
| Inner diameter (mm) | 5.3 | 14.1 | +266% |
| Outer diameter (mm) | 8.2 | 15.3 | +186% |
| Thickness (mm) | 1.4 | 0.6 | −60% |

The effect of expansion on the stiffness of the tubular structures was measured by determining the transverse moduli of the structures before and after expansion.

The mechanical properties of the tubular structure were also determined before and after expansion. The expansion described above increased the modulus from 26±2 MPa to 82±9 MPa, the strain at peak was reduced by expansion from 285±42% to 28±4%, and the stress at peak was increased by expansion from 4.9±0.2 MPa to 9.0±0.6 MPa.

Furthermore, the transition temperature was essentially unchanged by expansion, whereas the crystallinity of the polymer in the tubular structure increased from 26.12% before expansion to 31.59% after expansion.

Expanded tubular structures were re-warmed by reinserting the balloon into the lumen of the structure and filling the balloon with warm (50° C.) water. The balloon was then deflated by removal of the water at a rate of 0.25 ml/second. The tubular structure contracted as the balloon deflated, and the inner wall of the tubular structure remained attached to the balloon.

The expansion and contraction of the tubular structures were reversible over the course of at least 3 or 4 cycles of expansion and contraction.

Example 4

Polymer Devices with an Adhesive Coating

A biocompatible adhesive substance in solid (e.g., powder), semisolid (e.g., gel) or liquid (e.g., solution) form is added to the outer surface of a polymer device, to produce an adhesive coating. The adhesive substance may be added as a layer on top of the outer surface of the polymer device or as a layer incorporated into the polymer of the polymer device.

In an exemplary procedure, biocompatible polyacrylic acid adhesive coatings were added to polymer devices prepared as described hereinabove, according to the following exemplary procedures.

A 2.5% solution of polyacrylic acid (typically having a molecular weight of 1,250,000) in ethanol is sprayed on the top of the outer layer of the device using the air spray technique described in Example 2. The device is then dried in a vacuum at room temperature in order to remove all traces of the solvent.

In an alternative method, powdered polyacrylic acid is homogeneously dispersed on the outer layer of the device. An additional thin layer of fibers is then sprayed over the polyacrylic acid particles in order to retain them on the outer surface of the device.

When the device is exposed to an aqueous medium, the polyacrylic acid coating becomes adhesive, which improves the ability of the device to adhere to tissue and remain in place. The adhesiveness of an exemplary device prepared as described herein and having a polyacrylic acid coating is shown in FIGS. 17A-17D.

Example 5

Polymer Device with Polyurethane Foam

Compressible cuffs are prepared from a foam comprising an elastomer (e.g., a polyurethane and/or a silicone elastomer) and attached (e.g., by crimping) to an outer surface of a polymer device. The cuffs may cover the outer surface of the whole device or cover the ends of the device.

In an exemplary procedure, highly compressible (95% compression) polyurethane foam cuffs were attached to the ends of polymer devices prepared as described hereinabove. The foam cuffs were attached by placing the cuffs around the edges of the device and then crimping the edges of the device, as shown in FIGS. 18A-18C.

The foam cuffs are for improving the ability of the device to grip to a surface.

Example 6

Branched Endograft in an In Vitro Aorta-Renal Branch Model

A branched polymeric endograft was tested using an in vitro model of the aorta-renal branch, which was constructed from perpendicular polymeric tubes. The branched endograft was constructed in situ from two tubular structures (referred to herein as endograft members) prepared from CLUR2000 using the air-spray technique described in Example 2.

In the first step, a branch endograft member was deployed in the tube of the in vitro model which corresponds to the renal artery. As shown in FIGS. 19A and 19B, the endograft member had a tubular structure with flaps at one end.

As shown in FIG. 20, the branch endograft member was placed in the tube of the in vitro model which corresponds to the renal artery, with the flaps at the edge of the endograft protruding into the tube corresponding to the aorta.

The branch endograft member was then expanded "in situ" by inserting a balloon into the endograft member and inflating the balloon with warm (50° C.) water, until the endograft member adhered to the walls of the "renal artery". The balloon was also placed in the "aorta" adjacent to endograft member, and inflated with warm water until the flaps of the endograft member adhered to the wall of the "aorta". The branch endograft member following expansion is shown in FIGS. 21A and 21B.

In the second step, a primary endograft member was deployed in the tube of the in vitro model which corresponds to the aorta, perpendicularly to the previously deployed branch member, as shown in FIGS. 22A-22D.

The two endograft members were then expanded and welded together "in situ" by inserting a balloon into the primary endograft member and inflating the balloon with warm (50° C.) water until a pressure of at least 2 atmospheres is achieved. The welded endograft members are shown in FIGS. 23A and 23B.

As shown in FIG. 24, a hole was then formed outwardly in the wall of the primary endograft member so as to form a single branched structure comprising the two welded endograft members, such that a fluid may flow freely from one member to the other. The balloon was further inflated with warm water in the area of the hole so as to cause protrusions created by formation of the hole to adhere to the walls of the branch endograft member.

The model was then dissected and the branched endograft was removed.

As shown in FIGS. 25A and 25B, the two tubular structures had been welded together, and the inner surfaces of the tubular structures were smooth, showing that protrusions formed by creation of the hole were welded to the walls of the branch member.

These results indicate that moderate heating can be used for both shaping and welding a device in situ.

Example 7

Endograft in Cadaveric Pig Aorta Sections

An endograft prepared from CLUR2000 by air spray, as described in Example 2 hereinabove, was tested in cadaveric pig aorta sections.

As shown in FIGS. 26A and 26B, the endograft was expanded in situ with a balloon filled with warm (50° C.) saline, until the endograft adhered to the walls of the aorta. The attachment of the device to the walls of the aorta lumen was then assessed.

The diameter of the endograft increased by a factor of more than 3, and it became tightly attached to the luminal surface of the vessel. The placement was secure, as it was extremely difficult to remove the endograft from the aorta section. The force required to remove the endograft was approximately 10 times the force typically applied by blood flow at this site.

Example 8

Endograft in an In Vivo Model

An endograft prepared from CLUR2000 by air spray, as described in Example 2 hereinabove, was tested in vivo in a pig aorta. Deployment of the endograft was monitored by an angiography imaging technique.

The endograft was mounted on a balloon, as shown in FIG. 27.

A shown in FIGS. 28A-28F, the mounted endograft was deployed in the aorta of a live pig by inflating the balloon in situ with warm water.

After 8 hours, the pig was sacrificed, and the aorta was examined.

As shown in FIG. 29, the endograft was sufficiently rigid so as to maintain its shape after deployment in the aorta. The placement was secure, as it was extremely difficult to remove the endograft from the aorta.

Example 9

Sealing of an Aneurysm in an In Vitro Model

An in vitro model of an aneurysm was used to determine the ability of an endograft according to embodiments of the invention to seal an aneurysm and improve blood flow. The aneurysm model was prepared from latex, by dip coating a metal mold in a latex solution, and then drying the latex layer and removing the mold.

An endograft with foam cuffs was prepared as described in Example 5 and placed in the aneurysm model, as shown in FIG. 30.

The endograft walls proved to be impermeable to liquid, such that liquid passed through the aneurysm without leakage.

Moreover, as shown in FIG. 31, a vacuum could be applied to the aneurysm, indicating that the endograft sealed the aneurysm against gases in addition to liquids.

Example 10

Polymers with a "Smart" Monomer Component

A polymer is mixed with a monomer which can be polymerized by a suitable stimulation, such that the mixture is an expandable polymeric system. The monomer per se softens the polymer (e.g., by acting as a plasticizer), whereas the polymerized monomer is a solid material which provides mechanical support, and consequently stiffness, to the polymer which was originally in the system. The monomer is thus a "smart component" for hardening the polymeric system when desired.

In an exemplary procedure, films containing various mixtures of a polymer and a monomer were prepared.

PMMA, HEMA and benzoyl peroxide (BP) were dissolved in chloroform at various PMMA:HEMA ratios, and with 100:1 HEMA:BP ratio (w/w). The solution was cast in a Petri dish and the chloroform was allowed to evaporate during the course of 24 hours. Dog-bone samples were cut out of the obtained film, and their modulus was measured using an Instron apparatus. HEMA was then polymerized within the PMMA matrix by adding N,N-dimethyl-p-toluidine to the surface of the PMMA/HEMA films and then incubating the film for 1 hour at 37° C. The modulus of the reacted samples was measured using an Instron apparatus.

As shown in FIG. 32, HEMA considerably reduced the moduli of HEMA:PMMA mixtures in a concentration-dependent manner. As further shown therein, polymerization of the HEMA considerably increased the moduli of the mixtures.

Films containing poly(styrene-methyl methacrylate) (SMMA) and HEMA were prepared as described above for PMMA/HEMA films.

As shown in FIG. 33, HEMA considerably reduced the moduli of HEMA:SMMA mixtures in a concentration-dependent manner, as for HEMA:PMMA mixtures.

The glass transition temperatures ($T_g$) of the HEMA:SMMA mixtures were determined by differential scanning calorimetry.

As shown in FIG. 34, the glass transition temperatures of SMMA decreased considerably in the presence of HEMA. The decrease was concentration-dependent, with 10-30% HEMA resulting in a transition temperature in a range of about 40-55° C., in contrast to the 100° C. transition temperature in the absence of HEMA.

In addition, films containing CLUR2000 as an expandable component (EC) and HEMA as a smart component (SC) were prepared as described above for PMMA/HEMA films.

As shown in FIG. 35, HEMA considerably reduced the moduli of CLUR2000 mixtures in a concentration-dependent manner. As further shown therein, polymerization of the HEMA considerably increased the moduli of the mixtures.

As is further shown in the abovementioned Figures, the moduli of CLUR2000 and CLUR2000/HEMA mixtures were significantly lower than the moduli of PMMA, SMMA and the corresponding PMMA/HEMA and SMMA/HEMA mixtures.

In addition, films containing 80 kDa polycaprolactone (PCL80K) as an expandable component and ethylene glycol dimethacrylate (EGDMA) as a smart component were prepared as described above for PMMA/HEMA films.

As shown in FIG. 36, EGDMA considerably reduced the moduli of PCL80K mixtures in a concentration-dependent manner.

The above results indicate that various monomers can be used as smart components for both softening polymeric materials to varying degrees and hardening the material when desired by polymerization of the smart component.

Example 11

Polymeric Materials with a Cross-Linking "Smart" Component

A device is prepared by using an expandable polymeric material comprising a functional group (e.g., thiohydroxy, amine, azide, alkyne, an unsaturated bond, a nucleophilic leaving group) and a cross-linking molecule, such as a bifunctional molecule (e.g., a diacrylate, a dimethacrylate, a dithiol, a diamine), which comprises functional groups (e.g, a nucleophilic leaving groups, unsaturated bonds, alkyne groups, azide groups, thiohydroxy groups, amine groups) capable of reacting with the functional group of the polymeric material. For example, alkyne groups may be reacted with azide groups by click chemistry.

The polymeric device is placed in a vessel in a body, such that the device is exposed to physiological conditions. When the device is in place, a balloon is inserted into the device and inflated, thereby expanding the device.

Under physiological conditions, the reactions between the cross-linking molecule and the polymeric material are initiated, resulting gradually in cross-linking of the polymeric material. The modulus of elasticity of the polymeric material gradually increases over a period of time as the amount of cross-links increases, and the device becomes stiffer, such that the expanded state of the device is maintained.

In an exemplary procedure, a polymer (e.g., poly(2-hydroxyethyl methacrylate)) comprising alkyne groups (e.g., by linking propargyl alcohol to the polymer via hexamethylene diisocyanate, as shown in FIG. 36), is reacted in situ with a cross-linking molecule comprising azide groups (e.g., polyoxyethylene bis(azide)) via copper(I) catalysis, as shown in FIG. 37. The copper-catalyzed "click" reaction between the azide and alkyne groups results in a cross-linked polymer, which causes the structure to become stiffer.

Example 12

"Smart" Polymeric Systems with Cross-Linking Functional Groups

A device is prepared comprising an expandable polymeric system comprising two complementary functional groups (e.g., an azide and an alkyne, unsaturated carbon-carbon bond and a thiohydroxy, an unsaturated carbon-carbon bond and an amine, a carboxylic acid and an amine, a hydroxy and an isocyanate, an amine and an isocyanate, and a thiohydroxy and an isocyanate) attached to a polymer (e.g., as substituents attached to the polymer backbone). The polymeric system may comprise a polymer having two complementary functional groups, or two polymers, each having a functional group complementary to the functional group of the other polymer.

The polymeric device is placed in a vessel in a body, such that the device is exposed to physiological conditions. When the device is in place, a balloon is inserted into the device and inflated, thereby expanding the device.

Under physiological conditions, reactions between the complementary functional groups are initiated, resulting gradually in cross-linking of the polymer molecules in the polymeric system. The modulus of elasticity of the polymeric system gradually increases over a period of time as the amount of cross-links increases, and the device becomes stiffer, such that the expanded state of the device is maintained.

In an exemplary procedure, a polymer comprising an azide group is prepared using a monomer (e.g., 2-hydroxyethyl methacrylate) with an azide-containing monomer, 2-(2-azidoisobutyloxy)ethyl methacrylate and an alkyne-containing monomer.

The azide-containing monomer is prepared by first preparing 2-(2-bromoisobutyloxy)ethyl methacrylate [Xu et al., *J Poly Sci A: Poly Chem*. 46, 5263-5277 (2008)] by reacting 2-hydroxyethyl methacrylate with 2-bromoisobutyl bromide, and then reacting the 2-(2-bromoisobutyloxy)ethyl methacrylate with sodium azide.

The alkyne-containing monomer is prepared by linking propargyl alcohol to a monomer (e.g., 2-hydroxyethyl methacrylate) via hexamethylene diisocyanate, similarly to the method described in Example 11.

The azide-containing monomer is then copolymerized with the alkyne-containing monomer (e.g., by free radical polymerization), with or without an additional monomer such as 2-hydroxyethyl methacrylate, to obtain a polymer having both azide and alkyne groups.

A device comprising the obtained polymer is placed in a vessel in a body, and the polymer is reacted in situ by copper(I) catalysis. The copper-catalyzed "click" reaction between the azide and alkyne groups results in a cross-linked polymer, which causes the device to become stiffer.

In an additional exemplary procedure, a polymer comprising an azide group is prepared by polymerizing (e.g., by free radical polymerization) the azide-containing monomer described hereinabove, with or without copolymerization with additional monomer such as 2-hydroxyethyl methacrylate. In addition, a polymer comprising an alkyne group is prepared by polymerizing (e.g., by free radical polymerization) the alkyne-containing monomer described hereinabove, with or without copolymerization with additional monomer such as 2-hydroxyethyl methacrylate.

A device comprising the polymer comprising an azide group and the polymer comprising an alkyne group is placed in a vessel in a body, and the two polymers are reacted in situ by copper(I) catalysis. The copper-catalyzed "click" reaction between the azide and alkyne groups results in cross-linking of the two polymers, which causes the device to become stiffer.

Click chemistry encompasses several reactions that are fast, selective, high yielding, and can be conducted in aqueous media and aerobic systems. The most common of these efficient reactions is the copper-catalyzed azide-alkyne cycloaddition, but the toxicity of copper led to the development of bio-orthogonal reactions whose components are inert to the surrounding biological environment and lack metal catalysts, called Cu-free click reactions. One important type of Cu-free click chemistry is the reaction between azide groups and strained cyclo-octyne moieties. One embodiment of the invention harnesses this chemistry, to in situ react two polymers, whereby a substantial stiffening of said polymeric system takes place once the tubular member has been deployed and expanded at the site of an aneurismal sac. One example of this embodiment is the reaction of a derivatized poly(acrylic acid), comprising pendant azide groups, and a derivative of poly(hydroxyl ethylmethacrylate) having pendant cyclo-octyne groups, as follows:

Synthesis of Cyclo-Octyne-Containing Polymer:

8,8-Dibromobicyclo[5.1.0]octane was synthesized according to procedure for the synthesis of 9,9-dibromo [6.1.0]nonane. Then, it was reacted with polyhydroxyethylmethacrylate, $AgClO_4$ and $MeNO_2$ to obtain poly((Z)-2-bromocyclooct-2-enyloxyethylmethacrylate). The product was converted into poly(Cyclooct-2-ynyloxyethylmethacrylate) through a two step reaction with (1) 1,8-diazabicyclo [5.4.0]undec-7-ene and (2)NaOMe and water.

Synthesis of Azide-Containing Polymer:

Polyacrylic acid was reacted with thionyl chloride and O-(2-Aminoethyl)-O'-(2-azidoethyl)nonaethylene glycol was added to produce an amide derivative of polyacrylic acid with pendant azide groups. Alternatively O-(2-Aminoethyl)-O'-(2-azidoethyl)nonaethylene was reacted with methylene chloride and then polymerized with CuBr/2,2-bipyridine to obtain the same product.

The two polymers are subjected to conditions that affect a Cu-free click reaction.

Example 13

Polymeric Systems with a Plasticizer "Smart" Component

A device is prepared comprising an expandable polymeric system comprising a polymer and a small hydrophilic molecule, such as low-molecular weight (e.g., 250-850 grams/mol) polyethylene glycol which plasticizes the polymeric material, thereby rendering the device more expandable and less stiff.

The polymeric device is placed in a vessel in a body, such that the device is exposed to physiological conditions. When the device is in place, a balloon is inserted into the device and inflated, thereby expanding the device.

Continuous contact with an aqueous environment in vivo results in gradual leaching of the hydrophilic plasticizer from the device. The modulus of elasticity of the polymeric system gradually increases over a period of time as the concentration of plasticizer decreases, and the device becomes stiffer, such that the expanded state of the device is maintained.

Example 14

"Smart" Amorphous Polymers

A device is prepared comprising an amorphous polymer capable of undergoing considerably morphological changes by crystallization, resulting in a pronounced increase in the strength and stiffness of the material. The polymeric device is deployed and expanded in its non-crystalline state, characterized by enhanced flexibility, while, in situ, microstructural ordering phenomena take place following stimulation, which result in a marked increase in stiffness over time. The polymer has a suitable segmental mobility at physiological conditions which allows for morphological rearrangement.

The amorphous polymer is formed by exposure to a temperature sufficiently high to melt all crystallites (e.g., 70-80° C.), followed by a very rapid quenching, for example, by immersing the material in liquid nitrogen, to solidify the material while preventing it from crystallizing.

The glass transition temperature of the polymer is below 37° C. When the device is inserted into a body, it is flexible and enables smooth navigation to the site and expansion. After prolonged exposure to physiological temperatures, the polymer reverts to its crystalline state, resulting in the concomitant increase in stiffness.

In an exemplary procedure, a device is prepared comprising an amorphous polymer having the general formula:

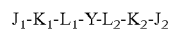

wherein:

$J_1$ and $J_2$ are each a relatively low-weight (e.g., 350 Da) polyalkylene glycol (e.g., methyl polyethylene glycol);

$K_1$ and $K_2$ are each a hydrophobic (e.g., water insoluble) segment;

$L_1$ and $L_2$ are each independently a bifunctional linking moiety or absent; and Y is selected from the group consisting of a polyester (e.g., polycaprolactone), a polyurethane, a polyamide, a silicone polymer, a polyacrylate, a polymethacrylate, and a polyolefin, of suitable molecular weight, as described in detail hereinabove.

The polymeric device is placed in a vessel in a body, such that the device is under physiological conditions at a temperature of 37° C. When the device is in place, a balloon is inserted into the device and inflated, thereby expanding the device. Over a period of time (e.g., 20 minutes), the polymer becomes more crystalline and the device becomes stiffer, such that the expanded state of the device is maintained.

Example 15

"Smart" Amorphous Cross-Linked Polymeric Systems

A device is prepared from an amorphous polymeric system comprising polymeric chains cross-linked by cross-linking moieties (e.g., aliphatic oligoesters) which are degradable (e.g., via enzymatic action) under physiological conditions. The polymeric chains are of a material which would be crystalline or semi-crystalline in the absence of the cross-linking moieties.

The polymeric device is placed in a vessel in a body, such that the device is under physiological conditions. When the device is in place, a balloon is inserted into the device and inflated, thereby expanding the device.

The cross-linking moieties degrade in vivo (e.g., due to activity of esterases). The crystallinity in the polymeric system gradually increases over a period of time as the degree of cross-linking decreases, and the device becomes stiffer, such that the expanded state of the device is maintained.

Example 16

Polymeric Systems with Segregating "Smart" Components

A device is prepared comprising a polymeric system having at least two components. The polymeric device is placed in a vessel in a body, such that the device is under physiological conditions. When the device is in place, a balloon is inserted into the device and inflated, thereby expanding the device.

The components then segregate over a period of time due to chemical incompatibility of the components and/or reaction products of components (e.g., products of polymerization and/or cleavage of cross-linking of the original components). For example, polymerization of a component facilitates segregation by reducing the entropy of a non-segregated mixture, and cleavage of cross-linking facilitates segregation of incompatible components by increasing molecular mobility (e.g., of a polymer chain).

As the phase blending, which inhibits crystallization, decreases, some or all of the segregated components begin to crystallize. Due to the crystallization, segregation results in a gradual increase in the stiffness of the device, such that the expanded state of the device is maintained.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A medical device comprising at least two members as separate units, each of said members comprising a non-metallic expandable tubular structure, implantable in a body vessel and being made, at least in part, from a polymeric system in a solid state, said polymeric system being characterized by a stiffness which changes upon stimulation under physiological conditions, such that said tubular structure is capable of expanding by plastic deformation of said polymeric system at a temperature in a range of from 45° C. to 60° C., and becoming stiffer and retaining an expanded state thereafter at a temperature of 37° C., wherein a wall of said tubular structure in said expanded state is impermeable to liquid, wherein said polymeric system comprises a thermoplastic polymer which undergoes a decrease of its stiffness by at least 20% at a temperature ranging from 40° C. to 60° C., as compared to the stiffness of said thermoplastic polymer at 37° C., and said thermoplastic polymer is characterized by a melting point in a range of from 45° C. to 60° C., and wherein said polymeric system is selected such that at least one of said members is weldable to another of said members in situ.

2. The medical device according to claim 1, wherein said tubular structure is capable of contracting upon stimulation following said expansion, and retaining, at least temporarily, a contracted state thereafter.

3. The medical device according to claim 1, being configured such that welding at least one of said members to another of said members forms a branched tubular structure having at least a first branch member and a second branch member.

4. The medical device according to claim 3, wherein at least one of said branch members comprises a plurality of weldable tubular layer members configured for allowing sequential positioning of said layer members to form, in situ, a multilayer branch member in said body vessel.

5. The medical device according to claim 1, comprising a plurality of weldable tubular layer members configured for allowing sequential positioning of said layer members to form, in situ, a multilayer tubular structure in said body vessel.

6. The medical device according to claim 1, wherein said tubular structure of at least one of said at least two members is a branched tubular structure having a first branch member and a second branch member, and wherein a wall of at least one of said branch members is folded upon itself forming an inner tubular wall within said at least one branch member.

7. The medical device according to claim 6, wherein said folded wall is unfoldable in situ.

8. The medical device according to claim 1, further comprising a compressible member mounted on an end of said tubular structure of at least one of said at least two members, for enhancing fixation of said tubular structure in said body vessel.

9. The medical device according to claim 1, wherein an outer wall of said tubular structure of at least one of said at least two members is coated by a bioadhesive or an adhesive-forming agent for facilitating fixation of said tubular structure to an inner wall of said body vessel.

10. The medical device according to claim 1, wherein an outer wall of said tubular structure of at least one of said at least two members is modified to increase adhesiveness of said outer wall for enhancing fixation of said tubular structure to an inner wall of said body vessel.

11. The medical device according to claim 1, identified for use in a method of lining said body vessel.

12. A method of lining a body vessel, the method comprising introducing the medical device of claim 1 into the body vessel.

13. The method according to claim 12, wherein said body vessel is a blood vessel, the method being for treating an aneurysm in said blood vessel in a subject in need thereof.

14. The method according to claim 13, wherein said aneurysm is an aortic aneurysm.

15. The method according to claim 14, wherein said aneurysm is an abdominal aortic aneurysm.

16. The method according to claim 12, further comprising expanding the medical device in situ to thereby form said expanded state.

17. The method according to claim 16, further comprising, subsequent to said expanding of the medical device in situ, subjecting the medical device to said stimulation, to thereby increase said stiffness of said polymeric system.

18. The method according to claim 16, further comprising, prior to said expanding of the medical device in situ, decreasing said stiffness of said polymeric system.

19. A medical device comprising a non-metallic expandable tubular structure, said tubular structure being implantable in a body vessel and consisting of a polymeric system in a solid state, said polymeric system being configured to produce a polymeric material by polymerization and/or cross-linking upon stimulation under physiological conditions, such that a stiffness of said polymeric material is higher than a stiffness of said polymeric system, such that said tubular structure is capable of expanding, becoming stiffer upon production of said polymeric material and retaining an expanded state thereafter, wherein a wall of said tubular structure in said expanded state is impermeable to liquid.

20. The medical device according to claim 19, wherein said polymeric system comprises a polymer and a compound which reacts with said polymer upon said stimulation, so as to produce said polymeric material.

21. The medical device according to claim 19, wherein said polymeric system comprises a polymer having a first functional group and a polymer having a second functional group, wherein said first functional group and said second functional group are capable of reacting with one another upon said stimulation under physiological conditions to form a cross-linked polymer as said polymeric material, wherein said polymer having a first functional group and said polymer having a second functional group may be different polymers or the same polymer, said same polymer being a polymer having said first functional group and said second functional group.

22. The medical device according to claim 21, wherein said polymeric system comprises said polymer having said first functional group and said second functional group.

23. The medical device according to claim 19, wherein said polymeric system comprises a polymer and at least one of a monomer or an oligomer which undergoes polymerization upon said stimulation.

24. A method of lining a body vessel, the method comprising introducing the medical device of claim 19 into the body vessel.

25. The method according to claim 24, wherein said body vessel is a blood vessel, the method being for treating an aneurysm in said blood vessel in a subject in need thereof.

26. The method according to claim 25, wherein said aneurysm is an aortic aneurysm.

27. The method according to claim 24, further comprising expanding the medical device in situ to thereby form said expanded state.

28. The method according to claim 27, further comprising, subsequent to said expanding of the medical device in situ, subjecting the medical device to said stimulation, to thereby increase said stiffness of said polymeric system.

29. A medical device comprising a non-metallic expandable tubular structure, implantable in a body vessel and being made, at least in part, from a polymeric system in a solid state, said polymeric system being characterized by a stiffness which changes upon stimulation under physiological conditions, such that said tubular structure is capable of expanding, becoming stiffer and retaining an expanded state thereafter, wherein a wall of said tubular structure in said expanded state is impermeable to liquid, and wherein said polymeric system comprises a polymer and a water-soluble compound having a molecular weight of less than 2000 Da which plasticizes said polymer.

30. A method of lining a body vessel, the method comprising introducing the medical device of claim 29 into the body vessel.

31. The method according to claim 30, wherein said body vessel is a blood vessel, the method being for treating an aneurysm in said blood vessel in a subject in need thereof.

32. The method according to claim 31, wherein said aneurysm is an aortic aneurysm.

33. The method according to claim 31, further comprising expanding the medical device in situ to thereby form said expanded state.

34. A medical device comprising a non-metallic expandable tubular structure, implantable in a body vessel and being made, at least in part, from a polymeric system in a solid state, said polymeric system being characterized by a stiffness which changes upon stimulation under physiological conditions, such that said tubular structure is capable of expanding, becoming stiffer and retaining an expanded state thereafter, wherein a wall of said tubular structure in said expanded state is impermeable to liquid, wherein said polymeric system comprises a polymer in an amorphous solid state, and wherein at least a portion of said amorphous solid state undergoes crystallization upon said stimulation under physiological conditions, to thereby produce a polymeric material comprising a crystalline form of said polymer, such that a stiffness of said polymeric material is higher than a stiffness of said polymeric system.

35. A method of lining a body vessel, the method comprising introducing the medical device of claim 34 into the body vessel.

36. The method according to claim 35, wherein said body vessel is a blood vessel, the method being for treating an aneurysm in said blood vessel in a subject in need thereof.

37. The method according to claim 36, wherein said aneurysm is an aortic aneurysm.

38. The method according to claim 35, further comprising expanding the medical device in situ to thereby form said expanded state.

* * * * *